(12) United States Patent
Holzmayer et al.

(10) Patent No.: US 6,613,506 B1
(45) Date of Patent: Sep. 2, 2003

(54) COMPOSITIONS AND METHODS FOR INHIBITING HUMAN IMMUNODEFICIENCY VIRUS INFECTION BY DOWN-REGULATING HUMAN CELLULAR GENES

(75) Inventors: Tanya A. Holzmayer, Mountain View, CA (US); Stephen J. Dunn, Mountain View, CA (US)

(73) Assignee: Subsidiary No. 3, Inc., Wilmington, NC (US)

( * ) Notice: Subject to any disclaimer, the term of this patent is extended or adjusted under 35 U.S.C. 154(b) by 0 days.

(21) Appl. No.: 09/724,916

(22) Filed: Nov. 28, 2000

(51) Int. Cl.$^7$ ................................................. C12Q 1/70
(52) U.S. Cl. ........................ 435/5; 424/208.1; 435/7.1; 435/375
(58) Field of Search ............................. 424/9.2, 208.1; 435/5, 7.1, 375

(56) References Cited

U.S. PATENT DOCUMENTS

| | | | |
|---|---|---|---|
| 4,786,593 A | 11/1988 | Ross et al. ...................... | 435/7 |
| 4,855,241 A | 8/1989 | Johnson, Jr. ................ | 436/548 |
| 5,217,889 A | 6/1993 | Roninson et al. ......... | 435/172.3 |
| 5,256,534 A | 10/1993 | Butera et al. ................ | 435/5 |
| 5,527,884 A | 6/1996 | Russell et al. ................ | 530/350 |
| 5,688,511 A | 11/1997 | Gaynor et al. ............ | 424/207.1 |
| 5,733,543 A | 3/1998 | Nabel et al. .............. | 424/93.21 |
| 6,025,198 A | 2/2000 | Bennett et al. .............. | 435/375 |
| 6,071,743 A | 6/2000 | Holzmayer et al. ......... | 435/325 |
| 6,080,842 A | 6/2000 | Hillman et al. .............. | 530/350 |
| 6,218,162 B1 * | 4/2001 | Krystal ....................... | 435/196 |

FOREIGN PATENT DOCUMENTS

| | | |
|---|---|---|
| EP | 594881 | 10/1992 |
| WO | WO9007936 | 7/1990 |
| WO | WO9012087 | 10/1990 |
| WO | WO9207071 | 4/1992 |
| WO | WO9306216 | 4/1993 |
| WO | WO9311230 | 6/1993 |
| WO | WO9410302 | 5/1994 |
| WO | WO9416060 | 7/1994 |
| WO | WO9426877 | 11/1994 |
| WO | WO9513379 | 5/1995 |
| WO | WO 98/54366 | 12/1998 |

OTHER PUBLICATIONS

Mitsuya et al. Suramin protection of T Cells in vitro against infectivity and cytopathic effect of HTLV–III. Science, (1984) vol. 22 pp. 172–174.*
Sandstrom et al.Antiviral Therapy in AIDS: Clinical and pharmacological properties and therapeutic experience to date. Drugs (1987) vol. 34, pp. 372–390.*
Fortin et al. Regulation of nuclear factor of activated T–cells by phosphotyrosyl–specific phosphatase activity: a positive effect o HIV–1 long terminal repeat driven transcritpion and a possible implication of SHIP. Blood (2001), vol. 97, No. 8, pp. 2390.*
Erneux et al. The diversity and possible functions of the inositol polyphosphate–5–phosphatases. Biochimica et Biophysica Acta (1998) vol. 1436, pp 185–199.*
Geier et al. The human SHIP gene is differentially expressed in cell lineages of bone marrow and blood. Blood (1997) vol. 89, No. 6, pp 1876–1885.*
Scott et al. The pendred syndrome gene encodes a chloride–iodide transport protein. Nature Genetics (1999) vol. 21, pp. 440–443.*
Bork P. Powers and pitfalls in sequence analysis: The 70% hurdle. Genome Research (2000) vol. 10, pp. 398–400.*
Abramson et al., "The ATP–dependent Interaction of Eukaryotic Initiation Facotrs with mRNA", 1987, J. Biol. Chem. 262:3826–3832.
Altmann et al., "The Saccharompyces cervisiae translation initiation factor Tif3 and its mammalian homologue, eIF–4B, have RNA annealing activity", 1995, EMBO J. 14:3820–3827.
Anderson et al., "Human Gene Therapy", 1981, Nature 290–457.
Andjelkovic et al., "The catalytic subunit of protein phosphatase 2A associates with the translation termination factor eRF1", 1996, EMBO J. 15:7156–67.
Antisense '97: A Roundtable on the State of the Idustry, Nature Biotechnology, vol. 15, pp. 519–524, Jun. 1997.
Balliet et al., "Distinct Effects in Primary Macrophages and Lymphocytes of the Human Immunodeficiency Virus Type 1 Accessory Genes vpr, vpu, and nef: Mutational Analysis of a Primary HIV–1 Isolate", 1994, Virology 200:623–631.
Barre–Sinoussi et al., "Isolation of a T–Lymphotropic Retrovirus from a Patient at Risk for Acquired Immune Deficiency Syndrome (AIDS)", 1983 220:868–870.
Bartolazzi et al, "Glycosylation of CD44 is Implicated in CD44–mediated Cell Adhesion to Hyaluronan", 1996, J. Cell Biol. 132:1199–1208.
Baudet et al., "Differentially expressed genes in C6.9 glioma cells during vitamin D–induced cell death program", 1998, Cell Death Differ, 5:116–125.
Bednarik & Folks, "Mechanisms of HIV–1 latency", 1992, AIDS 6:3–16.
Bevec et al., "Inhibition of human immunodeficiency virus type 1 replication in human T cells by retroviral–mediated gene transfer of a dominant–negative Rev. Trans–activator", 1992, Proc. Natl. Acad. Sci. USA 89:9870–74.

(List continued on next page.)

Primary Examiner—James Housel
Assistant Examiner—Ulrike Winkler
(74) Attorney, Agent, or Firm—Sheridan Ross P.C.

(57) ABSTRACT

The present invention relates to nucleic acid molecules involved in HIV infection, proteins encoded by such nucleic acid molecules, and protective compounds including such nucleic acid molecules, proteins and inhibitors of products encoded by such nucleic acid molecules. In addition, the invention also relates to methods for identifying additional genetic suppressor elements, cellular genes corresponding to such GSEs, and methods of using such cellular genes and their encoded products in screening assays for selecting additional inhibitors of HIV.

4 Claims, 9 Drawing Sheets

OTHER PUBLICATIONS

Bittner et al., *"Expression and Secretion Vectors for Yeast"*, 1987, Methods in Enzymol. 153:516–544.

Borgatti et al., *"Extracellular HIV–1 Tat Protein activates phosphatidylinositol 3–and Akt/PKB kinases in $CD4^+$ T lymphoblastoid Jurkat cells"*, 1997, Eur. J. Immunol. 27:2805–2811.

Brady et al., Specific ablation of human immunodeficiency virus Tat–expressing cells by conditional toxic retroviruses, 1994, Proc. Natl. Acad. Sci. USA 91:365–369.

Branch et al., *"A Good Antisense Molecule is Hard to Find"*, TIBS Feb. 23, 1998 pp. 45–50.

Branch et al., *"A Good Antisense Molecule is Hard to Find"*, TIBS Feb. 23, 1998 pp. 45–50.

Bushschacher et al., *"Effects of Second–Site Mutation on Dominant Interference by a Human Immunodeficiency Virus Type 1 Envelope Glycoprotein Mutant"*, 1995, J. Virol. 69:1344–1348.

Camaur et al., *"Human Immunodeficiency Virus Matrix Tyrosine Phosphorylation: Characterization of the Kinase and its Substrate Requirements"*, 1997, Virology 71:6834–6841.

Cantley et al., *"Oncogenes and Signal Trasduction"*, 1991, Cell 64:281–301.

Carballo et al., *"Characterization and Purification of a Protein Kinase C Substrate in Human B Cells"*, 1996, J. Immunol. 156:1709–1713.

Carver et al., *"SHIP inhibits Akt activation in B cells through regulation of Akt membrane localization"*, 2000, Blood 96:1449.

Chatterjee et al., *"Dual–Target Inhibition of HIV–1 in Vitro Means of an Ademo–Associated Virus Antisense Vector"*, 1992, Science 258:1485.

Chinen et al., *"Isolation and mapping of the human beta–signal sequence receptor gene (SSR2)"*, 1995, Cytogenet Cell Genet. 70:215–217.

Cho et al., *"Homeostasis of chemokines, interferon production and lymphocyte subsets: implications for AIDS pathogenis"*, 1997, Biomed. Pharmacother. 51:221–229.

Chomym et al., *"Six unidentified reading frames of human mitochondrial DNA encode components of the respiratory–chain NADH dehydrogenase"*, 1985, Nature 314:592.

Clavel et al., *"Isolation of a New Human Retrovirus from West African Pateints with AIDS"*, 1986, Science 233:343–346.

Coche et al, *"Generation of an unlimited supply of a subtracted probe using magnetic beads and PCR"*, 1994, Nucleic Acids Res. 22:1322–1323.

Cochi et al., Identification of RANTES, MIP–1α, and MIP–1β as the Major HIV–Suppressive Factors Produced by $CD8^+$ T Cells, 1995, Science, 270:1811–1815.

Cohen, *"Exploiting the HIV–Chemokine Nexus"*, 1997, Science 275:1261.

Crooke, S.T. Chapter 1 in Antisense Research and Application, (ed. Stanley Crooke), Springer–Verlag, New York, 1998, pp. 1–50.

Daar et al., *"High Concentrations of Recomninant soluble CD4 are required to neutralize primary human immunodeficiency virus type 1 isolated"*, 1990, Proc. Natl. Acad. Sci. USA 87:6574–6579.

Dalgleish et al., "The CD4 (T4) antigen is an essential component of the receptor for the AIDS retrovirus", 1984, Nature 312:763–767.

DA Silva et al., "Cloning of a novel T–Cell protein FYB that binds FYN and SH2–domain–containing leukocyte protein 76 and modulates interleukin 2 production", 1997, Proc. Natl. Acad. Sci USA 94:7493–7498.

David et al., Interaction with Newly Synthesized and Retained Proteins in the Enoplasmic Retuculum Suggests a Chaperone Function for Human Integral Membrane Protein IP90 (Calnexin)*, 1993, J. Biol. Chem. 268:9585–9592.

Davis et al., *Thioltransferase (Glutaredoxin) is Detected Within HIV–1 and Can Regulate the Activity of Glutathionylated HIV–1 Protease in Vitro*, 1997, J. Biol. Chem 272:25935–25940.

Degli et al., *"Natural substances (acetongenins) from the family Annonaceae are powerful inhibitors of mitochondrial NADH dehydrogenase (Complex I)"*, 1994, Biochem. J. 301:161.

Dropulic et al., *"Functional Characterization of a U5 Ribozyme: Intracellular Suppression of Human Immunodeficiency Virus Type 1 Expression"*, 1992, J. Virol.66:1432–1441.

Dunn et al., *"Isolation of efficient antivirals: genetic suppressor elements against HIV–1"*, 1999, Gene Therapy 6:133–137.

Duttaroy et al., *"Apoptosis Rate Can Be Accelerated fo Decelerated by Overexpression or Reduction of the Level of Elongation Factor–1α"*, 1998, Exp. Cell Res. 238:168–176.

Ensoli et al., "Tat protein of HIV–1 Stimulated growth of cells derived from Kaposi's sarcoma lesions of AIDS patients", 1990, Nature 345:84–86.

Erickson, *"Design, Activity, and 2.8 Å Crystal Structure of a $C_2$ Inhibitor Complexed to HIV–1 Protease"*, 1990, Science 249:527–533.

Everett et al., "A Novel Ubiquitin–Specific Protease is dynamically associated with the PML nuclear domain and binds to a herpesvirus regulatory protein", 1997, EMBO J. 16:556–557.

Fearnley et al., "A homologue of the nuclear coded 49 Ra subunit of bovine mitochondrial NADH–ubiquinone reductase is coded in chloroplast DNA", 1989, EMBO J. 8:665.

Fischer et al., *"N–Butyldeooxynojirimycin–Mediated Inhibition of Human Immunodeficiency Virus Entry Correlated with Impaired gp120 Shedding and gp41 Exposure"*, 1996, J. Virol. 70:7153–7160.

Fisicaro et al., "Identification of Genes Downregulated in the Thymus by Cyclospoin–A: Preliminary Characterization of Clone CSA–19", 1995, Molecular Immunology 32:565–572.

Flanagan W.M. et al., "Cellular Penetration and Antisense Activity by a phonoxazine–Substituted Heptanucleotide", Nature Biotechnolgy vol. 17, Jan. 1999, pp. 48–52.

Flohr et al., "Interferon–γ regulates expression of a novel keratin classe I gene*" 1992, Eur J. Immunol. 22:975–979.

Foley et al., "Continuous Culture of Human Lymphoblasts from Peripheral Blood of a Child with Acute Leukemia", 1965, Cancer 18:522–29.

Folks et al., Tumor Necrosis Factor α Induces Expression of Human Immunodeficiency Virus in a Chronically Infected T–cell Clone.

Friedrick et al., Two Binding Sites of Inhibitors in NADH: ubiquinon oxidoreductase (Complex I), 1994, Eur. J. Biochem. 219:691.

Frolova et al., "A Highly conserved eukaryotic protein family prossessing properties of polypeptide chain release factor", 1994, Nature 372:701–703.

Fukuski, "Identification and cloning of novel cellular protein Naf1, Nef–associated factor 1, that increases cell surface CD4 expression" 1999, FEBS Lett. 442:83.

Gal & Gottesman, Isolation and sequence of a cDNA for human–oro–(cathepsin L) 1988, Biochem J. 253:303–306.

Gallo et al., "Frequent Detection and Isolation of Cytopathic Retroviruses (HTLV–III) from Patients with AIDS and at Risk for AIDS", 1984, Science 224:500–503.

Garcia, 1997, "Expression of HIV–1 nef decreases basal phosphatidyl–inositol 3–kinase activity", C.R. Acad. Sci.III 320:505–508.

Gerwitz et al., "Facilitating Oligonucleotide Delivery: Helping Antisense Deliver on its Promise", Proc. Natl. Acad. Sci. Apr. 1996, 93:3161–3163.

Giallongo et al., "Structure of the Human Gene for α–enolase" 1990, Eur. J. Biochem, 190:567–573.

Giallongo et al., "Sturcture of the Human Gene for α–enolase" 1990, Eur. J. Biochem, 190:567–573.

Girjes et al., "Cloning and characterization of cDNA encoding a human arginyl–tRNA synthetase", 1995, Gene, 164:347–350.

Goswami et al. "Purification and Characteriation of a Cytosolic Protein Enhancing GSH–dependent Microsomol Iodothyronin 5'–Monodeiodination" Journal of Biological Chemistry, vol. 260, No. 10, May 25, 1985, pp. 6012–6019.

Graziani et al., "The HIV–1 nef Protein Interferes with Phosphatidylinositol 3–Kinase Activation 1*", 1996, J. Biol. Chem. 271:6590–6593.

Gudkov & Roninson, "Isolation of Genetic Suppressor Elements (GSEs) from Random Fragment cDNA Libraries in Retroviral Vectors", 1996, Methods in Molecular Biology 69:229–231.

Guilemot et al., Physical linkage of a guanine nucleotide–binding protein–related gene to the chicken major histocompatibility complex, 1989, Proc. Natl. Acad. Sci. USA 86:4594–4598.

Guyader et al., "Genome Organization and transactivation of the human immunodeficiency virus type 2", 1987, Nature 326:662–669.

Han et al., "Human Immunodeficiency Virus Type 1 Tat–Mediated trans Activation Correlates with the Phosphorylation State of a Cellular TAR RNA Stem–Binding Factor", 1992, J. Virol. 66:4065–4072.

Handen et al., "Suppression of HIV–1 transcription by β–chemokines RANTES, MIP1–α, and MIP–1β is not mediated by the NFAT–1 enhancer element", 1997, FEBS Lett. 410:301–302.

Hlavin et al., "Molecular Structure and Functional Testing of Human L1 CAM:An Interspecies Comparison", 1991, Genomics 11:416–423.

Hochtrasser, "Ubiquitin, proteasomes, and the regulation of intracellular protein degradation", 1995, Curr. Opin. Cell. Biol. 7:773–785.

Holmgren et al., "Thioredoxin and Glutaredoxin Systems", 1989. J. Biol. Chem. 264:13963–13966.

Horowitz et al., A New cyclophilin and the human homologues of yeast prp3 and prp4 form a complex associated with U$/U6 snRNPs* 1997, RNA 3:1374–1387.

Horowitz et al., A New cyclophilin and the human homologues of yeast prp3 and prp4 form a complex associated with U$/U6 snRNPs* 1997, RNA 3:1374–1387.

Hu et al., "Hsp90 is required for the activity of a hepatitis B virus reverse transcriptase", 1996, Proc. Natl. Acad. Sci. USA 931060–1064.

Huang et al., "Control of Cell Fate by a Deubiquitinating Enzyme Encoded by the fat facets Gene", 1995, Science 270:1828–1831.

Huet et al., "CD44 Contributes to T Cell Activation", 1989, J. Immunol. 143:798–801.

Jenkins et al., "Characterization of HIV–1 Vpr Nuclear Import:Analysis of Signals and Pathways", 1998, J Cell Biol, 143:875–885.

Jongstra–Bilen et al., "Human and Mouse LSP1 Genes Code for Highly Conserved Phosphorproteins" 1990, The Journal of Immunology, vol. 144, 1104–1110.

Joshi et al., "Inhibition of Human Immunodeficiency Virus Type 1 Multiplication by Antisense and Sense RNA Expression", 1991, J. Virol5524–5530.

Junker et al., Intracellular Expression of Human Immunodeficiency Virus Type 1 (HIV–1) Protease Variants Inhibits Replication of Wild–Type and Protease Inhibitor 1996, J. Virol. 70:7765–7772.

Kahn et al., "The Safety and Pharmacokinetics of Recombinant Soluble CD4 (rCD4) in Subjects with the Acquired Immunodeficiency Syndrome (AIDS) and AIDS–Related Complex", 1990, Ann. Int. Med. 112–254–261.

Kato et al., "Cytosolic throid hormone–binding protein is a monomer of pyruvate kinase", 1989, Proc. Natl. Acad. Sci. USA 86:7861–7865.

Keyse and Emslie, "Oxidative stress and heat shock induce a human gene encoding a protein–tyrosine phosphatase", 1992, Nature 359:644–647.

Kim et al., "Characterization of the PEST family protein tyrosine phosphatase BDP1", 1996, Oncogene 13:2275–2279.

Klatzman et al., "T–lymphocyte T4 molecule behaves as the receptor for human retrovirus LAV", 1984, Nature 312:767–768.

Koike et al., "Cloning and nucleotide sequence of the cDNA encoding human 2–oxoglutarate dehydrogenase (lipoamide)"1992,Proc. Natl. Acad. Sci. USA 89:1963–1967.

Koike et al., The gene encoding human 2–oxoglutarate dehydrogenase: structural organization and mapping to chromosome 7p13–p14. 1993, Gene1159:261–266.

Kozak et al., "Determinants of transllational fidelity and efficiency in vertebrate mRNAs", 1994, Biochemie 76:815–821.

Lain et la., "An Inhibitor of Nuclear Export Activates the p53 Response and Induces the Localization of HDM2 and p53 to U1A–Positive Nuclear Bodies Associated with the PODs", 1999, Exp. Cell. Res. 248:457–472.

Lambotte et al., "The Human Gene of a Protein that Modifies Na+ –D–Glucose Co–Transport" 1989, Science 243:1731–1734.

Larder et al., HIV with Reduced Sensitivity to Zidovudine (AZT) Isolated During Prolonged Therapy, Reports 1989, 1731–1734.

Lee et al., "Inhibition of Human Immunodeficiency Virus Type 1 in Human T Cells by a Potent Rev. Response Element Decoy Consisting of the 13–Nucleotide Minimal Rev–Binding Domain", 1994, J. Virology 68:8254–64.

Li et al., "", 1996, Proc. Natl. Acad. Sci. USA 93:9606.

Liscovitch and Cantley, "Lipid Second Messengers", 1994, Cell 77:329–334.

Lisziewicz et al., "Tat–Regulated Production of Multimerized TAR RNA Inhibits HIV–1 Gene Expression", 1993, New Biol. 3:82–89.

Liu et al., "cDNA Cloning and Expression of HIP, a Novel Cell Surface Heparan Sulfate/Heparin–binding Protein of Human Uterine Epithelial Cells and Lines*", , 1996, J. Biol. Chem. 271:11817–11823.

Logan & Shenk, Adenovirus tripartite leader sequence enhances translation of mRNAs later after infection 1984, Proc. Natl. Acad. Sci. USA 81:3655–3659.

Lu et al., ""CDC42 and Rac1 are implicated in the activation of the Nef–associated kinase and replication of HIV–1",", 1996, Current Biology 6:1677–1684.

Lund–Johansen et al., "Apoptosis in Hematopoietic Cells Is Associated with an Extensive Decrease in Cellular Phosphotyrosine Content that can be Inhibited by the Tyrosine Phosphate Antagonist Pervanadate", 1996, Cytometry 25:182–190.

MacDonald et al., "Chromosomal localization[1] of tumor protein, translationaly–controlled 1 (TPT1) encoding the human histamine releasing factor (HRF) to 13q12→q14", 1999, Cytogenet Genet, 84:128–129.

Maddon et al., "The T4 Gene Encodes the AIDS Virus Receptor and is Expressed in the Immune System and the Brain", 1986, Cell 47:333–348.

Majamaa et al., "Difference between collagen hydrozylases and 2–oxoglutarate dehydrogenase in their inhibition by stuctural analogies of 2–oxoglutarate", 1985, Biochem. J. 229:127–133.

Maki et al., "Complimentary DNA encoding the human T–Cell FK506–binding protein, a peptidylprolyl cis–trans isomerase distinct from cyclophilin", 1990, Proc. Natl. Acad. Sci USA 87:5440–5443.

Malim et al., "Stable Expression of Trandominant Rev Protein in Human T Cells Inhibits Human Immunodeficiency Virus Replication" 1992, J. Exp. Med. 176:1197.

Marasco et al., "Design, intracellular expression, and activity of a human anti–human immunodeficiency virus type 1 gp 120 single–chain antibody", 1993, Proc. Natl. Acad. Sci. USA 90:7889–93.

Mateer et al., "Identification of Structural Elements Involved in the Interaction of Simian Virus 40 Small Tumor Antigen with Protein Phosphatase 2A*", 1998, J. Biol. Chem. 273:35339–35346.

Mayer et al., "Isolation, Molecular characterization, and tissue–specific expression of a novel putative G protein–coupled receptor", 1998, Biochim. Biophys. Acta. 1395:301–308.

Mazerolles et al., "Down–regulation of LFA–1 mediated T cell adhesion induced by the HIV envelope glycopoprotein gp160 requires phosphatidylinositol–3–kinase activity", 1997, Eur. J. Immunol.27:2457–2465.

McDougal et al., "Binding of HTLV–III/LAV to T4+ T Cells by a Complex of the 110K Viral Protein and the T4 Molecule", 1986, Science 231:382–385.

Melhem et al., "Characterization of the Gene for a Proliferation–realated Phosphoprotein (Oncoprotein 18) Expressed in High Amounts in Acute Leukemai*", 1991, J.Biol. Chem. 266:17747–17753.

Meroni et al., "Rox, a novel bHLHZip protein expressed in quiescent cells that heterodimerizes with Max, binds a non–canonical E box and acts as a transcriptional repressor", 1997, EMBO J. 15–16:2892–906.

Messaoudi et al., "A Human Milk Factor Susceptible to Cathepsin D Inhibitors Enhances Human Immunodeficieny Virus Type 1 Infectivity and Allows Virus Entry into a Mammary Epithelial Cell Line", 2000, J. Virol. 74:1004–1007.

Methot et al., "A Region Rich in Aspartic Acid, Arginine, Tyrosine, a nd Glycine (DRYG) Mediates Eukaryptic Initiation Factor 4B (eIF4B) Self–Association and Interaction with eIF3", 1996, Mol. Cell. Biol. 16:5328–5334.

Milburn et al., "Cloning and expression of eukaryotic initiation factor 4B cDNA: sequence determination identifies a common RNA recognition motif", 1990, EMBO J. 9:2783–2790.

Miller and Buttimore, "Redesign of Retrovirus Packaging Cell Lines to Avoid Recombination Leading to Helper Virus Production", 1986, Mol. Cell. Biol. 6:2895–2902;ATCC CRL #9078.

Miller and Rosman, "Improved Retroviral Vectors for Gene Transfer and Expression", 1989, BioTechniques 7:980.

Mitsuya et al., "Molecular Targets for AIDS Therapy", 1990, Science 249:1533–1544.

Mitsuya et al., "Targeted Therapy of human immunodeficiency virus–related disease", 1991, FASEB J. 5:2369–2381.

Modesti et al., "Trans–Dominant Tat Mutants with Alteration in the Basic Domain Inhibit HIV–1 Gene Expression", 1991, New Biol. 3:759–768.

Moore, "Coreceptors: Implications for HIV Pathogenesis and Therapy", 1997, Science 276:51–52.

Nandi and Banerjee, "Tyrosine Phosphorylation as a Possible Regulatory Mechanism in the Expression of Human Immunodeficiency Virus Genes", 1995, Med. Hypothesis 45:476–480.

Nara & Fischinger, "Quantitative infectivity assay for HIV–1and–2", 1988, Nature 322:469–70.

Obata et al., "Stucture, Distribution, and Expression of an Ancient Murine Endogenous Retroviruslike DNA Family", 1998, J. Virol. 62:4381–4386.

Ojwang et al., "Inhibition of human immunodefiency virus type 1 expression by a hairpin ribozyme", 1992 Proc. Natl. Acad. Sci. USA 89:10802–06.

Ou et al., "Conformational Changes Induced in the Endoplasmic Reticulum Luminal Domain of Calnexin by Mg–ATP and $Ca^{2+}$*", 1995, J. Biol. Chem. 270:18051.

Palombella et al., The Ubiquitin–Proteasome Pathway is Required for Processing the NF–κB1 Precursor Protein and the Activation of NF–κB. 1995, Cell, 78:773–785.

Park and Levine, "The Human glutaredoxin gene: determination of its organization, transcription start point, and promoter analysis", 1997, Gene 197:189–193.

Pearson et al., "A transdominant tat mutant that inhibits tat–induced gene expression from the human immunodeficiency virus long terminal repeat", 1990, Proc. Natl. Acad. Sci., USA 87:5079–5083.

Pesesse et al. "Identification of a Second SH2–Domain–Containing Protein Closely Related to the Phosphatidylinositol Polyphosphate 5–Phosphatase SHIP", 1997, Biochem Biophys Res. Commun 239:697–700.

Pettit et al., "The specificity of the HIV–1 protease", 1993, Persp. Drug. Discov. Design 1:69–83.

Phipps et al., "Increased Enzymatic Activity of the T–Cell Antigen Receptor–Associated Fyn Protein Kinase in Asymptomatic Patients Infected with the Human Immunodeficiency Virus", 1997, Blood 90:3603–3612.

Pilkington et al., "Mitochondral NADH–Ubiquinone Reductase: Complementary DNA sequences of Import Precursors of the Bovine and Human 34–kDA Subunit", 1989, Biochem. 28:3257.

Poli & Fauci, "The Effect of Cytokines and Pharmacologic Agents on Chronic HIV Infection", 1992, AIDS Res. Human Retroviruses 9:191–197.

Pulford et al., "Lymphocyte–specific protein 1: a specific marker of human leucocytes", 1999, Immunology 96:262–271.

Raboudi, et al., Identification of Cell–suface Heparin/Heparan Sulfate–binding Proteins of a Human Uterine Epithelial Cell Line (RL95)*, 1992, J. Biol. Chem. 267:11930–11939.

Ray et al., "ATP–dependent Unwinding of Messenger RNA Structure by Eukaryotic Initiation Factors*", 1985, J. Biol. Chem. 260:7651–7658.

Rebbe et al., "Nucleotide Sequence and Regulation of a Human 90–kDa Heat Shock Protein Gene", 1989, J. Biol. Chem. 264:15006–15011.

Rhodes et al., "Inhibition of heretologous strains of HIV by antisense RNA", 1991, AIDS 5:145–151.

Rhodes et al., "Inhibition of human immunodeficiency virus replication in cell culture by endogenously synthesized antisense RNA", 1990, J. Gen. Virol. 71:1965.

Rodier et al., "BTG1: A Triiodothyronine Target Involved in the Myogenic Influence of the Hormone", 1999, Exp. Cell. Res. 249:337–348.

Rojanasakul, "*Antisense Oligonucleotide Therapeutics-:Drug Delivery and Targeting*" Advanced Drug Delivery Reviews 18 (1996) 115–131.

Ron et al., "Cloning of an intracellular receptor for protein kinase C: A homolog of the β subunit of G proteins", 1994, Proc. Natl. Acad. Sci. USA 91:839.

Roth et al., "Nucleo–cytoplasmic shuttling of the hdm2 oncoprotein regulates the levels of the p53 protein via a pathway used by the human immunodeficiency virus rev protein", 1998, EMBO J. 15:554–564.

Rouault et al., "BTG1, a member of a new family of antiproliferative genes", 1992, EMBO J. 11:1663–1670.

Rozen et al, "bi–directional RNA Helicase Activity of Eucaryotic Translation Initiation Factors 4A and 4F", 1990, Mol. Cell. Biol. 10:1134–1144.

Russell et al., "The Third Human Homolog of a Murine Gene Encoding and Inhibitor of Stem Cell Proliferation is Truncated and Linked to a CpG Island–Containing Upstream Sequence", 1993, DNA Cell Biol. 12:157–175.

Sanchez et al.,"Translationally controlled tumor protein: A protein identified in several nontumoral cells including erythrocytes", 1997, Electrophoresis 18:150–155.

Sarver et al., "Ribozymes as Potential Anti–HIV–1 Therapeutic Agents", 1990, Science 247:1222–1225.

Scherer et al., "Signal–induced degradation of IκBα requres site–specific ubiquitination", 1995, Proc. Natl. Acad. Sci. USA 92:11259–11263.

Schilling, "A Novel Human DnaJ Protein, hTid–1, a Homolog of the Drosophila Tumor Suppressor Protein Tid56, Can Interact with the human papillomavirus Type 16 E7 Oncoprotein", 1998, Virology 247:74–85.

Schooley et al., "Recombinant Soluble CD4 Therapy in Patients with the Acquired Immunodeficiency Syndrome (AIDS) and AIDS–Related Complex", 1990, Ann, Int. Med. 112:247–253.

Sczakiel et al., "Inhibition of Human Immunodefiency Virus Type 1 Replication in Human T Cells Stably Expressing Antisense RNA", 1991, J. Virol. 65:468–472.

Sczakiel et al., "Tat–and Rev–Directed Antisense RNA Expression Inhibits and Abolishes Replication of Human Immunodeficiency Virus Type 1: a Temporal Analysis", 1992, J. Virol 66:5576–5581.

Shimomura et al., "Capsaicin and Its Analogs Inhibit the Activity of NADH–Coenzyme Q Oxidoreductase of the Mitochondrial Respiratory Chain[1]" 1989, Arch. Biochem Biopys. 270:573.

Shimuzu et al., "Dual Role of the CD44 Molecule in T Cell Adhesion and Activation", 1989, J. Immunol. 143:2457–2463.

Smith et al., "International Cometary Explorer Encounter with Giacobini–Zinner: Magnetic Field Observations", 1986, Science 232:382–385.

Smith et al., "Blocking of HIV–1 Infectivity by a Soluble, Secreted Form of the CD4 Antigen", 1987, Science 238:1704–1707.

Stamenkovich et al., A Lymphocyte Molecule Implicated in Lymph Node Homing is a Member if the Cartilage Link Protein Family, 1989, Cell 56:1057–1062.

Stein, C.A. "Hybridization Predication Gets to First Base", Nature Biotechnology, vol. 17, Aug. 1999, pp. 751–752.

Sullenger et al., Overexpression of TAR Sequences Renders Cells Resistant to Human Immunodeficiency Virus, 1990, Cell 63:601–608.

Sullenger et al., Overexpression of TAR Sequences Renders Cells Resistant to Human Immunodeficiency Virus, 1991, J. Virol 65:6811–6816.

Summers et al., "Analysis of trans–Acting Response Decoy RNA–Mediated Inhibition of Human Immunodefiency Virus Type 1 Trasactivation", 1993, Gene 136:185–192.

Tao et al., "Cloning, expression and characterization of the cDNA encoding human hepatic squalene synthase, and its relationship to phytoene synthase", 1999, Proc. Natl. Acad. Sci. USA 96:3077–3080.

Tao et al., Nucleotoplasmic shutting of oncoprotein Hdm2 is required for Hdm2–mediated degradation of p53, 1999, Proc. Natl. Acad. Sci. USA 96:6937–6941.

Tam et al., "Human cathepsin B–encoding cDNAs: sequence variations in the 3'–untraslated region",1994, Gene 139:171–176.

Torres et al., "Impact of Combination Therapy for HIV Infection on Inpatient Censes", 1997, Infec. Med. 14:142–160.

Trono et al., "HIV–1 Gag Mutants can Dominantly Interfere with the Replication of the Wild–Type Virus", 1989, Cell 59:113–120.

Truant et al., "The Arginin–Rich Domains Present in Human Immunodeficiency Virus Type 1 Tat and Rev Function as Direct Importin β–Dependent Nuclear Localization Signal", 1999, Mol. Cell Biol, 19:1210–7.

Tsai et al., "Isolation and Characterization of the Human Gene for ADP–Ribosylation Factor 3, a 20–kDa Guanine Nucleotide–binding Protein Activator of Cholera Toxin*", 1991, J. Biol. Chem. 266:23053–23059.

Tung et al., Direct activation of protein phosphatase–$2A_0$1997, FEBS Lett. 401:197–201.

Uchida et al., "Down–Regulation of Mitochondrial Gene Expression by the Anti–Tumor Arotinoid Mofarotene", 1994, Int. J. Cancer 58:891.

Uetsuki et al, "Isolation and Characterization of the Human Chromosomal Gene for Polypeptide Chain Elongation Factor–1α*", 1989, J. Biol. Chem. 264:5791–5798.

Varmus, "Retroviruses"1988, Science 240:1427–1439.

Venkatesh et al., "Functional Domains of the HIV–1 rev Gene Required for trans–Regulation and Subcellular Localization", 1990, Virology 176:39–47.

Ventakash et al., "Selective Induction of Toxicity to Human Cells Expressing human immunodeficiency virus type 1 Tat by a conditionally cytotoxic adenovirus vector", 1990, Proc. Natl. Acad. Sci. USA 87:8746–8750.

Vodicka et al., HIV–1 Vpr interacts with the nuclear transport pathway to promote macrophage infection, 1998, Genes Dev, 12:175–185.

Volinina et al., "A Human phosphatidylinositol 3–kinase complex related to the yeast Vps34p–Vps15p protein sorting", 1995, EMBO J. 14:3339–3348.

Walker et al., "Sequences of 20 subunits of NADH: ubiquinone oxidoreductase form bovine heart mitochondria", 1992, J. Mol. Biol. 226:1051.

Walsh et al., "Identification of macrophage activation associated proteins by two–dimensional gel electrophoresis and microsequencing", 1995, J. Leukoc. Biol. 57:507–512.

Walton and Dixon, "Protein Tyrosine Phsophateses", 1993, Ann. Rev. Biochem. 62:101–120.

Ware et al., "Cloning and Characterization of Human SHIP, the 145–kD Inositol 5–Phosphatase That Associates with SHC After Cytokine Stimulation", 1996, Blood 88:2833–2840.

Wang et al., 1997, ArgBP2, a Multiple Src Homology 3 Domain–containing, Arg/Abl–interacting Protein, Is Phosphorylated in v–Abl–trasformed Cells and Localized in Stress Fibers and Cardiocyte Z–disks*, J. Biol Chem. 272:17542–17550.

Wells et al., 1993, Adv. Enzymol. Relat. Areas Molec. Biol. 66:149–201.

Wescrasinghi et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme", 1991, J. Virol. 65:5531–5534.

Wilkingson, "Roles of Ubiquitylation in Proteolysis and Cellular Regulation", 1995, Ann. Rev. Nutr. 15:161–189.

Woffendin et al., "Nonviral and viral delivery of a human immunodeficiency virus protective gene into primay human T cells", 1994, Proc. Natl. Acad. Sci. USA 91:11581–85.

Woffendin et al., "Expressin of a protective gene prolongs survival of T cells in human immunodeficiency virus–infected patients", 1996, Proc. Natl. Acad. Sci., USA 93:2889–2894.

Wozney et al., "Novel Regulators of Bone Formation Molecular Clones and Activities", 1988, Science 242:1528–1534.

Wyatt et al., "The Antianginal Agent Ranolazine is a Weak Inhibitor of the Respiratory Complex I, But with Greater Potency in Broken or Uncoupled Than in Coupled Mitochondria", 1995, Biochem. Pharmacol. 50:1599.

Yamada et al., "Intracellular immunization of human T cells with a hairpin ribozyme against human immunodeficiency virus type 1", 1994, Gene Therapy 1:38–45.

Yarchoan et al., "Phase 1 Atudy of the adminstration of recombinant soluble cd4", 1989, Proc. Vth Int. Conf. on AIDS, p. 564, MCP 137.

Yousefi et al., "Protein–tyrosine phosphorylation regulates apoptosis in human eosinophil and neutrophils", 1994, Proc. Natl. Acad. Sci. USA 91:10868–10872.

Yu et al., "A Hairpin ribozyme inhibits expression of diverse strains of human immundeficiency virus type 1", 1993, Proc. Natl. Acad. Sci. USA 90:6340–6344.

Yu et al., "Intracellular Immunization of Human Fetal Cord Blood Stem/Progenitor Cells with a Ribozyme against Human Immunodeficiency Virus Type 1", 1995, Proc. Natl. Acad. Sci. USA 92:699–703.

Zhu et al., "Molecular Cloning of a Novel Human Leukemia–associated Gene", 1989, J. Biol. Chem. 264:14556–14560.

Zhu et al., "DUB–1, a deubiquitinating enzyme with growth–suppressing activity", 1996, Proc. Natl. Acad. Sci. USA 93:3275–3279.

Zhu, "The interconversion of Protein Phosphatase 2A between $pp2A^1$ and $PP2A^0$ during Retinoic Acid–Induced Granulocytic Differentiation and a Modification on the Catalytic Submit in S Phase of HL–60 $Cells^1$",1997, Arch. Biochem. Biophys. 339:210–217.

Zigman et al., "Human Golfα: Complementary Ceoxyribonucleic Acid Structure and Expression in Pancreatic Islets and Other Tissues Outside the Olfactory Neuroepithelium and Central Nervous System", 1993, Endocrinology 133:2508–2514.

Zolnierowiez & Hemmings, "Testing, targeting and triggering of protein phosphatases", 1994, Trends Cell Biol. 4:61–64.

Zu et al., "Activation of MAP Kinase–Activated Protein Kinase 2 in Human Neutrophils After Phorbol Ester of fMLP Peptide Stimulation", 1996, Blood 87:5287–5296.

Liu et al., *Genomics* 39:109–112 (1997).

Chernock et al., "SHP2 and CBL participate in α–chemokine receptor cxcr4–mediated signaling pathways," Abstract #1020, Poster Board#–Session: 70–II, Publ. Nov. 16, 2000.

* cited by examiner

SEQUENCE LISTING

```
<160> NUMBER OF SEQ ID NOS: 118

<210> SEQ ID NO 1
<211> LENGTH: 135
<212> TYPE: DNA
<213> ORGANISM: Homo sapiens

<400> SEQUENCE: 1
agatcctatt ggtgcgtggg ctttgtatga ttatgggcgt agattagtag tagttactgg      60
ttgaacattg tttgttggtg tatatattgt aattgggatt gctcggggga ataggttatg     120
tgattaggag taggg                                                      135

<210> SEQ ID NO 2
<211> LENGTH: 100
<212> TYPE: DNA
<213> ORGANISM: Homo sapiens

<400> SEQUENCE: 2
gatcctcccg aatcaaccct gaccctctc cttcataaat tattcagctt cctacactat       60
```

-continued

```
taaagtttac cacaaccacc acgccatcat actccttcac                    100

<210> SEQ ID NO 3
<211> LENGTH: 143
<212> TYPE: DNA
<213> ORGANISM: Homo sapiens

<400> SEQUENCE: 3
catcagccct tcttaacatc tacttctacc tacgcctaat ctactccacc tcaatcacac    60
tactccccat atctaacaac gtaaaaataa aatgacagtt tgagcataca aaacccaccc   120
cattcctccc cacactcatc gcc                                          143

<210> SEQ ID NO 4
<211> LENGTH: 100
<212> TYPE: DNA
<213> ORGANISM: Homo sapiens

<400> SEQUENCE: 4
gtgaaagagt atgatggggt ggtggttgtc gtaaacttta atagtgtagg aagctgaata    60
atttataaag gagaggggac agggttgatt cgggaggatc                        100

<210> SEQ ID NO 5
<211> LENGTH: 116
<212> TYPE: DNA
<213> ORGANISM: Homo sapiens

<400> SEQUENCE: 5
gaagaagcag gccggatgtc agaggggtgc cttgggtaac ctctgggact cagaagtgaa    60 aggggctat tcctagtttt attgctatag ccattatgat tattaatgat gagtat       116

<210> SEQ ID NO 6
<211> LENGTH: 127
<212> TYPE: DNA
<213> ORGANISM: Homo sapiens

<400> SEQUENCE: 6
tcctagtcct cacaatcatg gcaagccagc gccacttatc cagtgaacca ctatcacgaa    60
aaaaactcta cctctctata ctaatctccc tacaaatctc attaattata atattcacaa   120
ccacaga                                                            127

<210> SEQ ID NO 7
<211> LENGTH: 105
<212> TYPE: DNA
<213> ORGANISM: Homo sapiens

<400> SEQUENCE: 7
gcgcaaagca cgcgacatgg tggggcaggt ggccatcaca aggattgagc agctgtcgcc    60
attcccsttt gacctcctgc tgaaggaggt gcagaagtac cccaa                  105

<210> SEQ ID NO 8
<211> LENGTH: 105
<212> TYPE: DNA
<213> ORGANISM: Homo sapiens

<400> SEQUENCE: 8
gaaatcctgg aggccagtga tgggatcatg gtggctcgcg gtgatctagg cattgagatt    60
cctgcagaga aggtcttcct tgctcagaag atgataattg gacgg                  105
```

<210> SEQ ID NO 9
<211> LENGTH: 107
<212> TYPE: DNA
<213> ORGANISM: Homo sapiens

<400> SEQUENCE: 9
ggttgtcaat cacaggtcgc caggagacac cacatccagg agctgactca catctagggt      60
tggcaatctg aggagcctcc cattctccat ccatgtcttc atcccaa                  107

<210> SEQ ID NO 10
<211> LENGTH: 121
<212> TYPE: DNA
<213> ORGANISM: Homo sapiens

<400> SEQUENCE: 10
ccacattgaa cccaatggta gggatggtgg tgacgatctc ccccagtttc agcttgtata      60
ggatggtggt ctttcctgcg gcatccaggc ccaccatcag gatgcgcatc tccttcttcc     120
c                                                                     121

<210> SEQ ID NO 11
<211> LENGTH: 114
<212> TYPE: DNA
<213> ORGANISM: Homo sapiens

<400> SEQUENCE: 11
gctcgtcagt gtccaccct cctcgcaact ccaggcgctc cttttctgc tccatataga       60 gctcctgggc cattttccgg tacttccgga atcttccat catggtgcgc cttc            114

<210> SEQ ID NO 12
<211> LENGTH: 78
<212> TYPE: DNA
<213> ORGANISM: Homo sapiens

<400> SEQUENCE: 12
gggggctctg tttggtggtc tctctagctg cactggtcta tcaagctgtt ggctggtctc      60
tctctctggc tggggatc                                                    78

<210> SEQ ID NO 13
<211> LENGTH: 95
<212> TYPE: DNA
<213> ORGANISM: Homo sapiens

<400> SEQUENCE: 13
cattttgtta cataaggatg acttttttat acaatggaat aaattatggc atttctattg      60
aaatttcaac gcttttgttt ctttggcaac cacac                                 95

<210> SEQ ID NO 14
<211> LENGTH: 114
<212> TYPE: DNA
<213> ORGANISM: Homo sapiens

<400> SEQUENCE: 14
gcattacaaa gagtgttcta tgaattacag catagtgata aacctgtagg aacaaaaaag      60
ttaacaaagt catttgggtg ggaaacttta gatagcttca tgcaacatga tgtt           114

<210> SEQ ID NO 15
<211> LENGTH: 97
<212> TYPE: DNA
<213> ORGANISM: Homo sapiens

<400> SEQUENCE: 15
gccgttcttc tacttctctt tctcaagcag cagtgtcaac aggctttgcc cctccaaaga    60
tagaagcagc tcgagtggac tgggaggtac tagcaga                              97

<210> SEQ ID NO 16
<211> LENGTH: 73
<212> TYPE: DNA
<213> ORGANISM: Homo sapiens

<400> SEQUENCE: 16
gatccctggg cgcggggcag gggccggcgg aggacgggac gaggatggcg gaccgaacct    60
ggcagaggct ggg                                                        73

<210> SEQ ID NO 17
<211> LENGTH: 103
<212> TYPE: DNA
<213> ORGANISM: Homo sapiens

<400> SEQUENCE: 17
ccaagcttcc tatcttaagc tgggcgttga tatccaggtc acaactatag atgtagtgaa    60
acttctctgc ttcccccatc gcaccgtctg caaaggtacc acc                      103

<210> SEQ ID NO 18
<211> LENGTH: 145
<212> TYPE: DNA
<213> ORGANISM: Homo sapiens

<400> SEQUENCE: 18
cagttggggt gggtgtcatc aaagcagtgg acaagaaggc tgctggagct ggcaaggtca    60
ccaagtctgc ccagaaagct cagaaggcta atgaatatt atccctaata cctgccaccc    120
cactcttaat cagtggtgga agaac                                          145

<210> SEQ ID NO 19
<211> LENGTH: 173
<212> TYPE: DNA
<213> ORGANISM: Homo sapiens

<400> SEQUENCE: 19
acacacagac acacagacac agagagacac acagacacac acagagat acacagagac     60 acagacacag aaacactctg agacacacac acagacacac acagacacac acagacacag   120
agagacacac agacacacac acacagagat acacagagac acagacacag aaa           173

<210> SEQ ID NO 20
<211> LENGTH: 233
<212> TYPE: DNA
<213> ORGANISM: Homo sapiens

<400> SEQUENCE: 20
gtgccgtatg aatatacaaa ataatggcat cagggatccc tgtgctcatt cacatagcta    60
gggacaacag gatttcatct ccaggaaact cagtagtata cttttgtgac ttctctcttt   120
aagcaccaaa gcatactttc aggaaaaac aaaaaagaga ttaaaaatgt aaagaattct    180
ttcatgctgc ttggagaggt gagggaaggt agcccactga aagtgacaga gaa           233

<210> SEQ ID NO 21
<211> LENGTH: 28
<212> TYPE: DNA

```
<213> ORGANISM: Homo sapiens

<400> SEQUENCE: 21
ctcggaattc aagcttatgg atggatgg                                28

<210> SEQ ID NO 22
<211> LENGTH: 24
<212> TYPE: DNA
<213> ORGANISM: Homo sapiens

<400> SEQUENCE: 22
catccatcca taagcttgaa ttcc                                    24

<210> SEQ ID NO 23
<211> LENGTH: 27
<212> TYPE: DNA
<213> ORGANISM: Homo sapiens

<400> SEQUENCE: 23
tgagtgagtg aatcgatgga tccgtct                                 27

<210> SEQ ID NO 24
<211> LENGTH: 31
<212> TYPE: DNA
<213> ORGANISM: Homo sapiens

<400> SEQUENCE: 24
tcctagacgg atccatcgat tcactcactc a                            31

<210> SEQ ID NO 25
<211> LENGTH: 57
<212> TYPE: DNA
<213> ORGANISM: Homo sapiens

<400> SEQUENCE: 25
ggtccaccat ggccctgctg cactccggcc gcgtcctccc cgggatcgcc gccgcct   57

<210> SEQ ID NO 26
<211> LENGTH: 57
<212> TYPE: DNA
<213> ORGANISM: Homo sapiens

<400> SEQUENCE: 26
aggcggcggc gatcccgggg aggacgcggc cggagtgcag cagggccatg gtggacc    57

<210> SEQ ID NO 27
<211> LENGTH: 78
<212> TYPE: DNA
<213> ORGANISM: Homo sapiens

<400> SEQUENCE: 27
gcctgcacat gacgatatgg atgaggatga taatgtatca atgggtgggc ctgatagtcc  60
tgattcagtg gatcccgt                                              78

<210> SEQ ID NO 28
<211> LENGTH: 78
<212> TYPE: DNA
<213> ORGANISM: Homo sapiens

<400> SEQUENCE: 28
acgggatcca ctgaatcagg actatcaggc ccacccattg atacattatc atcctcatcc  60
atatcgtcat gtgcaggc                                              78
```

<210> SEQ ID NO 29
<211> LENGTH: 54
<212> TYPE: DNA
<213> ORGANISM: Homo sapiens

<400> SEQUENCE: 29
agttcctttt acttttaat ctttccttaa agcacgcctg tgttgggcta acga    54

<210> SEQ ID NO 30
<211> LENGTH: 54
<212> TYPE: DNA
<213> ORGANISM: Homo sapiens

<400> SEQUENCE: 30
tcgttagccc aacacaggcg tgctttaagg aaagattaaa agtaaaagg aact    54

<210> SEQ ID NO 31
<211> LENGTH: 77
<212> TYPE: DNA
<213> ORGANISM: Homo sapiens

<400> SEQUENCE: 31
cgacagctgc agaccttcag ccagagcctg caggagctgc tggcagaaca ttataaacat    60
cactggttcc cagaaaa    77

<210> SEQ ID NO 32
<211> LENGTH: 77
<212> TYPE: DNA
<213> ORGANISM: Homo sapiens

<400> SEQUENCE: 32
ttttctggga accagtgatg tttataatgt tctgccagca gctcctgcag gctctggctg    60
aaggtctgca gctgtcg    77

<210> SEQ ID NO 33
<211> LENGTH: 43
<212> TYPE: DNA
<213> ORGANISM: Homo sapiens

<400> SEQUENCE: 33
aacacccata gtaggcctaa aagcagccac caattaagaa agc    43

<210> SEQ ID NO 34
<211> LENGTH: 43
<212> TYPE: DNA
<213> ORGANISM: Homo sapiens

<400> SEQUENCE: 34
gctttcttaa ttggtggctg cttttaggcc tacgatgggt gtt    43

<210> SEQ ID NO 35
<211> LENGTH: 89
<212> TYPE: DNA
<213> ORGANISM: Homo sapiens

<400> SEQUENCE: 35 ggtaaggta gggcactttt aatttaaatg acttcttgca ccatcttgcc taatggacta    60
gattggactg tatcaacatt gatttactc    89

<210> SEQ ID NO 36

```
<211> LENGTH: 89
<212> TYPE: DNA
<213> ORGANISM: Homo sapiens

<400> SEQUENCE: 36
gagtaaatca atgttgatac agtccaatct agtccattag gcaagatggt gcaagaagtc      60
atttaaatta aaagtgccct acccttacc                                       89

<210> SEQ ID NO 37
<211> LENGTH: 121
<212> TYPE: DNA
<213> ORGANISM: Homo sapiens

<400> SEQUENCE: 37
tggctgggac ctttaggaaa gtgaaatgca ggtgagaaga acctaaacat gaaaggaaag      60
ggtgcctcat cccagcaacc tgtccttgtg ggtgatgatc actgtgctgc ttgtggctca     120
t                                                                     121

<210> SEQ ID NO 38
<211> LENGTH: 121
<212> TYPE: DNA
<213> ORGANISM: Homo sapiens

<400> SEQUENCE: 38
atgagccaca agcagcacag tgatcatcac ccacaaggac aggttgctgg gatcaggcac      60
cctttccttt catgtttagg ttcttctcac ctgcatttca ctttcctaaa ggtcccagcc     120
a                                                                     121

<210> SEQ ID NO 39
<211> LENGTH: 123
<212> TYPE: DNA
<213> ORGANISM: Homo sapiens

<400> SEQUENCE: 39
aagtgaaatg caggtgagaa gaacctaaac atgaaaggaa agggtgcctc atcccagcaa      60
cctgtccttg tgggtgatga tcactgtgct gcttgtggct catggcagag cattcagtgc     120
caa                                                                   123

<210> SEQ ID NO 40
<211> LENGTH: 123
<212> TYPE: DNA
<213> ORGANISM: Homo sapiens

<400> SEQUENCE: 40
ttggcactga atgctctgcc atgagccaca agcagcacag tgatcatcac ccacaaggac      60
aggttgctgg gatgaggcac cctttccttt catgtttagg ttcttctcac ctgcatttca     120
ctt                                                                   123

<210> SEQ ID NO 41
<211> LENGTH: 118
<212> TYPE: DNA
<213> ORGANISM: Homo sapiens

<400> SEQUENCE: 41
cgtttaagaa tggaaaagcg acataactat gttcggaaag tagcagagac tgctgtgcag      60
ctgtttattt ctggggacaa agtgaatgtg gctggtctag ttttagctgg atccgctc       118
```

```
<210> SEQ ID NO 42
<211> LENGTH: 118
<212> TYPE: DNA
<213> ORGANISM: Homo sapiens

<400> SEQUENCE: 42
gagcggatcc agctaaaact agaccagcca cattcacttt gtccccagaa ataaacagct        60
gcacagcagt ctctgctact ttccgaacat agttatgtcg cttttccatt cttaaacg       118

<210> SEQ ID NO 43
<211> LENGTH: 59
<212> TYPE: DNA
<213> ORGANISM: Homo sapiens

<400> SEQUENCE: 43
agtgctttaa cgatgtcaca gctatcattt acgtcgcagc ctgcagtagc tacaacatg        59

<210> SEQ ID NO 44
<211> LENGTH: 59
<212> TYPE: DNA
<213> ORGANISM: Homo sapiens

<400> SEQUENCE: 44
catgttgtag ctactgcagg ctgcgacgta aatgatagct gtgacatcgt taaagcact        59

<210> SEQ ID NO 45
<211> LENGTH: 135
<212> TYPE: DNA
<213> ORGANISM: Homo sapiens

<400> SEQUENCE: 45
ggagtgtgca cggatgctga atgtttggga atgagaggat gagtgagtga ggcttgaaaa        60
cacaccacat tgaaaatcct gccacagcag cagccgcagc cgccaacagc agcgctgtta       120
gtgagctaag taagc                                                        135

<210> SEQ ID NO 46
<211> LENGTH: 135
<212> TYPE: DNA
<213> ORGANISM: Homo sapiens

<400> SEQUENCE: 46
gcttacttag ctcactaaca gcgctgctgt tggcggctgc ggctgctgct gtggcaggat        60
tttcaatgtg gtgtgttttc aagcctcact cactcatcct ctcattccca aacattcagc       120
atccgtgcac actcc                                                        135

<210> SEQ ID NO 47
<211> LENGTH: 89
<212> TYPE: DNA
<213> ORGANISM: Homo sapiens

<400> SEQUENCE: 47
ctgggtcccc aaggagggcc agtgcaactt caggttccat atcttgttca aagccttggg        60
agaagagaag ggtggggctt ccctttcgc                                          89

<210> SEQ ID NO 48
<211> LENGTH: 89
<212> TYPE: DNA
<213> ORGANISM: Homo sapiens

<400> SEQUENCE: 48
```

```
gcgaaaggga agccccaccc ttctcttctc ccaaggcttt gaacaagata tggaacctga    60
agttgcactg gccctccttg gggacccag                                      89

<210> SEQ ID NO 49
<211> LENGTH: 181
<212> TYPE: DNA
<213> ORGANISM: Homo sapiens

<400> SEQUENCE: 49
cttcttggtg gtgttcttga gtaagataat ctggactggc cccgtctttt gcttccctgc    60
ctgctgctgc cccatttgat caagagacca tggaagtgtc agagattcag aatccaagat   120
tgtctttaag ttttcaactg taaataaagt ttttttgtat gcgtaaaaaa agctcgtgcc   180
t                                                                    181

<210> SEQ ID NO 50
<211> LENGTH: 181
<212> TYPE: DNA
<213> ORGANISM: Homo sapiens

<400> SEQUENCE: 50
aggcacgagc ttttttacg catacaaaaa aactttatt acagttgaaa acttaaagac      60
aatcttggat tctgaatctc tgacacttcc atggtctctt gatcaaatgg ggcagcagca   120
ggcagggaag caaagacggg ggccagtcca gattatctta ctcaagaaca ccaccaagaa   180
g                                                                    181

<210> SEQ ID NO 51
<211> LENGTH: 97
<212> TYPE: DNA
<213> ORGANISM: Homo sapiens

<400> SEQUENCE: 51
acagaaggag agaccgaata caaatttgaa tggcagaaag gagccccacg agaaaaatat    60
gccaaagatg acatgaacat cagagatcag cccttta                             97

<210> SEQ ID NO 52
<211> LENGTH: 97
<212> TYPE: DNA
<213> ORGANISM: Homo sapiens

<400> SEQUENCE: 52
taaagggctg atctctgatg ttcatgtcat cttTggcata ttTttctcgt ggggctcctt    60
tctgccattc aaatttgcat tcggtctctc cttctgt                             97

<210> SEQ ID NO 53
<211> LENGTH: 74
<212> TYPE: DNA
<213> ORGANISM: Homo sapiens

<400> SEQUENCE: 53
gttccacctc cagtcccgcc gcttcgacca agagatcggt cttcaacaga aaagcatgac    60
tgggatcctc caga                                                      74

<210> SEQ ID NO 54
<211> LENGTH: 74
<212> TYPE: DNA
<213> ORGANISM: Homo sapiens

<400> SEQUENCE: 54
```

```
caaggtggag gtcagggcgg cgaagctggt tctctagcca gaagttgtct tttcgtactg    60
accctcggag gtct                                                     74

<210> SEQ ID NO 55
<211> LENGTH: 141
<212> TYPE: DNA
<213> ORGANISM: Homo sapiens

<400> SEQUENCE: 55
gcagcgtgga ggagcagctg gcccagcttc gctgcgagat ggagcagcag aaccaggaat    60
acaaaatcct gctggatgtg aagacgcggc tggagcagga gattgccacc taccgccgcc   120
tgctggaggg agaggatgcc c                                             141

<210> SEQ ID NO 56
<211> LENGTH: 141
<212> TYPE: DNA
<213> ORGANISM: Homo sapiens

<400> SEQUENCE: 56
gggcatcctc tccctccagc aggcggcggt aggtggcaat ctcctgctcc agccgcgtct    60
tcacatccag caggattttg tattcctggt tctgctgctc catctcgcag cgaagctggg   120
ccagctgctc ctccacgctg c                                             141

<210> SEQ ID NO 57
<211> LENGTH: 91
<212> TYPE: DNA
<213> ORGANISM: Homo sapiens

<400> SEQUENCE: 57
tgttctgaga actgactttc tccccatccc cttcctaaat atccaaagac tgtactggcc    60
agtgtcattt tattttttcc ctcctgacaa t                                  91

<210> SEQ ID NO 58
<211> LENGTH: 91
<212> TYPE: DNA
<213> ORGANISM: Homo sapiens

<400> SEQUENCE: 58
attgtcagga gggaaaaaat aaaatgacac tggccagtac agtctttgga tatttaggaa    60
ggggatgggg agaaagtcag ttctcagaac a                                  91

<210> SEQ ID NO 59
<211> LENGTH: 120
<212> TYPE: DNA
<213> ORGANISM: Homo sapiens

<400> SEQUENCE: 59
gcttagagta tggagaacat ggatgcagaa caccagacac ccctttctct ctctttgaag    60
gaatggctgg aacaatatat ttcctggctg acctgctagt ccccacaaaa gccaggttcg   120

<210> SEQ ID NO 60
<211> LENGTH: 120
<212> TYPE: DNA
<213> ORGANISM: Homo sapiens

<400> SEQUENCE: 60
cgaacctggc ttttgtgggg actagcaggt cagccaggaa atatattgtt ccagccattc    60
```

-continued cttcaaagag agagaaaggg gtgtctggtg ttctgcatcc atgttctcca tactctaagc    120

<210> SEQ ID NO 61
<211> LENGTH: 139
<212> TYPE: DNA
<213> ORGANISM: Homo sapiens

<400> SEQUENCE: 61
agttggtatc aatggagtgg gagaggtgag gagatcacaa gaggaatttg gagcccaggg    60
tcagccctct catcctgccc aaatgttggc agaatctggg tcttagacta gcataagtga    120
agtctgggga gggccgaac                                                 139

<210> SEQ ID NO 62
<211> LENGTH: 139
<212> TYPE: DNA
<213> ORGANISM: Homo sapiens

<400> SEQUENCE: 62
gttcggccct ccccacactt cacttatgct agtctaagac ccagattctg ccaacatttg    60
ggcaggatga gagggctgac cctgggctcc aaattcctct tgtgatctcc tcacctctcc    120
cactccattg ataccaact                                                 139

<210> SEQ ID NO 63
<211> LENGTH: 125
<212> TYPE: DNA
<213> ORGANISM: Homo sapiens

<400> SEQUENCE: 63
gtacaaccag ctcctcagaa ttgaagagga gctgggcagc aaggctaagt ttgccggcag    60
gaacttcaga aacccttgg ccaagtaagc tgtgggcagg caagcccttc ggtcacctgt     120
tggct                                                                125

<210> SEQ ID NO 64
<211> LENGTH: 125
<212> TYPE: DNA
<213> ORGANISM: Homo sapiens

<400> SEQUENCE: 64
agccaacagg tgaccgaagg gcttgcctgc ccacagctta cttggccaag gggtttctga    60
agttcctgcc ggcaaactta gccttgctgc ccagctcctc ttcaattctg aggagctggt    120
tgtac                                                                125

<210> SEQ ID NO 65
<211> LENGTH: 158
<212> TYPE: DNA
<213> ORGANISM: Homo sapiens

<400> SEQUENCE: 65
tacaaccagc tcctcagaat tgaagaggag ctgggcagca aggctaagtt tgccggcagg    60
aacttcagaa acccttggc caagtaagct gtgggcaggc aagcccttcg gtcacctgtt     120
ggctacacag acccctcccc tcgtgtcagc tcaggcag                            158

<210> SEQ ID NO 66
<211> LENGTH: 158
<212> TYPE: DNA
<213> ORGANISM: Homo sapiens

<400> SEQUENCE: 66

-continued ctgcctgagc tgacacgagg ggagggtct gtgtagccaa caggtgaccg aagggcttgc    60
ctgcccacag cttacttggc caagggtttt ctgaagttcc tgccggcaaa cttagccttg   120
ctgcccagct cctcttcaat tctgaggagc tggttgta                           158

<210> SEQ ID NO 67
<211> LENGTH: 114
<212> TYPE: DNA
<213> ORGANISM: Homo sapiens

<400> SEQUENCE: 67
cccacattcc gtcacctgct cagaatcatg caggtctcca ctgctgccct tgctgtcctc    60
ctctgcacca tggctctctg caaccagttc tctgcatcac ttgctgctga cacg          114

<210> SEQ ID NO 68
<211> LENGTH: 114
<212> TYPE: DNA
<213> ORGANISM: Homo sapiens

<400> SEQUENCE: 68
cgtgtcagca gcaagtgatg cagagaactg gttgcagaga gccatggtgc agaggaggac    60
agcaagggca gcagtggaga cctgcatgat tcagagcagg tgacggaatg tggg          114

<210> SEQ ID NO 69
<211> LENGTH: 82
<212> TYPE: DNA
<213> ORGANISM: Homo sapiens

<400> SEQUENCE: 69
ctctgttctt caagtttccc tttgattgat ttcatgtaat ctttgatgta cttcttgtag    60
gcttcttttg tgaaacttgt tt                                             82

<210> SEQ ID NO 70
<211> LENGTH: 82
<212> TYPE: DNA
<213> ORGANISM: Homo sapiens

<400> SEQUENCE: 70
aaacaagttt cacaaaagaa gcctacaaga agtacatcaa agattacatc aaatcaatca    60
aagggaaact tgaagaacag ag                                             82

<210> SEQ ID NO 71
<211> LENGTH: 82
<212> TYPE: DNA
<213> ORGANISM: Homo sapiens

<400> SEQUENCE: 71
ctctgttctt caagtttccc tttgattgat ttcatgtaat ctttgatgta cttcttgtag    60
gcttcttttg tgaaacttgt tt                                             82

<210> SEQ ID NO 72
<211> LENGTH: 82
<212> TYPE: DNA
<213> ORGANISM: Homo sapiens

<400> SEQUENCE: 72
aaacaagttt cacaaaagaa gcctacaaga agtacatcaa agattacatc aaatcaatca    60
aagggaaact tgaagaacag ag                                             82

<210> SEQ ID NO 73
<211> LENGTH: 89
<212> TYPE: DNA
<213> ORGANISM: Homo sapiens

<400> SEQUENCE: 73
tcatcactga ggaagagaag aatttcaaag ccttcgctag tctccgtatg gcccgtgcca      60
acgcccggct cttcggcaca cgggcaaaa                                        89

<210> SEQ ID NO 74
<211> LENGTH: 89
<212> TYPE: DNA
<213> ORGANISM: Homo sapiens

<400> SEQUENCE: 74
ttttgcccgt gtgccgaaga gccgggcgtt ggcacgggcc atacggagac tagcgaaggc      60
tttgaaattc ttctcttcct cagtgatga                                        89

<210> SEQ ID NO 75
<211> LENGTH: 56
<212> TYPE: DNA
<213> ORGANISM: Homo sapiens

<400> SEQUENCE: 75
gattctcagc tggtagctgg tgttgcattc aagaagactt tctcttacgc tgggtt         56

<210> SEQ ID NO 76
<211> LENGTH: 56
<212> TYPE: DNA
<213> ORGANISM: Homo sapiens

<400> SEQUENCE: 76
aacccagcgt aagagaaagt cttcttgaat gcaacaccag ctaccagctg agaatc         56

<210> SEQ ID NO 77
<211> LENGTH: 114
<212> TYPE: DNA
<213> ORGANISM: Homo sapiens

<400> SEQUENCE: 77
caggttgtct ttaagatgtt cttttagaca gctgcacatt gtagaccctt tcacctgccc      60
tacaccaaag atgtacgatg cactaggaaa ctgctcatag gatttctgtc agct           114

<210> SEQ ID NO 78
<211> LENGTH: 114
<212> TYPE: DNA
<213> ORGANISM: Homo sapiens

<400> SEQUENCE: 78
agctgacaga aatcctatga gcagtttcct agtgcatcgt acatctttgg tgtagggcag      60 gtgaagggt ctacaatgtg cagctgtcta aagaacatc ttaaagacaa cctg             114

<210> SEQ ID NO 79
<211> LENGTH: 66
<212> TYPE: DNA
<213> ORGANISM: Homo sapiens

<400> SEQUENCE: 79 gagaggggg atctcatcag gaactgcagc attgggttcc tctgctgcca cttcatcttc      60
atcaat                                                                66

<210> SEQ ID NO 80
<211> LENGTH: 66
<212> TYPE: DNA
<213> ORGANISM: Homo sapiens

<400> SEQUENCE: 80

```
attgatgaag atgaagtggc agcagaggaa cccaatgctg cagttcctga tgagatcccc    60
cctctc                                                               66
```

<210> SEQ ID NO 81
<211> LENGTH: 109
<212> TYPE: DNA
<213> ORGANISM: Homo sapiens

<400> SEQUENCE: 81

```
aagccctcgg cccccaagaa gggagacagt tctgctgaag aactgaaact ggccacccag    60
ctgaccggac cggtcatgcc cgtccggaac gtctataaga aggagaaag               109
```

<210> SEQ ID NO 82
<211> LENGTH: 109
<212> TYPE: DNA
<213> ORGANISM: Homo sapiens

<400> SEQUENCE: 82

```
ctttctcctt cttatagacg ttccggacgg gcatgaccgg tccggtcagc tgggtggcca    60
gtttcagttc ttcagcagaa ctgtctccct tcttggggc cgagggctt                109
```

<210> SEQ ID NO 83
<211> LENGTH: 84
<212> TYPE: DNA
<213> ORGANISM: Homo sapiens

<400> SEQUENCE: 83

```
ggtctctgtt cttcaagttt ccctttgatt gatttcatgt atctttgatg tacttcttgt    60
aggcttcttt tgtgaaactt gttt                                           84
```

<210> SEQ ID NO 84
<211> LENGTH: 84
<212> TYPE: DNA
<213> ORGANISM: Homo sapiens

<400> SEQUENCE: 84

```
aaacaagttt cacaaaagaa gcctacaaga agtacatcaa agatacatga aatcaatcaa    60
agggaaactt gaagaacaga gacc                                           84
```

<210> SEQ ID NO 85
<211> LENGTH: 320
<212> TYPE: DNA
<213> ORGANISM: Homo sapiens

<400> SEQUENCE: 85

```
tgggggaagg gtgcagcaac gatttctcac caaatcacta cacaggacag caaaggggtg    60
agaaggggct gagggaggaa aagccaggaa actgagatca gcagagggag ccaagcatca   120
aaaaacagga gatgctgaag ctgcgatgac cagcatcatt ttcttaagag aacattcaag   180
gatttgtcat gatggctggg ctttcacttg gtgttaagtc tacaaacagc accttcaatt   240
ggaactgtca attaaagttc ttaagattta ggaagtggtg gagcttggaa agttatgaga   300
```

```
ttacaaaatt tctgaaagtc                                              320

<210> SEQ ID NO 86
<211> LENGTH: 320
<212> TYPE: DNA
<213> ORGANISM: Homo sapiens

<400> SEQUENCE: 86
gactttcaga aattttgtaa tctcataact ttccaagctc caccacttcc taaatcttaa     60
gaactttaat tgacagttcc aattgaaggt gctgtttgta gacttaacac caagtgaaag    120
cccagccatc atgacaaatc cttgaatgtt ctcttaagaa aatgatgctg gtcatcgcag    180
cttcagcatc tcctgttttt tgatgcttgg ctccctctgc tgatctcagt ttcctggctt    240
ttcctccctc agccccttct caccccttgg ctgtcctgtg tagtgatttg gtgagaaatc    300
gttgctgcac ccttccccca                                              320

<210> SEQ ID NO 87
<211> LENGTH: 123
<212> TYPE: DNA
<213> ORGANISM: Homo sapiens

<400> SEQUENCE: 87
ggaaaaaaaa aaaaactaca aaaccctaa ttttgtacat actgtatttt tactattgaa      60
ctgtattcta gtggctgttc atgctccaag actttagtta ccgagacatg aatactatcc    120
atg                                                                123

<210> SEQ ID NO 88
<211> LENGTH: 123
<212> TYPE: DNA
<213> ORGANISM: Homo sapiens

<400> SEQUENCE: 88
catggatagt attcatgtct cggtaactaa agtcttggag catgaacagc cactagaata     60
cagttcaata gtaaaaatac agtatgtaca aaattagggt ttttgtagtt ttttttttt    120 tcc                                                                123

<210> SEQ ID NO 89
<211> LENGTH: 110
<212> TYPE: DNA
<213> ORGANISM: Homo sapiens

<400> SEQUENCE: 89
ctcattttct ggactgggca gcctttgggg tcatgaccct tccctccatc ggcatccccc     60
tgctattgtg gtactccagc aagaggaaat atgacactcc caaaacgaag               110

<210> SEQ ID NO 90
<211> LENGTH: 110
<212> TYPE: DNA
<213> ORGANISM: Homo sapiens

<400> SEQUENCE: 90
cttcgttttg ggagtgtcat atttcctctt gctggagtac cacaatagca gggggatgcc     60
gatggaggga aggtcatga ccccaaaggc tgcccagtcc agaaaatgag                110

<210> SEQ ID NO 91
<211> LENGTH: 90
<212> TYPE: DNA
<213> ORGANISM: Homo sapiens
```

<400> SEQUENCE: 91

| aatcattgtt | tttccttttg | taaatgttga | ttcagaaaag | gaaagcacag | gctaagcagt | 60 |
| tgaaggttcc | ccaccattca | gtgagagcag | | | | 90 |

<210> SEQ ID NO 92
<211> LENGTH: 90
<212> TYPE: DNA
<213> ORGANISM: Homo sapiens

<400> SEQUENCE: 92

| ctgctctcac | tgaatggtgg | ggaaccttca | actgcttagc | ctgtgctttc | cttttctgaa | 60 |
| tcaacattta | caaggaaaa | aacaatgatt | | | | 90 |

<210> SEQ ID NO 93
<211> LENGTH: 103
<212> TYPE: DNA
<213> ORGANISM: Homo sapiens

<400> SEQUENCE: 93

| tcgggagccg | cggcttatgg | tgcagacatg | gccaagtcca | agaaccacac | cacacacaac | 60 |
| cagtcccgaa | aatggcacag | aaatggtatc | aagaaacccc | gat | | 103 |

<210> SEQ ID NO 94
<211> LENGTH: 103
<212> TYPE: DNA
<213> ORGANISM: Homo sapiens

<400> SEQUENCE: 94

| atcggggttt | cttgatacca | tttctgtgcc | attttcggga | ctggttgtgt | gtggtgtggt | 60 |
| tcttggactt | ggccatgtct | gcaccataag | ccgcggctcc | cga | | 103 |

<210> SEQ ID NO 95
<211> LENGTH: 82
<212> TYPE: DNA
<213> ORGANISM: Homo sapiens

<400> SEQUENCE: 95

| cgggagccgc | ggcttatggt | gcagacatgg | ccaagtccaa | gaaccacacc | acacacaacc | 60 |
| agtcccgaaa | atggcacaga | aa | | | | 82 |

<210> SEQ ID NO 96
<211> LENGTH: 82
<212> TYPE: DNA
<213> ORGANISM: Homo sapiens

<400> SEQUENCE: 96

| tttctgtgcc | attttcggga | ctggttgtgt | gtggtgtggt | tcttggactt | ggccatgtct | 60 |
| gcaccataag | ccgcggctcc | cg | | | | 82 |

<210> SEQ ID NO 97
<211> LENGTH: 22
<212> TYPE: DNA
<213> ORGANISM: Homo sapiens

<400> SEQUENCE: 97

| tagggctcga | gccgccacca | tg | 22 |

<210> SEQ ID NO 98

```
<211> LENGTH: 22
<212> TYPE: DNA
<213> ORGANISM: Homo sapiens

<400> SEQUENCE: 98
atccctgcag gtcactcact ca                                              22

<210> SEQ ID NO 99
<211> LENGTH: 67
<212> TYPE: DNA
<213> ORGANISM: Homo sapiens

<400> SEQUENCE: 99
ggaactccag gtagaatttg gtctgggact tggtcttcaa tgtggcatag cacctgagaa     60
actcaat                                                               67

<210> SEQ ID NO 100
<211> LENGTH: 67
<212> TYPE: DNA
<213> ORGANISM: Homo sapiens

<400> SEQUENCE: 100
attgagtttc tcaggtgcta tgccacattg aagaccaagt cccagaccaa attctacctg     60
gagttcc                                                               67

<210> SEQ ID NO 101
<211> LENGTH: 98
<212> TYPE: DNA
<213> ORGANISM: Homo sapiens

<400> SEQUENCE: 101
aggcggagag gatcatgtcc gggaactgcg ggtagtagc gatctgggtt acccagccgt      60
tgtggccctt gagggtgcca cgaagggtca tctgctca                             98

<210> SEQ ID NO 102
<211> LENGTH: 98
<212> TYPE: DNA
<213> ORGANISM: Homo sapiens

<400> SEQUENCE: 102
tgagcagatg acccttcgtg gcaccctcaa gggccacaac ggctgggtaa cccagatcgc     60 tactacccg cagttcccgg acatgatcct ctccgcct                              98

<210> SEQ ID NO 103
<211> LENGTH: 172
<212> TYPE: DNA
<213> ORGANISM: Homo sapiens

<400> SEQUENCE: 103
atactttaat tttaaatttt cttcttgtaa ctgctccaaa ttcggagaag ctcctaaaca     60
gccacagttt ttcaaccggt caatttcagc agtcagagat ttaatctctt cttcctgctg    120
cagcagccgc gcggagcact cagacatcag tacgtccatc ctcccatcag cg            172

<210> SEQ ID NO 104
<211> LENGTH: 172
<212> TYPE: DNA
<213> ORGANISM: Homo sapiens

<400> SEQUENCE: 104
cgctgatggg aggatggacg tactgatgtc tgagtgctcc gcgcggctgc tgcagcagga     60
```
agaagagatt aaatctctga ctgctgaaat tgaccggttg aaaaactgtg gctgtttagg      120
agcttctccg aatttggagc agttacaaga agaaaattta aaattaaagt at              172

<210> SEQ ID NO 105
<211> LENGTH: 107
<212> TYPE: DNA
<213> ORGANISM: Homo sapiens

<400> SEQUENCE: 105
tttgtcgact ggcctaggtg caggtggttg gtaggctcat ccaggagcag catgaagggc      60
cgaataaaga gggctctggc aagggcaacc ctcatcctcc agctcac                    107

<210> SEQ ID NO 106
<211> LENGTH: 107
<212> TYPE: DNA
<213> ORGANISM: Homo sapiens

<400> SEQUENCE: 106
gtgagctgga ggatgagggt tgcccttgcc agagccctct ttattcggcc cttcatgctg      60
ctcctggatg agcctaccaa ccacctgcac ctaggccagt cgacaaa                    107

<210> SEQ ID NO 107
<211> LENGTH: 295
<212> TYPE: DNA
<213> ORGANISM: Homo sapiens

<400> SEQUENCE: 107
tttgtcgacc gtttctgtgc agaaagggct ctggagagat gttcatagca gcacacacct      60
gcggctcttc ttcggttctg gaggctccag ggcagccaat attgcttcgt caaatacatt     120
ctttaggcct ttctgtgtaa gtgcagaaca ctccacatac ttgacagcct tcaggtcacg     180
ggccagcttt tcagcagtct ctggagtgat aggcttctgt tgttcttgg caagtttctc      240 aatagtagag gggtcatctc tgagatcaat ttgagtccca acaagcaagt cgaca          295

<210> SEQ ID NO 108
<211> LENGTH: 295
<212> TYPE: DNA
<213> ORGANISM: Homo sapiens

<400> SEQUENCE: 108
tgtcgacttg cttgttggga ctcaaattga tctcagagat gacccctcta ctattgagaa      60
acttgccaag aacaaataga agcctatcac tccagagact gctgaaaagc tggcccgtga     120
cctgaaggct gtcaagtatg tggagtgttc tgcacttaca cagaaaggcc taagaatgt      180 atttgacgaa gcaatattgg ctgccctgga gcctccagaa ccgaagaaga gccgcaggtg     240
tgtgctgcta tgaacatctc tccagagccc tttctgcaca gaaacggtcg acaaa         295

<210> SEQ ID NO 109
<211> LENGTH: 188
<212> TYPE: DNA
<213> ORGANISM: Homo sapiens

<400> SEQUENCE: 109
tttgtcgaca tcgccttctt catttggaac ttggttgtgg acttcacctc atccactttg      60
gccaccatgt tttcgttgtg tgtgagcagg gaagggaact ttcctgcctt atttagacct     120
gggccgagga ttcgtggaat ctgcttgatc agagactctg aggccaaaaa cgcatcatac     180

```
ttcttggt                                                                188
```

<210> SEQ ID NO 110
<211> LENGTH: 188
<212> TYPE: DNA
<213> ORGANISM: Homo sapiens

<400> SEQUENCE: 110

```
accaagaagt atgatgcgtt tttggcctca gagtctctga tcaagcagat tccacgaatc     60
ctcggcccag gtctaaataa ggcaggaaag ttcccttccc tgctcacaca caacgaaaac    120
atggtggcca aagtggatga ggtgaagtcc acaaccaagt tccaaatgaa gaaggcgatg    180
tcgacaaa                                                            188
```

<210> SEQ ID NO 111
<211> LENGTH: 170
<212> TYPE: DNA
<213> ORGANISM: Homo sapiens

<400> SEQUENCE: 111

```
tttctcgctt gtattcctga agatgagttt ggccctgtga ctctgaaggg tcggctatta     60
actgagacat cctctgtcgg gttgccccccc gtgttatatt tcgccatgag ggactttaca   120
tctgcctttc catcctacaa acatagggaa caaaaaatag ctgagagaca               170
```

<210> SEQ ID NO 112
<211> LENGTH: 170
<212> TYPE: DNA
<213> ORGANISM: Homo sapiens

<400> SEQUENCE: 112

```
tgtctctcag ctattttttg ttccctatgt ttgtaggatg gaaaggcaga tgtaaagtcc     60
ctcatggcga aatataacac gggggcaac ccgacagagg atgtctcagt taatagccga    120
cccttcagag tcacagggcc aaactcatct tcaggaatac aagcgagaaa               170
```

<210> SEQ ID NO 113
<211> LENGTH: 127
<212> TYPE: DNA
<213> ORGANISM: Homo sapiens

<400> SEQUENCE: 113

```
gccggtggct cacatggcct gtctgcactg taaccacagg ctgggatgta gccaggactt     60
ggtctccttg gaagacaggt ctgatgtttg gccaatccag tccttcagac cctgtctgaa   120
acttgta                                                            127
```

<210> SEQ ID NO 114
<211> LENGTH: 127
<212> TYPE: DNA
<213> ORGANISM: Homo sapiens

<400> SEQUENCE: 114

```
tacaagtttc agacagggtc tgaaggactg gattggccaa acatcagacc tgtcttccaa     60
ggagaccaag tcctggctac atcccagcct gtggttacag tgcagacagg ccatgtgagc   120
caccggc                                                            127
```

<210> SEQ ID NO 115
<211> LENGTH: 79
<212> TYPE: DNA
<213> ORGANISM: Homo sapiens

```
<400> SEQUENCE: 115
gtcgaccttc ctctttaccg tccaccagct cacacagtgg ggtagctggc tgctgaggca    60
attccacaat ggtttctct                                                 79

<210> SEQ ID NO 116
<211> LENGTH: 79
<212> TYPE: DNA
<213> ORGANISM: Homo sapiens

<400> SEQUENCE: 116
agagaaacca ttgtggaatt gcctcagcag ccagctaccc cactgtgtga gctggtggac    60
ggtaaagagg aaggtcgac                                                 79

<210> SEQ ID NO 117
<211> LENGTH: 68
<212> TYPE: DNA
<213> ORGANISM: Homo sapiens

<400> SEQUENCE: 117
tttaaaggga cagcttcgaa gacatttcca tctggtatac ttcactagtt agcaatgccc    60
aggaatgc                                                             68

<210> SEQ ID NO 118
<211> LENGTH: 68
<212> TYPE: DNA
<213> ORGANISM: Homo sapiens

<400> SEQUENCE: 118
gcattcctgg gcattgctaa ctagtgaagt ataccagatg gaaatgtctt cgaagctgtc    60
cctttaaa                                                             68
```

COMPOSITIONS AND METHODS FOR INHIBITING HUMAN IMMUNODEFICIENCY VIRUS INFECTION BY DOWN-REGULATING HUMAN CELLULAR GENES

CROSS-REFERENCE TO RELATED APPLICATIONS

This application is related to International Application No. PCT/US98/11452, filed Jun. 2, 1998 and U.S. patent application Ser. No. 09/087,609 filed May 29, 1998, and further to U.S. patent application Ser. No. 08/867,314, filed Jun. 2, 1997, now U.S. Pat. No. 6,071,743. Each of the patent applications referred to in this section is incorporated by reference herein in its entirety.

FIELD OF THE INVENTION

The present invention relates to the identification of certain human genes as cellular targets for the design of therapeutic agents for suppressing human immunodeficiency virus (HIV) infection. These genes encode products that are necessary for HIV infection, because HIV infection is inhibited when expression of these genes is down-regulated. Therefore, compounds that inhibit expression of these genes or inhibit function of the encoded gene products can be used as therapeutic agents for the treatment and/or prevention of HIV infection. In addition, the invention relates to methods for identifying additional cellular genes as therapeutic targets for suppressing HIV infection, and methods of using such cellular genes and their encoded products in screening assays for selecting protective compounds that inhibit HIV infection. The present invention also includes a method to prevent tumorigenesis.

BACKGROUND OF THE INVENTION

The primary cause of acquired immunodeficiency syndrome (AIDS) has been shown to be HIV (Barre-Sinoussi et al., 1983, Science 220:868–870; Gallo et al., 1984, Science 224:500–503). HIV causes immunodeficiency in an individual by infecting important cell types of the immune system, which results in their depletion. This, in turn, leads to opportunistic infections, neoplastic growth and death.

HIV is a member of the lentivirus family of retroviruses (Teich et al., 1984, RNA Tumor Viruses, Weiss et al., eds., CSH-Press, pp. 949–956). Retroviruses are small enveloped viruses that contain a diploid, single-stranded RNA genome, and replicate via a DNA intermediate produced by a virally-encoded reverse transcriptase, an RNA-dependant DNA polymerase (Varmus, 1988, Science 240:1427–1439). There are at least two distinct subtypes of HIV: HIV-1 (Barre-Sinoussi et al., ibid.; Gallo et al., ibid.) and HIV-2 (Clavel et al., 1986, Science 233:343–346; Guyader et al., 1987, Nature 326:662–669). Genetic heterogeneity exists within each of these HIV subtypes.

CD4$^+$ T cells are the major targets of HIV infection because the CD4 cell surface protein acts as a cellular receptor for HIV attachment (Dalgleish et al., 1984, Nature 312:763–767; Klatzmann et al., 1984, Nature 312:767–768; Maddon et al., 1986, Cell 47:333–348). Viral entry into cells is dependent upon viral protein gp120 binding to the cellular CD4 receptor molecule (McDougal et al., 1986, Science 231:382–385; Maddon et al., 1986, Cell 47:333–348).

HIV infection is pandemic and HIV-associated diseases have become a world-wide health problem. Despite considerable efforts in the design of anti-HIV modalities, there is, thus far, no successful prophylactic or therapeutic regimen against AIDS. However, several stages of the HIV life cycle have been considered as potential targets for therapeutic intervention (Mitsuya et al., 1991, FASEB J. 5:2369–2381). For example, virally-encoded reverse transcriptase has been a major focus of drug development. A number of reverse-transcriptase-targeted drugs, including 2N,3N-dideoxynucleotide analogs such as AZT, ddI, ddC, and ddT have been shown to be active against HIV (Mitsuya et al., 1990, Science 249:1533–1544). While beneficial, these nucleotide analogs are not curative, probably due to the rapid appearance of drug resistant HIV mutants (Lander et al., 1989, Science 243:1731–1734). In addition, these drugs often exhibit toxic side effects, such as bone marrow suppression, vomiting, and liver abnormalities.

Another stage of the HIV life cycle that has been targeted is viral entry into cells, the earliest stage of HIV infection. This approach has primarily utilized recombinant soluble CD4 protein to inhibit infection of CD4$^+$ T cells by some HIV-1 strains (Smith et al., 1987, Science 238:1704–1707). Certain primary HIV-1 isolates, however, are relatively less sensitive to inhibition by recombinant CD4 (Daar et al., 1990, Proc. Natl. Acad. Sci. USA 87:6574–6579). To date, clinical trials of recombinant, soluble CD4 have produced inconclusive results (Schooley et al., 1990, Ann. Int. Med. 112:247–253; Kahn et al., 1990, Ann. Int. Med. 112:254–261; Yarchoan et al., 1989, Proc. Vth Int. Conf. on AIDS, p. 564, MCP 137).

Additionally, the later stages of HIV replication (which involve crucial virus-specific processing of certain viral proteins and enzymes) have been targeted for anti-HIV drug development. Late-stage processing is dependent on the activity of a virally-encoded protease, and drugs including saquinavir, ritonavir, and indinavir have been developed to inhibit this protease (Pettit et al., 1993, Persp. Drug Discov. Design 1:69–83). With this class of drugs, the emergence of drug resistant HIV mutants is also a problem; resistance to one inhibitor often confers cross-resistance to other protease inhibitors (Condra et al., 1995, Nature 374:569–571). Also, these drugs often exhibit toxic side-effects such as nausea, altered taste, circumoral parethesias, fat deposits, diarrhea and nephrolithiasis.

Antiviral therapy of HIV using different combinations of nucleoside analogs and protease inhibitors have recently been shown to be more effective than the use of a single drug alone (Torres et al., 1997, Infec. Med. 14:142–160). However, despite the ability to achieve significant decreases in viral burden, there is no evidence to date that combinations of available drugs will afford a curative treatment for AIDS.

Other potential approaches for developing treatment for AIDS include the delivery of exogenous genes into infected cells. One such gene therapy approach involves the use of genetically-engineered viral vectors to introduce toxic gene products to kill HIV-infected cells. Another form of gene therapy is designed to protect virally-infected cells from cytolysis by specifically disrupting viral replication. Stable expression of RNA-based (decoys, antisense and ribozymes) or protein-based (transdominant mutants) HIV-1 antiviral agents can inhibit certain stages of the viral life cycle. A number of anti-HIV suppressors have been reported, such as decoy RNA of TAR or RRE (Sullenger et al., 1990, Cell 63:601–608; Sullenger et al., 1991, J. Virol. 65:6811–6816; Lisziewicz et al., 1993, New Biol. 3:82–89; Lee et al., 1994, J. Virol. 68:8254–8264), ribozymes (Sarver et al., 1990, Science 247:1222–1225; Weerasinghe et al., 1991, J. Virol. 65:5531–5534; Dropulic et al., 1992, J. Virol. 66:1432–1441; Ojwang et al., 1992, Proc. Natl. Acad. Sci.

USA 89:10802–10806; Yu et al., 1993, *Proc. Natl. Acad. Sci. USA* 90:6340–6344; Yu et al., 1995, *Proc. Natl. Acad. Sci. USA* 92:699–703; Yamada et al., 1994, *Gene Therapy* 1:38–45), antisense RNA complementary to the mRNA of viral gag, tat, rev or env genes (Sezakiel et al., 1991, *J. Virol.* 65:468–472; Chatterjee et al., 1992, *Science* 258:1485–1488; Rhodes et al., 1990, *J. gen. Virol.* 71:1965. Rhodes et al., 1991, *AIDS* 5:145–151; Sezakiel et al., 1992, *J. Virol.* 66:5576–5581; Joshi et al., 1991, *J. Virol.* 65:5524–5530) and transdominant mutants including Rev (Bevec et al., 1992, *Proc. Natl. Acad. Sci. USA* 89:9870–9874), Tat (Pearson et al., 1990, *Proc. Natl. Acad. Sci. USA* 87:5079–5083; Modesti et al., 1991, *New Biol.* 3:759–768), Gag (Trono et al., 1989, *Cell* 59:113–120), Env (Bushschacher et al., 1995, *J. Virol.* 69:1344–1348) and protease (Junker et al., 1996, *J. Virol.* 70:7765–7772).

Antisense polynucleotides have been designed to complex with and sequester the HIV-1 transcripts (Holmes et al., WO 93/11230; Lipps et al., WO 94/10302; Kretschmer et al., EP 594,881; and Chatterjee et al., 1992, *Science* 258:1485). Furthermore, an enzymatically active RNA, termed ribozyme, has been used to cleave viral transcripts. The use of a ribozyme to generate resistance to HIV-1 in a hematopoietic cell line has been reported (Ojwang et al., 1992, *Proc. Natl. Acad. Sci. USA* 89:10802–06; Yamada et al., 1994, *Gene Therapy* 1:38–45; Ho et al., WO 94/26877; and Cech and Sullenger, WO 95/13379). In preclinical studies, RevM10, a transdominant Rev protein, has been transfected ex vivo into CD4⁻ cells of HIV-infected individuals and shown to confer survival advantage over cells transfected with vector only (Woffendin et al., 1996, *Proc. Natl. Acad. Sci. USA* 93:2889–2894).

Despite enormous efforts in the art, reliable, curative anti-HIV therapeutic agents and regimens have not been developed.

In nature, evolution of an intracellular pathogen such as HIV requires the development of interactions of its genes and gene products with multiple cellular components. For instance, the interactions of a virus with a host cell involves binding of the virus to a specific cellular receptor(s), translocation through the cellular membrane, uncoating, replication of the viral genome, transcription of the viral genes, etc. Each of these events occurs in a cell and involves interactions with a cellular component. Thus, the life cycle of a virus can be completed only if the cell is "permissive" for viral infection. Availability of amino acids and nucleotides for replication of the viral genome and protein synthesis, energy status of the cell, the presence of cellular transcription factors and enzymes all contribute to the propagation of the virus in the cell. Consequently, the cellular components, in part, determine host cell susceptibility to infection, and can be used as potential targets for the development of new therapeutic interventions. In the case of HIV, one cellular component that has been used towards this end is the cell surface molecule for HIV attachment, CD4.

Recently, it was reported that HIV entry into a susceptible cell requires the expression of a second type of receptor, the chemokine receptors (CCR2, CCR3, CCR5 or CXCR4), in addition to CD4 (Moore, 1997, *Science* 276:51–52). A chemokine receptor normally binds RANTES, MIP-1α and MIP-1β as its natural ligand. In the case of HIV infection, it has been proposed that CD4 first binds to the HIV gp120 protein on the cell surface followed by binding of this complex to a chemokine receptor, resulting in viral entry into the cells (Cohen, 1997, *Science* 275:1261). Therefore, chemokine receptors can present an additional cellular target for the design of HIV therapeutic agents. Inhibitors of HIV/chemokine receptor interactions are being tested as anti-HIV agents. However, there remains a need for the discovery of additional cellular targets for the design of anti-HIV therapeutics, particularly intracellular targets for disrupting viral replication after viral entry into a cell.

It also has been reported that overexpression of the hdm2 protein drives oncogenesis through antagonism of the p53 tumor suppressor protein. Binding of hdm2 to p53 promotes the degradation of p53. Several recent reports focus on the requirement for the hdm2 protein to actively shuttle between nucleus and cytoplasm in order to exert inhibition of p53 (Lain et al., 1999, *Exp. Cell Res.* 248:457–472). An inhibitor of nuclear export activates the p53 response and induces the localization of HDM2 and p53 to U1A-positive nuclear bodies associated with the PODs (Roth et al., 1998, *EMBO J.* 15:554–564). Nucleo-cytoplasmic shuttling of the hdm2 oncoprotein regulates the levels of the p53 protein via a pathway also used by the human immunodeficiency virus rev protein (Tao et al., 1999, *Proc. Natl. Acad. Sci. USA* 96:3077–3080). P19(ARF) stabilizes p53 by blocking nucleo-cytoplasmic shuttling of Mdm2 (Tao et al., 1999, *Proc. Natl. Acad. Sci. USA* 96:6937–6941). Thus, shuttling of the hdm2 protein apparently depends on a nuclear export pathway that overlaps, or is identical to, that utilized by the HIV rev protein. Furthermore, the P19 (ARF) tumor suppressor stabilizes p53, thereby inhibiting tumorigenesis, by interfering with this nucleo-cytoplasmic shuttling.

Thus, there remains a need to isolate and identify genetic suppressor elements and cellular target genes that are involved in the inhibition of HIV infection or tumorigenesis.

SUMMARY OF THE INVENTION

The present invention relates to compositions and methods for inhibiting HIV infection by down-regulating expression of certain human cellular genes and/or inhibiting the activity of products encoded by such genes. In particular, it relates to a number of human cell-derived nucleic acid molecules which inhibit HIV infection in susceptible cells. The isolated nucleic acid molecules correspond to portions of cellular genes or complements thereof, and are referred to herein as genetic suppressor elements (GSEs). The cellular genes encode intracellular products necessary for productive HIV infection. Additionally, small molecule inhibitors of the same cellular genes and their encoded products are also within the scope of the present invention. The invention also relates to methods for identifying additional cellular genes as therapeutic targets for suppressing HIV infection, and methods for using such cellular genes and their encoded products for selecting additional inhibitors of HIV.

The invention is based, in part, on the Applicants' discovery that nucleic acid molecules isolated from human cells can prevent both the activation of latent HIV-1 in a CD4⁺ cell line and productive HIV infection in such cells, and that such nucleic acid molecules correspond to fragments of certain human cellular genes. In that regard, any cellular or viral marker associated with HIV infection can be used to select for such nucleic acid molecules. An example of such a marker is CD4, which is conveniently monitored by using a specific antibody.

Based on substantial sequence identity (90%–100%), a number of the isolated GSEs correspond to portions of human cellular genes that encode different subunits of a mitochondrial enzyme complex, NADH dehydrogenase. In addition, inhibitors of this enzyme also inhibit HIV infection in susceptible host cells, including freshly isolated human CD4⁺ T cells. Furthermore, additional GSEs have been selected that have substantial sequence identity (90%–100%) with the following cell-derived nucleic acid molecules: 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin-related protein, p18 protein, p40 protein, glucosidase II, alpha enolase, macrophage inflammatory protein 1 alpha, tumor protein translationally-controlled 1 (TCTP1), BBC1, Nef interacting protein, Na$^+$-D-glucose cotransport regulator gene protein, hsp90 chaperone protein, FK506-binding protein A1, Rox, beta signal sequence receptor, tumorous imaginal disc protein, cell surface heparin binding protein, SH2-containing inositol 5-phosphatase (referred to herein as SHIP), guanine nucleotide binding protein beta polypeptide 2-like 1 (referred to herein as GNB2L1), arginyl tRNA synthetase (referred to herein as ArgRS), ABC transporter, cell division cycle 42 GTP-binding protein (referred to herein as CDC42), cyclosporin-A 19 (referred to herein as Csa-19), src kinase p59 (referred to herein as FYN), cathepsin B (referred to herein as CTSB), cathepsin L and glutaredoxin (referred to herein as GLRX).

Among the GSEs selected to inhibit HIV infection, several function in the sense orientation, while others function in the antisense orientation. Not intending to be bound by any particular theory, the GSEs of the invention are believed to down-regulate a cellular gene by different mechanisms. The GSEs are expressed in a host cell by encoding RNA molecules that do or do not encode protein products. GSEs in the sense orientation can exert their effects as transdominant mutants or RNA decoys. Transdominant mutants are expressed proteins or peptides that competitively inhibit the normal function of a wild-type protein in a dominant fashion. RNA decoys are protein binding sites that titrate out these proteins. GSEs in the antisense orientation can exert their effects as antisense RNA; i.e. nucleic acid molecules complementary to the mRNA of the target gene. These nucleic acid molecules bind to mRNA and block the translation of the mRNA. Some antisense nucleic acid molecules can act directly at the DNA level to inhibit transcription. The down-regulation of a cellular gene by a GSE, in turn, removes a cellular component necessary for, for example HIV replication, resulting in an inhibition of HIV infection.

A wide range of uses are encompassed by the invention including, but not limited to, HIV treatment and prevention by transferring protective GSE compounds as inhibitory compositions into HIV-susceptible cell types. For example, GSEs can be transferred into T cells, particularly CD4$^+$ T cells that are the major cell population targeted by HIV. Alternatively, GSEs can be transferred into hematopoietic stem cells in vitro followed by their engraftment in an autologous or histocompatible or even histoincompatible recipient. In another embodiment, any cells susceptible to HIV infection can be directly transduced or transfected with GSEs in vivo. In yet another embodiment, inhibitors of NADH dehydrogenase, 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, Na$^+$-D-glucose cotransport regulator gene protein, hsp90 chaperone protein, FK506-binding protein A1, Rox, beta signal sequence receptor, tumorous imaginal disc protein, cell surface heparin binding protein, SH2-containing inositol 5-phosphatase (SHIP), guanine nucleotide binding protein beta polypeptide 2-like 1 (GNB2L1), arginyl tRNA synthetase (ArgRS), ABC transporter, cell division cycle 42 GTP-binding protein (CDC42), cyclosporin-A 19 (Csa-19), src kinase p59 (FYN), cathepsin B (CTSB), cathepsin L and glutaredoxin (GLRX) can be used as inhibitory compositions in vivo to suppress or prevent HIV infection.

after infection with HIV-1$_{SF2}$ at a TCID$_{50}$ of 1000. Controls include mock-infected, vector (LNGFRM)-infected and CEM-ss cells transfected with RevM10.

Figure 9:
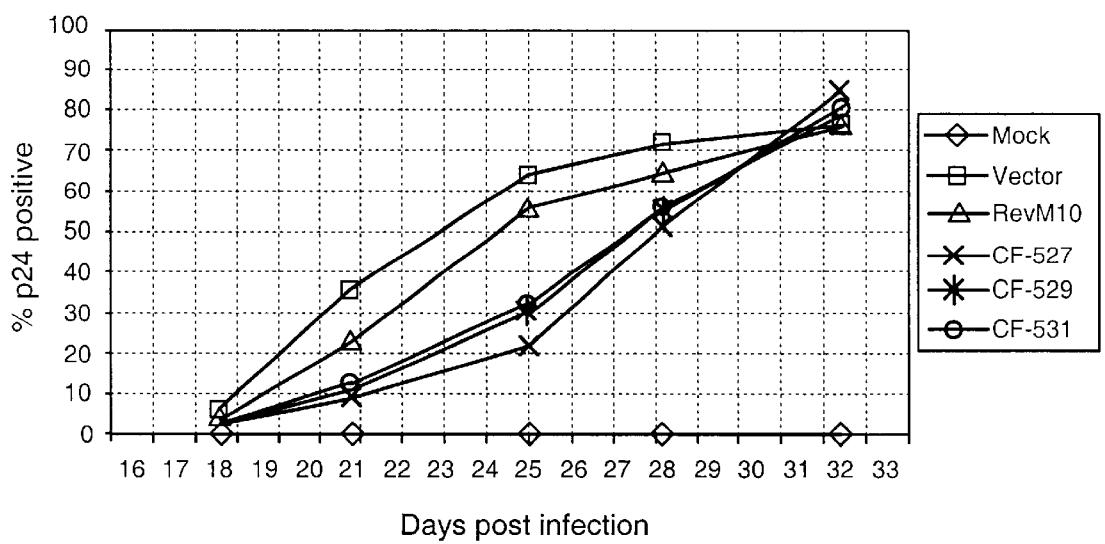

FIG. 9 illustrates the percentage of intracellular p24$^+$ CEM-ss cells containing various GSEs: CF-619 (SEQ ID NO:53), CF-620 (SEQ ID NO:55) and CF-624 (SEQ ID NO:57) after infection with HIV-1$_{SF2}$ at a TCID$_{50}$ of 1000. Controls include mock-infected, vector (LNGFRM)-infected and CEM-ss cells transfected with RevM10.

DETAILED DESCRIPTION OF PREFERRED EMBODIMENTS

The present invention includes novel methods to identify genetic suppressor elements capable of inhibiting HIV infection, genetic suppressor elements identified by such methods, nucleic acid molecules representing host cellular genes involved in HIV infection and inhibitory compositions that inhibit HIV infection by down-regulating the expression of such cellular genes or inhibit the activity of the products of such cellular genes. As used herein, the term "HIV infection" refers to the ability of HIV to enter a host cell and/or replicate in the host cell. The present invention also relates to nucleic acid molecules and proteins that prevent tumorigenesis and methods to use such nucleic acid molecules and proteins. According to the present invention, the cell-derived proteins and cell-derived nucleic acid molecules disclosed herein may also inhibit tumorigenesis, as well as HIV infection. As such, it is intended that the functional definitions of protein and nucleic acid homologs and protective compounds include the function of preventing tumorigenesis.

One embodiment of the present invention is a method for isolating genetic suppressor elements, referred to herein as GSEs, comprising the steps of: 1) randomly fragmenting cell-derived cDNA into fragments; 2) inserting the fragments into expression vectors to form a random fragment expression (RFE) library; 3) transferring the expression library into a population of cells containing an inducible latent HIV-1 provirus or susceptible to HIV infection; 4) selecting a subpopulation of cells which contain a subset of the expression library enriched for GSEs by monitoring the expression of a cellular or viral marker associated with HIV infection; and 5) recovering the GSEs from the selected cell population. In preferred embodiments, the cell-derived cDNA is randomly-fragmented into 100–700 base pair (bp) fragments. The method further includes repetition of the aforementioned steps so that many rounds of successive selection can be performed. The method can further comprise the step of selecting GSEs by determining the continued expression of a cellular marker such as CD4 or the decreased expression of a viral marker such as p24 or gp120 using, for example, an antibody.

The invention is discussed in more detail in the subsections below, solely for purposes of description and not by way of limitation. For clarity of discussion, the specific procedures and methods described herein are exemplified using OM10.1 cells, CEM-ss cells, tumor necrosis factor-alpha (TNF-α), an anti-CD4 antibody, and an anti-p24 antibody, but they are merely illustrative for the practice of the invention. Analogous procedures and techniques are equally applicable to isolating GSEs from other cellular DNA, utilizing any cell line and any marker associated with HIV infection that can be easily assayed.

A cell-derived RFE library can be constructed from nucleic acid molecules of any mammalian cells preferably from cDNA of HIV-susceptible cells. In that regard, Example 1 demonstrates that GSEs can be selected from HL-60 cells that are naturally susceptible to HIV infection and from HeLa cells which are not naturally susceptible to HIV infection due to the lack of CD4 expression. However, it has been shown that expression of CD4 on the surface of HeLa cells by means of a retoviral vector renders the cells susceptible to HIV infection. Therefore, cell types not normally susceptible to HIV infection can still be useful as a source of genetic material for the construction of RFE libraries. It is also preferred that a normalized cDNA library is prepared (Gudkov and Roninson, 1996, *Methods is Molecular Biology* 69:229–231). DNA is first treated with enzymes to produce randomly cleaved fragments. This can be conveniently performed by DNase I cleavage in the presence of Mn$^{++}$ (Roninson et al., U.S. Pat. No. 5,217,889, column 5, lines 5–20). Thereafter, the randomly-cleaved DNA is size fractionated by gel electrophoresis. Fragments of between 100 and 700 bp are the preferred lengths for constructing RFE libraries. Single strand breaks of the size-selected fragments are repaired by methods well known in the art.

The fragments are ligated with 5' and 3' adaptors, which are selected to have non-cohesive restriction sites so that each fragment can be inserted into an expression vector in an oriented fashion. Further, the 5' adaptor contains a start (ATG) codon to allow the translation of the fragments which contain an open reading frame in the correct phase. The fragments are then inserted into appropriate expression vectors. Any expression vector that results in efficient expression of the fragments in host cells can be used. In a preferred embodiment viral-based vectors such as the retroviral vectors LNCX (Miller and Rosman, 1989, *BioTechniques* 7:980) and LNGFRM are exemplified. Alternatively, adenovirus, adeno-associated virus and herpes virus vectors can also be used for this purpose.

When viral-based vectors are used, the ligated vectors are first transfected into a packaging cell line to produce viral particles. For retroviral vectors, any amphotropic packaging line such as PA317 (Miller and Buttimore, 1986, *Mol. Cell. Biol.* 6:2895–2902; ATCC CRL #9078) can be used to efficiently produce virus. In a preferred embodiment of the invention, the viral vector also contains a selectable gene, such as the neo$^r$ gene or a truncated nerve growth factor receptor (NGFR) gene, which allows isolation of the cells that contain the vector.

The number of independent clones present in each RFE expression library can vary. In a preferred embodiment, libraries of cell-derived cDNA of about $10^6$ to $10^8$ independent clones can be used.

In a specific embodiment illustrated by way of example in Example 1, OM10.1 cells are used to select for GSEs, and are maintained in conventional tissue culture as described in Butera, U.S. Pat. No. 5,256,534. The purpose of using OM10.1 cells for the selection of GSEs is that they contain a latent HIV-1 provirus which is inducible by TNF-α. Other cell lines can be similarly engineered with an inducible HIV provirus. Examples of cell lines that are infected with latent HIV include, but are not limited to, U1, U33, 8E5, ACH-2, LL58, THP/HIV and UHC4 (Bednarik and Folks, 1992, *AIDS* 6:3–16). A variety of agents have been shown to be capable of inducing latent HIV-infected cells, and these include TNF-α, TNF-β, interleukins-1, -2, -3, -4 and -6, granulocyte-macrophage colony stimulating factors, macrophage-colony stimulating factors, interferon-α, transforming growth factor-β, PMA, retinoic acid and vitamin D3 (Poli and Fauci, 1992, *AIDS Res. Human Retroviruses* 9:191–197). Alternatively, GSEs can be selected on the basis of their ability to directly protect HIV-susceptible cells from HIV infection using methods described herein.

The cell-derived RFE library can be introduced into latently HIV-infected cells or HIV-susceptible cells by any technique well known in the art that is appropriate to the vector system employed. In one embodiment of the invention, the viral vector also contains a selectable marker in addition to a random fragment of cellular DNA. A suitable marker is the $neo^r$ gene, which permits selection of cells containing RFE library members using the drug G-418. In a preferred embodiment, the viral vector contains a truncated low affinity nerve growth factor receptor (NGFR) that permits selection of the cells using an anti-NGFR monoclonal antibody. In alternative embodiments, the multiplicity of infection of the virions of the library is adjusted so that pre-selection for cells that are transduced by the vector is not needed.

In the case of OM10.1 cells, the transduced cell population is treated with 10 U/mL TNF-α for a period of 24–72 hours and preferably about 24 hours according to the method of Butera. The activation of the latent HIV-1 provirus in OM10.1 can be detected by the suppression of the cell surface CD4. (It is believed that viral protein gp120 binds to CD4 in the cytoplasm, which prevents subsequent expression of CD4 on the cell surface.) Clones that are resistant to HIV replication continue to express cell surface CD4. Such clones can be selected, for example, by cell sorting using any antibody staining technique for CD4 and a fluorescence activated cell sorter (FACS).

The fraction of $CD4^+$ cells that have been transduced with the RFE library can be compared with cells transduced with an expression library consisting of the vector only. An increased relative difference between the cell-derived RFE library and the control library can be found with each additional round of TNF-α induction. Thus, in the preferred embodiment of the invention there are at least two cycles of induction, selection and recloning before the GSEs are recovered from the cells for further characterization.

After selection, specific nucleic acid molecules corresponding to the GSEs can be recovered from cells that continue to express CD4 following induction of the latent HIV provirus by TNF-α. The specific GSEs are recovered from genomic DNA isolated from $CD4^+$ cells sorted by FACS after TNF-α induction. The GSEs in this population are preferably recovered by PCR amplification using primers designed from the sequences of the vector.

The recovered GSEs can be introduced into an expression vector as discussed in the Examples section herein. The resultant GSEs expression library is known as a secondary library. The secondary library can utilize the same or a different vector from that used for the construction of the primary library. The secondary library can be transduced into another cell population and the resultant population selected, recloned and processed as described herein.

Additionally, each individually recovered GSE can be inserted into cloning vectors for determining its specific nucleotide sequence and its orientation. The sequence of the GSE is then compared with sequences of known genes to determine the portion of the cellular gene with which it corresponds. Alternatively, the PCR products themselves can be directly sequenced to determine their nucleotide sequences. Concurrently, the isolated GSEs can be analyzed to determine their minimal core sequences. A core sequence is a common sequence found by comparison of GSEs with overlapping sequences. The GSEs are further tested for their ability to protect previously uninfected cells from HIV infection.

Another embodiment of the present invention includes a method for determining the core sequence of a GSE. This can be done by comparing overlapping sequences of independently derived GSEs. Alternatively, GSEs can be altered by additions, substitutions or deletions and assayed for retention of HIV-suppressive function. Alterations in the GSEs sequences can be generated using a variety of chemical and enzymatic methods which are well known to those skilled in the art. For example, oligonucleotide-directed mutagenesis can be employed to alter the GSE sequence in a defined way and/or to introduce restriction sites in specific regions within the sequence. Additionally, deletion mutants can be generated using DNA nucleases such as Bal 31 or Exo III and S1 nuclease. Progressively larger deletions in the GSE sequences can be generated by incubating the DNA with nucleases for increased periods of time (see Ausubel, et al., ibid., for a review of mutagenesis techniques).

The altered sequences can be evaluated for their ability to suppress expression of HIV proteins such as p24 in appropriate host cells. It is within the scope of the present invention that any altered or shortened GSE nucleic acid molecules that retain their ability to suppress HIV infection can be incorporated into recombinant expression vectors for further use.

In order to confirm that the selected GSEs can protect uninfected cells from HIV infection, the GSEs can be transferred into latently HIV infected or into HIV-susceptible host cells followed by HIV infection. In this connection, GSEs also can be directly selected from a RFE library for their ability to prevent productive infection by HIV, as shown in a specific embodiment exemplified in the Examples section herein. Protection experiments can be performed in any cell type that takes up the potential GSEs and that is otherwise susceptible to HIV infection. In a preferred embodiment by way of example, the CEM-ss cell line is used (Foley et al. 1965, *Cancer* 18:522–529). The use of CEM-ss cells as targets for quantitative infectivity of HIV-1 has been described by Nara & Fischinger (1988, *Nature* 322:469–470). Other cell lines that are susceptible to HIV infection include, but are not limited to, HUT-78, H19, Jurkat E6-1, A3.01, U-937, AA-2, HeLa $CD4^+$ and C8166. In addition, freshly isolated peripheral blood leukocytes can be used.

The test of the potential GSEs can be performed using the same expression vector system as that employed in the RFE library transduction of cells during initial selection steps. In other embodiments, the vector system can be modified to achieve higher levels of expression, e.g., the linkers can be employed to introduce a leader sequence that increases the translational efficiency of the message. One such sequence is disclosed by Kozak, 1994, *Biochemie* 76:815–821.

Another way of testing the effectiveness of a potential GSE against HIV infection is to determine how rapidly HIV-1 variants develop that can negate the effects of that element. Such a test includes infection of a culture of susceptible cells such as CEM-ss cells at a low multiplicity of infection and repeatedly assaying the culture to determine whether and how quickly HIV-1 infection becomes widespread. The range of useful multiplicities of infection is between about 100 to 1000 tissue culture infectious units ($TCID_{50}$, per $10^6$ CEM-ss cells. The $TCID_{50}$ is determined by an endpoint method and is important for determining the input multiplicity of infection (moi).

A parameter that correlates with the development in the test culture of HIV-1 strains that are resistant to the effects of the potential GSEs is the fraction of cells that are infected in the culture. This fraction can be determined by immunofluorescent staining with an antibody specific for the HIV-1 p24 antigen of fixed permeabilized cells. Commercially available reagents are suitable for performing such tests (Lee et al., 1994, *J. Virol.* 68:8254–8264).

One embodiment of the present invention is an isolated nucleic acid molecule comprising a human cellular gene, or at least a portion thereof, that is necessary for HIV infection. These isolated nucleic acid molecules are referred to herein as "cell-derived nucleic acid molecules." It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives or hybrids of either DNA or RNA. An isolated nucleic acid molecule of the present invention can be obtained from its natural source either as an entire (i.e., complete) gene or a portion thereof corresponding to at least a portion of the gene that encodes a product necessary for productive HIV infection or necessary to inhibit HIV infection. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence necessary for HIV infection. An isolated nucleic acid molecule of the present invention can also be produced using recombinant DNA technology (e.g., polymerase chain reaction (PCR) amplification, cloning) or chemical synthesis. Isolated nucleic acid molecules of the present invention include natural nucleic acid molecules and homologs thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to promote HIV infection or inhibit HIV infection.

A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

One embodiment of a cell-derived nucleic acid molecule is a GSE nucleic acid molecule that is capable of inhibiting HIV infection in a susceptible cell. A preferred GSE nucleic acid molecule of the present invention comprises a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69; SEQ ID NO:71; SEQ ID NO:73; SEQ ID NO:75; SEQ ID NO:77, SEQ ID NO:79, SEQ ID NO:81, SEQ ID NO:83, SEQ ID NO:85; SEQ ID NO:87; SEQ ID NO:89; SEQ ID NO:91; SEQ ID NO:93, SEQ ID NO:95, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112 and/or SEQ ID NO:114, as well as complements of any of these sequences, homologs thereof, or nucleotide sequences capable of hybridizing to these sequences or their complements under highly or moderately stringent hybridization conditions. Also included are GSEs with conservative nucleotide substitutions which produce the same protein products. Highly stringent hybridization conditions can be defined as hybridization to filter-bound DNA in 0.5 M NaHPO$_4$, 7% sodium dodecyl sulfate (SDS), 1 mM EDTA at 65° C., followed by washing in 0.1×SSC/0.1% SDS at 68° C. (Ausubel F. M. et al., eds, 1989, Current Protocols in Molecular Biology, Vol. I, Green Publishing Associates, Inc., and John Wiley & Sons, Inc., New York at p. 2.10.3). Moderately stringent conditions can be defined as hybridizations carried out as described above, followed by washing in 0.2×SSC/0.1% SDS at 42° C. (Ausubel el al., 1989, Current Protocols for Molecular Biology).

Another embodiment of a cell-derived nucleic acid molecule of the present invention comprises a cellular gene that encodes an intracellular product necessary for productive HIV infection, referred to herein as a "target gene." Preferably, a target gene of the present invention comprises a nucleic acid molecule that corresponds to a GSE having a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:25, SEQ ID NO:27, SEQ ID NO:29, SEQ ID NO:31, SEQ ID NO:33, SEQ ID NO:35, SEQ ID NO:37,SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69; SEQ ID NO:71; SEQ ID NO:73; SEQ ID NO:75; SEQ ID NO:77, SEQ ID NO:79, SEQ ID NO:81, SEQ ID NO:83, SEQ ID NO:85; SEQ ID NO:87; SEQ ID NO:89; SEQ ID NO:91; SEQ ID NO:93, SEQ ID NO:95, SEQ ID NO:96, SEQ ID NO:98, SEQ ID NO:100, SEQ ID NO:102, SEQ ID NO:104, SEQ ID NO:106, SEQ ID. NO:108, SEQ ID NO:110, SEQ ID NO:112 and/or SEQ ID NO:114, and complements thereof, and any other GSE sequence disclosed herein and their complements.

Particularly preferred GSE nucleic acid molecules of the present invention include plasmids CF-315, CF-319, CF-101, CF-117, CF-025, CF-128, CF-004, CF-113, CF-204, CF-001, CF-273, CF-311, CF-313, CF-210, CF-266, CF-302, CF-317, CF-286, CF-061, CF-280, CF-537, CF-320, CF-321, CF-322, CF-332, CF-335, CF-42, CF-50, CF-527, CF-528, CF-529, CF-531, CF-545, CF-547, CF-619, CF-620, CF-624, CF-630, CF-579, CF-676, CF-675, CF-653, CF-674, CF-675, CF-673, CF-693, CF-287, CF-658, CF-672, CF-679, CF-681, CF-622, CF-683, CF-684, CF-685, CF-686, H1C-11H9, H1C-16A3, H1C-2F9, H1C-13D2, H1C-4A8, H1C-6G11, H1C-16E3, H1C-23G2, H1C-37E1, and/or H1C-6G5, as defined and identified herein.

As used herein, the term "corresponds to refers a nucleic acid sequence that is at least about 75%, more preferably about 80%, more preferably about 85%, more preferably about 90%, more preferably about 95% and more preferably about 100% identical to nucleic acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69; SEQ ID NO:71; SEQ ID NO:73; SEQ ID NO:75; SEQ ID NO:77, SEQ ID NO:79, SEQ ID NO:81, SEQ ID NO:83, SEQ ID NO:85; SEQ ID NO:87; SEQ ID NO:89; SEQ ID NO:91; SEQ ID NO:93, SEQ ID NO:95, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112 and/or SEQ ID NO:114, and complements thereof. The lack of complete identity between the GSEs and the target gene sequences can result from genetic polymorphism between different individuals or mutations introduced during cloning or PCR amplification.

A preferred embodiment of the present invention includes a target gene that encodes at least a portion a protein selected from the group consisting of NADH dehydrogenase, 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, $Na^+$-D-glucose cotransport regulator gene protein, hsp90 chaperone protein, FK506-binding protein A1, Rox, beta signal sequence receptor, tumorous imaginal disc protein, cell surface heparin binding protein, SHIP, GNB2L1, ArgRS, ABC Transporter, CDC42, Csa-19, FYN, CTSB, cathepsin L or GLRX, in which the portion of the nucleic acid molecule encodes an intracellular product that is necessary for HIV infection.

The subsections below describe such cellular genes that have been identified herein as important targets for the development of HIV therapeutics.

In aerobic organisms, adenosine triphosphate (ATP) provides the major source of energy. For the generation of ATP, energy rich molecules such as NADH and $FADH_2$ are first formed in glycolysis, fatty acid oxidation and the citric acid cycle. When these molecules donate their electrons to molecular oxygen, free energy is released to generate ATP.

Oxidative phosphorylation is the process by which ATP is formed as electrons are transferred from NADH or $FADH_2$ to $O_2$ by a series of electron carriers (Stryer, 1988, *Biochemistry*, Freeman). This process occurs in the mitochondria of eukaryotic cells. More specifically, the enzymes that catalyze the electron transport chain reside in the inner membrane of mitochondria, and they are encoded by both nuclear and mitochondrial DNA. These enzymes exist as large protein complexes, and the first complex of the chain is known as NADH dehydrogenase or NADH-Q reductase. It has a molecular weight of 850,000 daltons and consists of over 40 polypeptide subunits, seven of which are encoded by the mitochondrial genome. (Anderson et al., 1981, *Nature* 290:457; Chomyn et al., 1985, *Nature* 314:592; Chomyn et al., 1986, *Science* 234:619). The nucleotide sequences of the cDNAs of nuclear genes for the subunits have been described (Walker et al., 1992, *J. Mol. Biol.* 226:1051; Fearnley et al., 1989, *EMBO J.* 8:665; Pilkington et al., 1989, *Biochem.* 28:3257). NADH dehydrogenase catalyzes the transfer of electrons from NADH to an electron carrier termed ubiquinone.

The 2-oxoglutarate dehydrogenase complex catalyzes oxidative decarboxylation of 2-oxoglutarate to succinyl-CoA and $CO_2$, and is the rate-limiting enzyme which controls the flux of substrates through the Krebs cycle (Delvin, T. M., ed, 1992, *Textbook of Biochemistry*, Wiley-Liss, Inc.). This enzyme complex is located in the inner membrane/matrix compartment of the mitochondria. The complex consists of multiple copies of 2-oxoglutarate dehydrogenase (lipoamide) (OGDH or ELO; 2-oxoglutarate:lipoamide 2-oxidoreductase (decarboxylating and acceptor succinylating), EC 1.2.4.2), dihydrolipoamide succinyl-transferase (designated E20; EC 2.3.1.61) and dihydrolipoamide dehydrogenase (E3; EC 1.8.1.4). The coding sequence of 2-oxoglutarate dehydrogenase has been described (GenBank Accession Nos. D10523 and D90499; Koike et al., 1992, *Proc. Natl. Acad. Sci. USA* 89:1963–1967; Koike, 1995, *Gene* 159:261–266).

Pyruvate kinase/thyroid hormone binding protein p58 (TBP) is a monomer of pyruvate kinase (ATP pyruvate $O_2$-phosphotransferase, EC 2.7.1.40) subtype M2. Its conversion to the tetrameric pyruvate kinase is regulated by fructose 1,6,-bisphosphate (Fru-1,6-$P_2$). At low glucose concentrations mammalian cells contain low Fru-1,6-$P_2$ and pyruvate kinase is inactive. At high glucose concentration (regular medium contains 5–10 mM glucose), high levels of Fru-1,6-$P_2$ are found in proliferating and tumor cells, which require high pyruvate kinase activity for growth. It has been demonstrated that low Fru-1,6-$P_2$ favors formation of p58 and high concentrations convert it to the tetrameric enzyme. An increase in glucose concentration could lead to multimerization of p58 which in turn activates pyruvate kinase and glycolysis. At the same time thyroid hormone is released from the complex with TBP and might bind to nuclear and mitochondrial receptors and activate oxidative phosphorylation. The coding sequence of pyruvate kinase/thyroid hormone binding protein has been described (GenBank Accession No. M26252; Kato et al., 1989, *Proc. Natl. Acad. Sci. USA* 86:7861–7865).

Calnexin is a type I membrane protein which functions as a molecular chaperon for secretory glycoproteins in the endoplasmic reticulum (ER) with ATP and $Ca^{++}$ as two cofactors involved in the substrate binding (Ou et al., 1995, *J. Biol. Chem.* 270:18051). It has been demonstrated that folding of gp120 is mediated by calnexin during the translocation of the newly synthesized gp120 into ER (Li et al., 1996, *Proc. Natl. Acad. Sci. USA* 93:9606). The coding sequence of calnexin has been described (GenBank Accession No. L10284; David et al., 1993, *J. Biol. Chem.* 268:9585–9592).

ADP-ribosylation factors (ARFs) are guanine nucleotide binding proteins of about 20 kDa molecular weight that stimulate ADP-ribosyltransferase activity of cholera toxin in vitro (Tsai et al., 1991, *J. Biol. Chem.* 266:23053–23059). Five different ARFs from human cDNA have been cloned. ARF3 is represented by two MRNAs of 3.7 and 1.2 kb that are generated through the use of alternative polyadenylation signals (Tsai et al., 1991, supra).

Ubiquitin-specific protease (USP) plays an important role in several cellular processes, including the regulation of gene expression, control of the cell cycle, DNA repair and differentiation (Hochtrasser, 1995, *Curr. Opin. Cell. Biol.* 7:215–223; Wilkinson, 1995, *Ann. Rev. Nutr.* 15:161–189). One of the best characterized ubiquitin-dependent pathways involved in the control of gene expression is activation of NF-κB. Cleavage of p105, a precursor of the p50 subunit of NF-κB requires ubiquitin conjugation (Palombella et al., 1994, *Cell* 78:773–785) and secondly the destruction of IκB (a process which allows NF-κB to migrate to the nucleus in an active form) requires ubiquitination of the inhibitor in a phosphorylation-dependent manner (Scherer et al., 1995, *Proc. Natl. Acad. Sci. USA* 92:11259–11263).

USP is characterized by the presence of two conserved active site domains and has been shown to cleave ubiquitin from model substrates (Everett et al., 1997, *EMBO J.* 16: 556–577). There are two classes of USP. The first includes proteins involved in the generation of free ubiquitin from precursor fusion proteins or from peptide-linked polyubiquitin after proteolysis of the substrate by the proteosome (Hochstrasser, 1995 ibid.). The second comprises an increasing number of de-ubiquitinating proteins which can recognize and stabilize specific substrates by removing ubiquitin adducts. Examples of this class include the Drosophila fat facets protein, whose de-ubiquitination is required for proper eye development (Huang et al., 1995, *Science* 270:1828–1831). Another example is the DUB-1 gene which is an immediate early gene that regulates cell growth (Zhu et al., 1996, *Proc. Natl. Acad. Sci. USA* 93:3275–3279).

The coding sequence for herpesvirus-associated ubiquitin-specific protease has been described (GenBank accession No. Z72499; Everett et al., 1997, *EMBO J.* 16:566–577).

CD44 is a broadly distributed surface receptor glycoprotein implicated in multiple physiologic cellular functions, such as extracellular matrix-cell adhesion, lymphocyte homing, lympho-hematopoiesis, T cell activation, and tumor metastasis (Shimuzu et al., 1989, *J. Immunol.* 143:2457–2463; Huet el al., 1989, *J. Immunol.* 143:798–801). Some of these functions depend on the ability of CD44 to recognize the extracellular matrix component hyaluronic acid. CD44 is expressed as several different isoforms, varying between 85 to 200 kDa, depending on differential usage of 10 exons encoding a portion of the extracellular domain and cell type specific glycosylation. Each isoform can display some degree of functional uniqueness (Stamenkovich et al., 1989, *Cell* 56:1057–1062). The most widely expressed molecule is the 85–90 kDa glycoprotein, commonly referred to as CD44H, which has been demonstrated to be the major receptor for hyaluronic acid (Bartolazzi et al., 1996, *J. Cell Biol.* 132:1199–1208). CD44H represents the principle isoform found on hematopoietic cells. It has been shown that CD44, along with other HIV receptors like CD4, can play a role in viral tropism and affects infectivity of the virus. HIV causes CD44 down-modulation in monocytes, but on a post-translational level (Guo and Hildreth, 1993, *J. Immunol.* 151:2225–2236).

The coding sequence for human CD44 has been described (GenBank accession No. X55150; Stamenkovich et al., 1991, *EMBO J.* 10:243–248).

Phosphorylation of serine, threonine and tyrosine residues is one of the significant regulatory mechanisms in gene expression and post-translational modifications. Tyrosine phosphorylation is important in the control of normal cellular processes such as cell proliferation and differentiation, as well as pathological events such as malignant transformation (Cantley et al., 1991, *Cell* 64:281–301). The overall levels of tyrosine phosphorylation are modulated by the complementary and antagonistic actions of protein tyrosine kinases and protein tyrosine phosphatases. In the steady state, less that 1% of the total cellular phosphorylation is due to tyrosine phosphorylation. However, the phosphotyrosine content can increase dramatically upon cellular transformation (Walton and Dixon, 1993, *Ann. Rev. Biochem.* 62:101–120). There are about 40 known phosphatases (Zolnierowiez and Hemmings, 1994, *Trends Cell Biol.* 4:61–64).

Several viruses are known to contain protein tyrosine kinases and phosphatases. A putative protein tyrosine phosphatase is found in the HIV-1 5'LTR (Nandi and Banerjee, 1995, *Med. Hypothesis* 45:476–480). Phosphorylation plays an important role in tat-mediated transactivation (Ensoli et al., 1990, *Nature* 345:84–86), nef protein function (Balliet et al., 1994, *Virology* 200:623–631; Venkatesh et al., 1990, *Virology* 176:39–47), and viral matrix assembly (Camaur et al., 1997, *Virology* 71:6834–6841).

The coding sequence of protein tyrosine phosphatases from Brain Derived Phosphatase (BDP1) mRNA and CL 100 mRNA have been described (GenBank accession No. X79568; Kim et al., 1996, *Oncogene* 13:2275–2279 and GenBank accession No. X68277; Keyse and Emslie, 1992, *Nature* 359:644–647).

Phosphatidylinositol 3-kinases (PI3K) have been characterized as enzymes involved in receptor signal transduction. Multiple forms with different substrate specificities exist. They have been associated with a diverse range of cell surface receptors including those for growth factors, thrombin, chemotactic peptides and cytokines. It has been proposed that PI3Ks act as second messengers, possibly via the activation of certain protein kinase C isotypes (Liscovitch and Cantley, 1994, *Cell* 77:329–334; Toker et al., 1994, *J. Biol. Chem.* 269:323598–32367). PI3K can also play a role in the regulation of protein trafficking from the Golgi to the lysosome (Volinia et al., 1995, *EMBO J.* 14:3339–3348).

HIV-1 nef expression severely impairs PI3K association with a receptor suggesting that Nef selectively affects the PI3K signaling pathway resulting in adverse effects on host cell function (Graziani et al., 1996, *J. Biol. Chem.* 271:6590–6593). Nef expression is also accompanied by a decrease in basal intracellular PIK, suggesting a role for PI3K in HIV replication (Garcia, 1997, *C. R. Acad. Sci. III*

320:505–508). PI3K can be activated by gp160 and also has been implicated in Tat-mediated apoptosis (Mazerolles et al., 1997, Eur. J. Immunol. 27:2457–2465; Borgatti et al., 1997, Eur. J. Immunol. 27:2805–2811). Known inhibitors of PI3K include wortmannin and theophylline.

The coding sequence of phosphatidylinositol 3-kinase has been described (GenBank accession No. Z46973; Volinia et al., 1995, EMBO J. 14:3339–3348).

Elongation of the polypeptide chain occurs following initiation of translation. Elongation factors utilized the energy released by GTP hydrolysis to ensure selection of the proper aminoacyl-tRNA and to move the message and associated tRNAs through the decoding region of the ribosome (Devlin, ed, 1992, Textbook of Biochemistry, Wiley-Liss, Inc.). EF-1-α is an evolutionarily conserved universal cofactor of protein synthesis in all living cells. It carries aminoacyl-tRNAs to the A-site of the ribosome in GTP-dependent manner.

The expression levels of EF-1-α are regulated in various stages of cell life such as growth arrest, transformation and aging. Levels of EF-1α can be a key regulator in modulating the rate of apoptosis. Reduction of EF-1-α expression decelerates apoptosis while overexpression accelerates the process (Duttaroy et al., 1998, Exp. Cell Res. 238:168–176).

The coding sequence for human EF-1-α has been described (GenBank accession No. J04617; Uetsuki et al., 1989, J. Biol. Chem. 264:5791–5798).

Initiation of translation occurs by the binding of the 40S ribosomal subunit at or near the cap structure of mRNA followed by ribosome scanning of the 5' untranslated region until an initiator AUG is encountered. This process is promoted by a complex group of proteins known as initiation factors. These factors participate only in initiation of translation (Devlin, ed, 1992, Textbook of Biochemistry, Wiley-Liss, Inc.).

Eukaryotic initiation factor 3 (eIF3) is the largest multi-subunit complex involved in initiation of protein synthesis. It has a mass of 600 kDa and 10 subunits. The factor prevents association of ribosomal subunits, stabilizes methionyl-tRNA binding to the 40S subunits and promotes mRNA binding (Merrick and Hershey, 1996, in Translational Control, Hershey, Mathews and Sonenberg eds, pp31–69, Cold Spring Harbor, Cold Spring Harbor, N.Y.). The sequence for human eukaryotic initiation factor 3 has been described (GenBank accession No. U78525).

Eukaryotic initiation factor 4B (eIF4B) is an 80 kDa polypeptide that is essential for the binding of mRNA to ribosomes. eIF4B has RNA binding activity, stimulates ATPase and RNA helicase (Mehot et al., 1996, RNA 2:38–50; Abramson et al., 1987, J. Biol. Chem. 262:3826–3832; Ray et al., 1985, J. Biol. Chem. 260:7651–7658; Rozen et al., 1990, Mol. Cell. Biol. 10:1134–1144). Additionally, eIF4B has been reported to have RNA annealing activity, promoting base pairing between complementary sequences in RNA strands (Altmann et al., 1995, EMBO J. 14:3820–3827). It also interacts with eIF4A and eIF3 (Methot et al., 1996, Mol. Cell. Biol. 16:5328–5334). Overproduction of eIF4B results in a general inhibition of translation (Milburn et al., 1990, EMBO J. 9:2783–2790).

The sequence for human eIF4B has been described (GenBank accession No. X55733; Milburn et al., 1990, EMBO J. 9:2783–2790).

Protein extracts derived from bone can initiate the process that begins with cartilage formation and ends in de novo bone formation. The protein extract is referred to as bone morphogenic protein (BMP). It is not known what are the critical components of BMP that direct cartilage and bone formation, and constitutive elements supplied by the animal during cartilage and bone formation (Wozney et al., 1988, Science 242:1528–1534). Amino acid sequence has been derived from a highly purified preparation of BMP from bovine bone. Human complementary DNA clones corresponding to three polypeptides present in a BMP preparation have been isolated, and expression of the recombinant human proteins have been obtained. Each of the three expressed human proteins, BMP-1, BMP-2A, and BMP-3, appears to be independently capable of inducing the formation of cartilage in vivo. BMP-2A and BMP-3 are new members of the TGF-beta supergene family, while the third, BMP-1, is a regulatory molecule.

Human and mouse homologs of the rad21 gene of Schizosaccharomyces pombe (which is involved in the repair of ionizing radiation-induced DNA double-strand breaks) have been described (McKay et al., 1996, Genomics 36:305–315). The predicted amino acid sequences of mHR21(sp) (mouse homolog of Rad21, S. pombe) and hHR21(sp) (human homolog of Rad21, S. pombe) were 96% identical, whereas the human and S. pombe proteins were 25% identical and 47% similar. RNA blot analysis showed that mHR21 sp mRNA was abundant in all adult mouse tissues examined, with the highest expression in testis and thymus. In addition to a 3.1 kb constitutive mRNA transcript, a 2.2 kb transcript was present at a high level in postmeiotic spermatids, while expression of the 3.1 kb mRNA in testis was confined to the meiotic compartment. hHR21sp mRNA was cell cycle regulated in human cells, increasing in late S phase and peaking in G2 phase. In situ hybridization showed that mHR21sp resided on chromosome 15D3, whereas hHR21sp localized to the syntenic 8q24 region. Elevated expression of mHR21sp in testis and thymus indicates a role for the rad21 mammalian homologs in V(D)J immunoglobulin gene and meiotic recombination, respectively. Cell cycle regulation of rad21, conserved in S. pombe and humans, is consistent with a conservation of function between S. pombe and human rad21 genes.

Small GTP-binding proteins of the ras superfamily are important for exocytosis from eukaryotic cells. These GTP-binding proteins can exist in two different conformations, depending on whether they are bound to GDP or GTP, and function as molecular switches that regulate a variety of cellular processes. The GTP-GDP cycle is controlled by accessory proteins that promote the exchange of bound GDP or the hydrolysis of GTP. cDNA encoding a mammalian GDP releasing protein, mss4, has been cloned (Burton et al., 1993, Nature 361:464–467). Mss4 is a guanine nucleotide exchange factor that specifically binds to and promotes GDP-GTP exchange on a subset of the Rab GTPases (Burton et al., 1994, EMBO J. 13:5547–5558). The Mss4 protein also stimulates GDP release from Ypt1 and from the mammalian protein Rab3a, but not from Ras2. Mss4 shows sequence similarity to Dss4, a yeast protein with similar biochemical properties.

The product of the B-cell translocation gene 1 (BTG1), a member of an antiproliferative protein family including Tis-21/PC3 and Tob, regulates cell cycle progression (Rodier et al., 1999, Exp Cell Res. 249:337–348). The BTG1 gene locus has been shown to be involved in a t(8;12)(q24;q22) chromosomal translocation in a certain B-cell chronic lymphocytic leukemia (Rouault et al., 1992, EMBO J. 11:1663–1670). The cDNA for BTG1 was isolated (Rouault et al., ibid.) and contains an open reading frame of 171 amino acids. BTG1 expression is maximal in the G0/G1 phases of the cell cycle and is down-regulated when cells progress throughout G1. Furthermore, transfection experiments of NIH3T3 cells indicate that BTG1 negatively regulates cell proliferation. The BTG1 open reading frame is 60% homologous to PC3, an immediate early gene induced by nerve growth factor in rat PC12 cells. Sequence and Northern blot analyzes indicate that BTG1 and PC3 are not cognate genes. Triiodothyronine (T3) or 8-Br-cAMP increases BTG1 nuclear accumulation in confluent myoblast cultures (Rodier et al., ibid.). It has been demonstrated that AP-1 activity, a crucial target involved in the truiodothyronine myogenic influence, repressed BTG1 expression, thus explaining the low BTG1 expression level in proliferating myoblasts. An AP-1-like sequence located in the BTG1 promoter was shown to be involved in the negative regulation of BTG-1 expression.

The mouse and human lymphocyte-specific protein 1 (LSP1) genes are expressed in normal B cells and T cells, including Thy1+ thymocytes and in normal macrophages and neutrophils (Pulford et al., 1999, *Immunology* 96:262–271). LSP1 is found in all hematopoietic cells, and its function is unclear. In intact cells, mitogen-activated protein kinase-activated protein (MAPKAP) kinase 2 is rapidly activated by various cytokines, stresses, and chemotactic factors. Recently, it was shown that LSP1 is a substrate for MAPKAP kinase 2 inhuman neutrophils (Zu et al., 1996, *Blood* 87:5287–5296). LSP1 was also identified as one of the major substrates of protein kinase C in B cells (Carballo et al., 1996, *J. Immunol.* 156:1709–1713).

Protein phosphatases can control the activity of various protein kinases. Protein phosphatase 2A (PP2A) regulates cell growth and division. Investigators have suggested that HIV infection activates protein phosphatase 2A (Han et al., 1992, *J. Virol.* 66:4065–4072). Protein from other viruses are known to interact with PP2A. SV40 small tumor antigen (small-t) was used as a model to identify structural elements involved in the interaction between regulatory proteins and PP2A (Mateer et al., 1998, *J. Biol. Chem.* 273: 35339–35346). NCp7 and Vpr form a tight complex which becomes a more potent activator of PP2A than NCp7 alone. The ability of NCp7 to activate protein PP2A is regulated by Vpr. The C-terminal portion of Vpr prevents NCp7 from activating protein PP2A while the N-terminal portion of Vpr potentiates the effect of NCp7 on the activity of PP2A. These findings indicate that Vpr acts as a targeting subunit which directs NCp7 to activate protein PP2A (Tung et al., 1997, *FEBS Lett.* 401:197–201).

The reaction catalysed by squalene synthetase (SQS) shows many similarities to that performed by another polyisoprene synthase, phytoene synthetase (PhS). By identifying sequences conserved between yeast SQS (ySQS) and PhS, a 2 kb cDNA (hSQS) encoding human SQS, a protein of 417 amino acids with a predicted M(r) of 48,041 was cloned (Summers et al., 1993, *Gene* 136:185–192). Two hSQS mRNA species of 2.0 and 1.55 kb have been identified which differ in their 3' untranslated sequences. The two mRNAs are present in roughly equal amounts in heart, placenta, lung, liver, kidney and pancreas, but the 2 kb mRNA predominates in brain and skeletal muscle. In HepG2 cells, both mRNAs are induced 2-fold to 4-fold by the 3-hydroxy-3-methylglutaryl-coenzyme A reductase inhibitor, lovastatin. In contrast, Northern blot analysis of rat tissues reveals only a 2.0 kb mRNA, which is considerably up-regulated in vivo by lovastatin.

The termination of protein synthesis in ribosomes is governed by termination codons in messenger RNAs and by polypeptide chain release factors (RFs). Amino acid sequences of members of the eRF1 family are highly conserved. These RF proteins are directly implicated in the termination of translation in eukaryotes (Frolova et al., 1994, *Nature* 372: 701–703).

Prokaryotic and eukaryotic cells incorporate the amino acid selenocysteine at a UGA codon, which conventionally serves as a termination signal. Translation of eukaryotic selenoprotein mRNA requires a nucleotide selenocysteine insertion sequence in the 3'-untranslated region. Erb-1 can recognize a selenocysteine insertion sequence element.

It has also been demonstrated that eRF1 associates with the catalytic subunit of protein phosphatase 2A (Andjelkovic et al., 1996, *EMBO J.* 15:7156–67). It was postulated that eRF1 also functions to recruit PP2A into polysomes, thus bringing the phosphatase into contact with putative targets among the components of the translational apparatus. It was also demonstrated that retinoic acid induction of granulocyte differentiation of HL60 cells results a transient and reversible interconversion of phosphatase 2A holoenzyme and that the C-terminus of PP2A catalytic subunit is transiently methylated in S phase of HL-60 cells (Zhu, 1997, *Arch Biochem Biophys.* 339:210–217).

G-proteins are a family of heterotrimeric guanine nucleotide-binding proteins that play important roles in signal transduction and whose expression is regulated in a tissue-specific manner. G(olf) alpha is a G-protein originally believed to mediate signal transduction exclusively within the olfactory neuroepithelium and subsequently found to be a major stimulatory G-protein in the basal ganglia and several other tissues (Zigman et al., 1993, *Endocrinology* 133:2508–2514).

Nucleocytoplasmic transport takes place through nuclear pores. Peripheral pore structures interact with transport receptors and their cargo when these receptor complexes first encounter the pore. Protein nuclear import is mediated by basic nuclear localization signals (NLSs) that bind to the importin alpha (Imp alpha) NLS receptor. Imp beta is also necessary for nuclear import.

The human immunodeficiency virus type 1 (HIV-1) Rev protein binds to unspliced HIV-1 pre-mRNA and exports it from the nucleus. Rev itself can "shuttle" between the nucleus and cytoplasm. This bi-directional transport is mediated by two specific Rev sequences: a NLS, which overlaps the RNA-binding domain, and a distinct nuclear export signal (NES). Imp beta supports Tat or Rev nuclear import (Truant et al., 1999, *Mol Cell Biol,* 19:1210–7) through the classical NLS pathway as demonstrated by inhibition of Imp beta interaction with Tat and Rev by RanGTP but not RanGDP.

Importin beta also interacts with the HIV-1 protein Vpr (Jenkins et al., 1998, *J Cell Biol,* 143:875–885). Vpr contains two discrete nuclear targeting signals that use two different import pathways, both of which are distinct from the classical NLS pathway. Vpr import does not appear to require Ran-mediated GTP hydrolysis and persists under conditions of low energy. Vpr bypasses many of the soluble receptors involved in import of cellular proteins. Vpr directly accesses the NPC, a property that can help to ensure the capacity of HIV to replicate in nondividing cellular hosts (Jenkins et al., ibid.). Overexpression of either Vpr or importin beta in yeast blocks nuclear transport of mRNAs. A mutant form of Vpr, Vpr F34I, that does not localize at the nuclear envelope, or bind to importin alpha and nucleoporins, renders HIV-1 incapable of infecting macrophages efficiently. Vpr F34I, however, still causes G2 arrest, demonstrating that the dual functions of Vpr are genetically separable (Vodicka et al., 1998, *Genes Dev,* 12:175–185).

The rodent, avian, and insect L1-like cell adhesion molecules are members of the immunoglobulin superfamily that have been implicated in axon growth. The entire coding region of human L1CAM has been cloned and found to have a high degree of homology to mouse L1CAM, with 92% identity at the amino acid level (Hlavin et al., 1991, *Genomics* 11:416–423). This similarity suggests that L1CAM is an important molecule in normal human nervous system development and nerve regeneration. This molecule has never been associated with HIV-1 life-cycle.

Cyclophilins have been proposed to act as chaperones in a variety of cellular processes. U4/U6 snRNP-associated cyclophilin has been cloned and sequenced (Horowitz et al., 1997, *RNA* 3:1374–1387).

The nucleotide sequence for the recepin gene, a novel human liver CDNA encoding a serpin-like molecule has been directly submitted to GenBank.

Arg and c-Abl represent the mammalian members of the Abelson family of protein-tyrosine kinases. The Arg/Abl-binding protein, ArgBP2, was isolated using a segment of the Arg COOH-terminal domain as bait in the yeast two-hybrid system (Wang et. al., 1997, *J. Biol Chem.* 272:17542–1 7550). ArgBP2 contains three COOH-terminal Src homology 3 domains, a serine/threonine-rich domain, and several potential Abl phosphorylation sites. ArgBP2 associates with and is a substrate of Arg and v-Abl, and is phosphorylated on tyrosine in v-Abl-transformed cells. ArgBP2 is widely expressed in human tissues and extremely abundant in heart. In epithelial cells, ArgBP2 is located in stress fibers and the nucleus, similar to the reported localization of c-Abl. In cardiac muscle cells, ArgBP2 is located in the Z-disks of sarcomeres. These observations indicate that ArgBP2 functions as an adapter protein to assemble signaling complexes in stress fibers, and that ArgBP2 is a link between Abl family kinases and the actin cytoskeleton.

Interferon (IFN)-gamma has been implicated in the pathogenesis of several autoimmune disorders and inflammatory skin diseases. A cDNA detecting a 1.6 kb mRNA that accumulated in response to IFN-gamma but not in response to IFN-alpha or IFN-beta has been cloned and sequenced (Flohr et al., 1992, *Eur J Immunol.* 22:975–979). The gene is regulated by IFN-gamma in human cell lines of epithelial origin. The mRNA encodes a predicted protein of 432 amino acids and the primary structure of the protein demonstrates that it is a member of developmentally regulated keratin class I genes.

The oncoprotein 18 (Op18) gene encodes a proliferation-related cytosolic phosphoprotein which is induced in normal lymphocytes following mitogenic stimulation. The cDNA for this gene has been cloned (Zhu et al., 1989, *J. Biol Chem.* 264:14556–14560). It is encoded by two different-sized full-length cDNAs. The two cDNAs differ in their 3'-noncoding regions as a result of alternative polyadenylation. The Op18 gene, which is 6.3 kilobases in length, is comprised of five exons and four introns and exhibits features that are common to other genes involved in cellular growth and proliferation. This gene is highly conserved in several animal species and low stringency hybridization studies suggest that the p18 gene can be a member of a family of partially homologous genes in the human genome. The increase in Op18 polypeptide in leukemia is associated with increased RNA transcription without gene amplification or rearrangement(Melhem et al., 1991, *J. Biol Chem.* 266:17747–17753). Treatment of K562 leukemia cell line with hemin that induces terminal differentiation resulted in decreased expression of Op18.

The nucleotide sequence for the recepin gene, a novel human liver cDNA encoding a serpin-like molecule has been directly submitted to GenBank. Arg and c-Abl represent the mammalian members of the Abelson family of protein-tyrosine kinases. The Arg/Abl-binding protein, ArgBP2, was isolated using a segment of the Arg COOH-terminal domain as bait in the yeast two-hybrid system (Wang et. al., 1997, *J. Biol Chem.* 272:17542–17550). ArgBP2 contains three COOH-terminal Src homology 3 domains, a serine/threonine-rich domain, and several potential Abl phosphorylation sites. ArgBP2 associates with and is a substrate of Arg and v-Abl, and is phosphorylated on tyrosine in v-Abl-transformed cells. ArgBP2 is widely expressed in human tissues and extremely abundant in heart. In epithelial cells, ArgBP2 is located in stress fibers and the nucleus, similar to the reported localization of c-Abl. In cardiac muscle cells, ArgBP2 is located in the Z-disks of sarcomeres. These observations indicate that ArgBP2 functions as an adapter protein to assemble signaling complexes in stress fibers, and that ArgBP2 is a link between Abl family kinases and the actin cytoskeleton. Interferon (IFN)-gamma has been implicated in the pathogenesis of several autoimmune disorders and inflammatory skin diseases. A cDNA detecting a 1.6 kb mRNA that accumulated in response to IFN-gamma but not in response to IFN-alpha or IFN-beta has been cloned and sequenced (Flohr et al., 1992, *Eur J Immunol.* 22:975–979). The gene is regulated by IFN-gamma in human cell lines of epithelial origin. The mRNA encodes a predicted protein of 432 amino acids and the primary structure of the protein demonstrates that it is a member of developmentally regulated keratin class I genes. The oncoprotein 18 (Op18) gene encodes a proliferation-related cytosolic phosphoprotein which is induced in normal lymphocytes following mitogenic stimulation. The cDNA for this gene has been cloned (Zhu et al., 1989, *J Biol Chem.* 264:14556–14560). It is encoded by two different-sized full-length cDNAs. The two cDNAs differ in their 3'-noncoding regions as a result of alternative polyadenylation. The Op18 gene, which is 6.3 kilobases in length, is comprised of five exons and four introns and exhibits features that are common to other genes involved in cellular growth and proliferation. This gene is highly conserved in several animal species and low stringency hybridization studies suggest that the p18 gene can be a member of a family of partially homologous genes in the human genome. The increase in Op18 polypeptide in leukemia is associated with increased RNA transcription without gene amplification or rearrangement (Melhem et al., 1991, *J. Biol Chem.* 266:17747–17753). Treatment of K562 leukemia cell line with hemin that induces terminal differentiation resulted in decreased expression of Op18. The nucleotide sequence for the recepin gene, a novel human liver cDNA encoding a serpin-like molecule has been directly submitted to GenBank. Arg and c-Abl represent the mammalian members of the Abelson family of protein-tyrosine kinases. The Arg/Abl-binding protein, ArgBP2, was isolated using a segment of the Arg COOH-terminal domain as bait in the yeast two-hybrid system (Wang et. al., 1997, *J. Biol Chem.* 272:17542–17550). ArgBP2 contains three COOH-terminal Src homology 3 domains, a serine/threonine-rich domain, and several potential Abl phosphorylation sites. ArgBP2 associates with and is a substrate of Arg and v-Abl, and is phosphorylated on tyrosine in v-Abl-transformed cells. ArgBP2 is widely expressed in human tissues and extremely abundant in heart. In epithelial cells, ArgBP2 is located in stress fibers and the nucleus, similar to the reported localization of c-Abl. In cardiac muscle cells, ArgBP2 is located in the Z-disks of sarcomeres. These observations indicate that ArgBP2 functions as an adapter protein to assemble signaling complexes in stress fibers, and that ArgBP2 is a link between Abl family kinases and the actin cytoskeleton. Interferon (IFN)-gamma has been implicated in the pathogenesis of several autoimmune disorders and inflammatory skin diseases. A cDNA detecting a 1.6 kb mRNA that accumulated in response to IFN-gamma but not in response to IFN-alpha or IFN-beta has been cloned and sequenced (Flohr et al., 1992, *Eur J Immunol.* 22:975–979). The gene is regulated by IFN-gamma in human cell lines of epithelial origin. The mRNA encodes a predicted protein of 432 amino acids and the primary structure of the protein demonstrates that it is a member of developmentally regulated keratin class I genes. The oncoprotein 18 (Op18) gene encodes a proliferation-related cytosolic phosphoprotein which is induced in normal lymphocytes following mitogenic stimulation. The cDNA for this gene has been cloned (Zhu et al., 1989, *J Biol Chem.* 264:14556–14560). It is encoded by two different-sized full-length cDNAs. The two cDNAs differ in their 3'-noncoding regions as a result of alternative polyadenylation. The Op18 gene, which is 6.3 kilobases in length, is comprised of five exons and four introns and exhibits features that are common to other genes involved in cellular growth and proliferation. This gene is highly conserved in several animal species and low stringency hybridization studies suggest that the p18 gene can be a member of a family of partially homologous genes in the human genome. The increase in Op18 polypeptide in leukemia is associated with increased RNA transcription without gene amplification or rearrangement (Melhem et al., 1991, *J. Biol Chem.* 266:17747–17753). Treatment of K562 leukemia cell line with hemin that induces terminal differentiation resulted in decreased expression of Op18.

Putative G-protein coupled receptor has been cloned recently (Mayer et al., 1998, *Biochim. Biophys. Acta* 1395:301–308). The cDNA sequence encodes a protein of 399 amino acids. Northern and RNA dot blot analyzes demonstrated that the major 4.8 kb transcript is predominantly expressed in brain. In situ hybridization studies of tissue sections revealed high expression in neurons of the brain and spinal cord, thymocytes, megakaryocytes, and macrophages.

Glucosidase alpha II is a glycoprotein involved in the processing of N-linked glycans. It resides in the endoplasmic reticulum (ER) and controls the formation of glycoproteins in the ER. The glucosidase alpha II gene was cloned and the encoded protein has been shown not to contain known ER retention signals or hydrophobic regions that could represent a transmembrane domain. Glucosidase alpha II, however, has been shown to contain a single N-glycosylation site close to the amino terminus. HIV-1 contains two heavily glycosylated envelope proteins, gp120 and gp41, which mediate attachment of virions to the glycosylated cell surface receptor molecule, CD4. It has also been shown that gp120 and gp41 can be involved in syncytium formation and associated cytopathic effects of HIV. The alpha-glucosidase inhibitor N-butyldeoxynojirimycin (NB-DNJ) is an inhibitor of HIV replication and HIV-induced syncytium formation in vitro. The NB-DNJ-mediated retention of glycosylated Bglycans inhibits HIV entry by a combined effect of a reduction in virion gp120 content and a qualitative defect within the remaining gp120, preventing it from undergoing conformational changes after CD4 binding (Fischer et al., 1996, *J. Virol.* 70:7153–7160).

In mammals there are at least three isoforms of the glycolytic enzyme enolase encoded by three similar genes: alpha, beta and gamma. Structure of the human gene for alpha-enolase locus has been described (Giallongo et al., 1990, *Eur J Biochem,* 190:567–573). The gene is composed of 12 exons distributed over more than 18,000 bases. The structure of this gene has a high degree of similarity to that of the human and rat gamma-enolase genes, with identical positions for all the intron regions. The putative promoter region, like that of other house-keeping genes, lacks canonical TATA and CAAT boxes, is extremely G+C-rich and contains several potential SP1 binding sites. It has been demonstrated that a 48 kDa protein (p48), that specifically reacts with an antiserum directed against the 12 carboxyl-terminal amino acids of the c-myc gene product, is alpha enolase (Giallongo et al., 1986, *Proc Natl Acad Sci USA* 83:6741–6745).

The murine gene, macrophage inflammatory protein 1 alpha (MIP1 alpha) is a cytokine that inhibits proliferation of bone marrow stem cells (Russell et al., 1993, *DNA Cell Biol.* 12:157–175). MIP1 alpha has been shown to suppress HIV-1 replication in human peripheral blood mononuclear cells. MIP1 alpha can also suppress transcription from the HIV-1 LTR in transient transfection assays in cells of the Jurkat acute T leukemia cell line (Handen et al., 1997, *FEBS Lett.* 410:301–302). MIP1 alpha is a ligand of CCR5 and can prevent M-tropic HIV infection in vitro (Cochi et al., 1995, *Science,* 270:1811–1815; Gong et al., 1998, *J. Biol. Chem,* 271:2599–2603). Certain individuals with elevated levels of MIP1 alpha expression appear to be resistant to HIV infection (Cho et al., 1997, *Biomed. Pharmacother.* 51:221–229). It is not known, however, how downmodulation of intracellular expression of MIP1 alpha can affect HIV replication in T cells.

The translationally-controlled tumor protein (TCTP) is a growth-related protein which is regulated at the translational level. It is present in mammals, higher plants and *Saccharomyces cerevisiae* (Sanchez et al., 1997, *Electrophoresis* 18:150–155). It has been shown that macrophage activation by PHA results in up-regulation of TCTP (Walsh et al., 1995, *J. Leukoc Biol.* 57:507–512). TCTP is also differentially expressed in C6.9 glioma cells during vitamin D-induced cell death (Baudet et al. ,1998, *Cell Death Differ,* 5:116–125). TCTP is localized on chromosome 13q12-q14 (MacDonald et al., 1999, *Cytogenet Cell Genet,* 84:128–129). Both vitamin D and PHA can induce latent HIV-1. This indicates that the TCTP1 pathway overlaps with signal transduction pathways involving critical for the HIV-1 life-cycle.

The nef gene of human and simian immunodeficiency virus is a key factor in acquired immunodeficiency syndrome pathogenesis and virus replication. Several Nef-induced phenomena, including the down-regulation of CD4 in T cells, have been previously reported. Naf1 (Nef-associated factor 1) has been cloned (Fukushi, 1999, *FEBS Lett.* 442: 83). The Naf1 gene generates two isoforms, Naf1 alpha and beta, containing four coiled-coil structures. Naf1 mRNA is ubiquitously expressed in human tissues with strong expression in peripheral blood lymphocytes and spleen. Naf1 overexpression in T cells increases surface CD4 expression. Expression of Nef suppressed this Naf1-induced augmentation of CD4 expression, providing a novel mode of Nef action in CD4 down-regulation.

The human gene of a protein that modifies $Na^+$-D-glucose co-transport, $Na^+$-D-Glucose cotransport regulator gene (hRS1), has been cloned and sequenced (Lambotte et al., 1996, *DNA Cell Biol,* 15:769–777). It is an intronless gene designated hRS1 (6.743 bp), which encodes a 617 amino acid protein with 74% identity to pRS1. By fluorescence in situ hybridization, hRS1 was localized to chromosome 1p36.1. It is homologous to the nucleic acid sequence of pRS1, which was cloned from pig kidney cortex and encodes a membrane-associated protein involved in Na$^+$-coupled sugar transport. pRS1 alters sugar transport by SGLT1 from rabbit intestine or by SMIT from dog kidney which is homologous to SGLT1. In contrast, pRS1 does not influence transporters from other genetic families. The function of hRS1 has been demonstrated by co-expression experiments of hRS1 and SGLT1, from human intestine, in oocytes from *Xenopus laevis*. It was demonstrated that hRS1-protein inhibits Na$^+$-D-glucose co-transport expressed by human SGLT1 by decreasing both the $V_{max}$ and the apparent $K_m$ value of the transporter. The analysis of the 5'-noncoding sequence of hRS1 revealed different enhancer consensus sequences that are absent in the SGLT1 gene, e.g., several consensus sequences for steroid-binding proteins.

Hsp90 is an abundant molecular chaperone that is involved in the folding of a defined set of signaling molecules including steroid-hormone receptors and kinases. In vitro experiments suggest that Hsp90 contains two different binding sites for non-native proteins, which allow it to combine the properties of a promiscuous chaperone with those of a dedicated folding-helper protein. The heat shock protein Hsp90 is known as an essential component of several signal transduction pathways and has now been identified as an essential host factor for hepatitis B virus replication. Hsp90 interacts with the viral reverse transcriptase to facilitate the formation of a ribonucleoprotein (RNP) complex between the polymerase and an RNA ligand (Hu et al., 1996, *Proc Natl Acad Sci USA* 93:1060–1064). Hsp90 has not been associated with the HIV life-cycle. Specific inhibitors of hsp90, e.g., anti-fungal macrolydes, geldanamycin and radocicol can be used against HIV-1 infection.

FK506-binding protein A1 is a potent immunosuppressive agent which is 100-fold more active than cyclosporin A, a cyclic decapeptide that is used to prevent rejection after transplantation of bone marrow and organs, such as kidney, heart, and liver. It was shown that FK506 binds to a cellular protein distinct from cyclophilin which is known to bind cyclosporin A. A cDNA has been isolated from human peripheral blood T-cells that encodes FK506-binding protein (FKBP) (Maki et al., 1990, *Proc Natl Acad Sci USA* 87: 5440–5443). The isolated cDNA contained an open reading frame encoding 108 amino acid residues. The first 40 residues of the deduced amino acid sequence were identical to those of the reported amino-terminal sequence of bovine FKBP, indicating that the DNA sequence isolated represents the gene coding for FKBP. It is expressed in brain, lung, liver, placental cells and leukocytes. Induction of Jurkat leukemic T cells with phorbol 12-myristate 13-acetate and ionomycin did not affect the level of FKBP mRNA.

Proteins of the Myc and Mad family are involved in transcriptional regulation and mediate cell differentiation and proliferation. These molecules share a basic-helix-loop-helix leucine zipper domain (bHLHZip) and bind DNA at the E box (CANNTG) consensus by forming heterodimers with Max (Meroni et al., 1997, *EMBO J.* 15–16:2892–906). Rox transcriptional repressor heterodimerizes with Max and weakly homodimerizes. Interestingly, bandshift assays demonstrate that the Rox-Max heterodimer shows a novel DNA binding specificity, having a higher affinity for the CACGCG site compared with the canonical E box CACGTG site. Transcriptional studies indicate that Rox represses transcription in both human HEK293 cells and yeast. Moreover, ROX expression appears to be induced in U937 myeloid leukemia cells stimulated to differentiate with 12-O-tetradecanoylphorbol-13-acetate. These data indicate that HIV-1 may use Rox to interfere with cellular transcription, since an anti-sense element derived from this gene is able to interfere with HIV-1 replication.

Human signal sequence receptor gene, SSR2, encodes an endoplasmic reticulum (ER) membrane protein associated with protein translocation across the ER membrane. This gene has been cloned (Chinen et al., 1995, *Cytogenet Cell Genet.* 70:215–217). Northern blot analysis revealed its ubiquitous expression in all organs examined (Chinen et al., ibid.). The gene is located on chromosome bands 1q21 through q23. Various GSEs described herein affect expression of the ER proteins calnexin, glucosidase alpha and glucosyltransferase, and such expression has an inhibitory effect on HIV replication. The SSR2 gene inhibits HIV-1 replication in a similar manner, affecting translocation of gp160 into the ER.

A human tumorous imaginal disc protein, hTid-1, which is a homolog of the Drosophila tumor suppressor protein Tid56, has been cloned (Schilling, 1998, *Virology* 247:74–85). The hTid-1 protein is able to form complexes with the human papillomavirus E7 oncoprotein. The carboxyl terminal cysteine-rich metal binding domain of E7 is the major determinant for interaction with hTid-1. The hTid-1 protein is a member of the DnaJ-family of chaperones. The mRNA of hTid-1 is widely expressed in human tissues, including the HPV-18-positive cervical carcinoma cell line, HeLa, and human genital keratinocytes, the normal host cells of the HPVs. The hTid-1 gene has been mapped to the short arm of chromosome 16. The large tumor antigens of polyomaviruses encode functional J-domains that are important for viral replication and cellular transformation. The ability of HPV E7 to interact with a cellular DnaJ protein suggests that these two viral oncoproteins may target common regulatory pathways through J-domains (Schilling, ibid.).

Heparin sulfate proteoglycans are expressed on the cell surface and their corresponding binding sites have been suggested to play an important role during the initial attachment of murine blastocysts to uterine epithelium, and human trophoblastic cell lines to uterine epithelial cell lines. Three major peptide fragments from heparin-binding protein have been isolated and partial amino-terminal amino acid sequence for each peptide fragment was obtained (Raboudi, et al., 1992, *J. Biol. Chem.* 267, 11930–11939). A full-length cDNA for a heparin-binding protein, named HP/HS interacting protein (HIP), was cloned from RL95 cells (Liu et al., 1996, *J. Biol. Chem.* 271:11817–11823). The HIP cDNA encodes a protein of 159 amino acids. Transfection of HIP full-length cDNA into NIH-3T3 cells resulted in the cell 'surface expression of HIP protein having a size similar to HIP expressed by human cells. Predicted amino acid sequence indicates that HIP lacks a membrane spanning region and has no consensus sites for glycosylation. Northern blot analysis detected a single transcript of 1.3 kilobases in both total RNA and poly(A$^+$) RNA. Examination of human cell lines and normal tissues using both Northern blot and Western blot analyzes revealed that HIP is expressed at different levels in a variety of human cell lines and normal tissues.

Many growth factors mediate their cellular responses by binding to and activating cell surface receptors that contain tyrosine kinase domains. These ligand-bound receptors then stimulate intracellular signaling cascades that involve tyrosine phosphorylation. SHIP selectively removes phosphate from the 5-position of the inositol ring in inositol-containing lipids (Pesesse et al., 1997, *Biochem. Biophys. Res. Commun.* 239:697–700). Thus, SHIP terminates signal transduction cascades by regulating the level of phospholipid molecules. SHIP is present in hematopoietic cells and has been shown to regulate the activation of the serine/threonine kinase Akt, thereby controlling proliferation and survival mechanisms of hematopoietic cells (Carver et al., 2000, *Blood* 96:1449). SHIP is also expressed in heart, skeletal muscle, placenta and thyroid cells. The coding sequence of human SHIP has been described in Ware et al., 1996, *Blood* 88:2833–2840 (GenBank Accession No. HSU57650) and U.S. Pat. No. 6,025,198, issued Feb. 15, 2000, to Bennett et al.

Activation of the enzyme protein kinase C (PKC) is associated with translocation of the protein from the soluble cell fraction to the membrane cell fraction. Numerous different proteins bind to PKC during this translocation process. GNB2L1 is one such protein (Ron et al., 1994, *Proc. Natl. Acad. Sci. USA* 91:839). The coding sequence of GNB2L1 has been described (GenBank Accession No. NM 006098.1; Guillemot et al., 1989, *Proc. Natl. Acad. Sci. U.S.A.* 86:4594–4598).

ArgRS is involved in protein synthesis. It is one component of a multienzyme complex with other aminoacyl-tRNA synthetases. Two different forms of ArgRS have been isolated from mammalian cell extracts, a free form and a complex-bound form. Both forms have similar catalytic activity. Inhibition of tRNA synthetase activity prevents protein synthesis. In bacteria, inhibition of tRNA synthetase activity induces a state of dormancy. The coding sequence of ArgRS has been described (GenBank Accession No. NM 002887.1; Girjes et al., 1995, *Gene* 164:347–350).

The ATP binding cassette (ABC) transporters are a family of membrane proteins that mediate transport and channel functions in both eukaryotic and prokaryotic cells. ABC proteins have similar structure generally comprising twelve transmembrane segments and two nucleotide binding domains. ABC transporters are capable of binding to diverse compounds such as drugs, peptides, ionophores, chemoattractants or immunosupressants. Multidrug resistance protein 1 (MDR1) has been shown to inhibit virus infection in cell lines infected with HIV-1 (Lee et al., 2000, *FASEB J.* 14:516–522). The sequence of the ABC Transporter of the present invention is substantially not identical to the sequence of MDR1 so their respective mechanisms of action are not predictably shared. The coding sequence of an ABC transporter of the present invention has been described (EMBL Accession No. AJ005016.1; submitted by Stanchi, F., Mar. 27, 1998; and U.S. Pat. No. 6,080,842, issued Jun. 27, 2000, to Hillman et al.).

GTP-binding proteins (G protein) are involved in numerous cellular functions. CDC42 is a G protein involved in mammalian signal transduction. In particular, CDC42 is known to activate Nef-associated kinase activity resulting in the activation of HIV-1 replication via Nef (Lu et al., 1996, *Current Biology* 6:1677–1684). Dominant negative forms, however, of CDC42 have been shown to inhibit HIV-1 infection (Lu et al., ibid.). The coding sequence of a CDC42 has been described by Koland et al., 1990, *Proc. Natl. Acad. Sci. USA* 87:9853–9857 (GenBank Accession No. NM001791.1) and in U.S. Pat. No. 5,527,884, issued Jun. 18, 1996, to Russell et al.

Cyclosporin A (Csa) can block signal transduction resulting in activation of T cells. Csa-19 was isolated when its expression was downregulated by treating T cells. Csa-19 was identified as a gene that is downregulated by Csa. Fisicaro et al., 1995, *Molecular Immunology* 32:565–572, has speculated that Csa-19 is a substrate for a tyrosine kinase involved in signal transduction in lymphoid tissues. The coding sequence for Csa-19 has been described (GenBank Accession No. HSU12404; Fisicaro et al., ibid.).

FYN is a src protein tyrosine kinase that is involved in signal transduction from the T cell receptor. FYN can be expressed in two isoforms. One form binds subunits of the T cell receptor and cD3 complex. Activation of FYN through the T cell receptor results in T cell proliferation. Phipps et al., 1997, *Blood* 90:3603–3612, demonstrated that FYN kinase activity and protein levels were increased in asymptomatic HIV-infected patients compared to uninfected individuals. Phipps et al. proposed that chronic activation of FYN may increase apoptosis of HIV infected cells leading to delayed onset of disease. The coding sequence for FYN has been described (GenBank Accession No. AF001862.1; da Silva et al., 1997, *Proc. Natl. Acad. Sci. USA* 94:7493–7498).

Cathepsin proteins have multiple forms generated by post-translational modification and glycosylation (Tam et al., 1994, *Gene* 139:171–176). CTSB is a lysosomal cysteine protease of the papain family of enzymes, the main function of which is to degrade proteins that enter the lysosomal system from the outside of the cell (Mort et al., 1997, *Int. J. Biochem. Cell. Biol.* 29:715–720). Altered expression of CTSB has been observed in tumor cells when compared to normal cells. Cathepsin D and cathepsin G have been shown to enhance HIV-1 infection in macrophage and mammary tumor cells, respectively (Messaoudi et al., 2000, *J. Virol.* 74:1004–1007 and Moriuchi et al., 2000, *J. Virol.* 74:6849–6855). The coding sequence of CTSB has been described (GenBank accession No. L22569; Tam et al., ibid.).

Cathepsin L is also a cysteine protease. It is initially translated as preprocthepsin L, and then processed in the Golgi to procathepsin L. Mature cathepsin L is then stored in lysosomes. It has been speculated that procathepsin L participates in tumor metastases. The coding sequence of cathepsin L has been described (GenBank accession No. NM 001912; Gal and Gottesman, 1988, *Biochem. J.* 253:303–306).

Glutaredoxin is a glutathione-dependent cytosolic enzyme that catalyses disulfide reduction. The protein has been found in yeast, eubacteria, archaebacteria and eukaryotes (Holmgren et al., 1989, *J. Biol. Chem.* 264:13963–13966 and Wells et al., 1993, *Adv. Enzymol. Relat. Areas. Molec. Biol.* 66:149–201). All the form have an active site of Cys-Pro-Tyr(-Phe)-Cys (Holmgren et al., ibid. and Wells et al., ibid.). Glutaredoxin has been shown to donate electrons to ribonucleoside diphosphate reductase in bacteria (Holmgren et al., 1976, *Proc. Natl. Acad. Sci. USA* 73:2275–2279), deiodinate thyroxine to triiodothyronine in mammalian liver (Goswami and Rosenberg, 1985, *J. Biol. Chem.* 260:6012–6019), reduce dehydroascorbic acid in pigs (Wells et al., 1990, *J. Biol. Chem.* 268:15531–15535). Davis et al. (1997, *J. Biol. Chem.* 272:25935–25940) disclose regulation of HIV-1 protease by glutathione. Davis et al. demonstrate that glutaredoxin preferentially deglutathionylates cysteine 95 of the HIV-1 protease leading to modulation of protease activity. Davis et al. did not demonstrate that administration of glutaredoxin inhibits HIV-1 infection. The coding sequence of glutaredoxin has been described (GenBank Accession No. AF115104; Park and Levine, 1997, *Gene* 197:189–193).

The minimal size of a nucleic acid molecule of the present invention is the size required for the use of the nucleic acid molecule to inhibit HIV replication. One of skill in the art will recognize that the length can differ if the nucleic acid molecule is in the form of RNA or DNA. A nucleic acid molecule of the present invention can be used in a variety of applications including, but not limited to, as probes to identify additional nucleic acid molecules, as primers to amplify or extend nucleic acid molecules or in therapeutic applications to inhibit, for example, expression of a target gene of the present invention. Such therapeutic applications include the use of such nucleic acid molecules in, for example, anti-sense-RNA and -DNA molecules, triplex formation-, ribozyme- and/or RNA drug-based technologies, that function to inhibit HIV infection, and are referred to herein as "therapeutic nucleic acid molecules." For example, anti-sense RNA and DNA molecules can be used to directly block the translation of mRNA encoded by these cellular genes by binding to targeted MRNA and preventing protein translation. Polydeoxyribonucleotides can form sequence-specific triple helices by hydrogen bonding to specific complementary sequences in duplexed DNA. Formation of specific triple helices can selectively inhibit the replication and/or expression of targeted genes by prohibiting the specific binding of functional trans-acting factors.

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of cellular RNA sequences. Antisense RNA showing high affinity binding to target sequences can also be used as ribozymes by addition of enzymatically active sequences known to those skilled in the art.

Nucleic acid molecules to be used in triplex helix formation should be single stranded and composed of deoxynucleotides. The base composition of these nucleic acid molecules must be designed to promote triple helix formation via Hoogsteen base pairing rules, which generally require sizeable stretches of either purines or pyrimidines to be present on one strand of a duplex. Nucleic acid molecule sequences can be pyrimidine-based, which will result in TAT and CGC triplets across the three associated strands of the resulting triple helix. The pyrimidine-rich polynucleotides provide base complementarity to a purine-rich region of a single strand of the duplex in a parallel orientation to that strand. In addition, nucleic acid molecules can be chosen that are purine-rich, for example, containing a stretch of G residues. These nucleic acid molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation can be increased by creating a so called "switchback" polynucleotide. Switchback polynucleotides are synthesized in an alternating 5'-3', 3'-5' manner, such that they base pair with first one strand of a duplex and then the other, eliminating the necessity for a sizeable stretch of either purines or pyrimidines to be present on one strand of a duplex.

Both anti-sense RNA and DNA molecules, and ribozymes of the invention can be prepared by any method known in the art. These include techniques for chemically synthesizing polydeoxyribonucleotides well known in the art such as solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into host cells.

The present invention, therefore, includes such therapeutic nucleic acid molecules and methods to interfere with the production of proteins encoded by a target gene necessary for HIV infection of the present invention by use of one or more of such technologies.

A preferred therapeutic nucleic acid molecule comprises at least a portion of a target gene encoding a protein selected from the group consisting of NADH dehydrogenase, 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, $Na^+$-D-glucose cotransport regulator gene protein, hsp90 chaperone protein, FK506-binding protein A1, Rox, beta signal sequence receptor, tumorous imaginal disc protein, cell surface heparin binding protein, SHIP, GNB2L1, ArgRS, ABC Transporter, CDC42, Csa-19, FYN, CTSB, cathepsin L or GLRX, or homologs thereof, in which the portion is capable of down-regulating the expression of the associated target gene. A more preferred therapeutic nucleic acid molecule is a GSE nucleic acid molecule of the present invention, particularly comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69; SEQ ID NO:71; SEQ ID NO:73; SEQ ID NO:75; SEQ ID NO:77, SEQ ID NO:79, SEQ ID NO:81, SEQ ID NO:83, SEQ ID NO:85; SEQ ID NO:87; SEQ ID NO:89; SEQ ID NO:91; SEQ ID NO:93, SEQ ID NO:95, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112 and/or SEQ ID NO:114, or other GSE sequences disclosed herein, as well as complements of any of these sequences or homologs thereof.

The present invention also includes a recombinant vector, which includes a nucleic acid molecule of the present invention inserted into any vector capable of delivering the nucleic acid molecule into a host cell. Such a vector contains heterologous nucleic acid sequences, that is nucleic acid sequences that are not naturally found adjacent to a cell-derived nucleic acid molecule of the present invention. The vector can be either RNA or DNA, either prokaryotic or eukaryotic, and typically is a virus or a plasmid. Recombinant vectors can be used in the cloning, sequencing, and/or otherwise manipulating of nucleic acid molecules of the present invention. One type of recombinant vector, herein referred to as a recombinant expression molecule and described in more detail below, can be used in the expression of nucleic acid molecules of the present invention. Preferred recombinant vectors are capable of replicating in the transformed cell.

A preferred nucleic acid molecule to include in a recombinant vector of the present invention is a cell-derived nucleic acid molecule of the present invention. A particularly preferred nucleic acid molecule to include in a recombinant vector is at least a portion of a target gene that encodes a protein selected from the group consisting of NADH dehydrogenase, 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, $Na^+$-D-glucose cotransport regulator gene protein, hsp90 chaperone protein, FK506-binding protein A1, Rox, beta signal sequence receptor, tumorous imaginal disc protein, cell surface heparin binding protein, SHIP, GNB2L1, ArgRS, ABC Transporter, CDC42, Csa-19, FYN, CTSB, cathepsin L or GLRX, or complements or homologs thereof Other preferred nucleic acid molecules to include in a recombinant vector is a GSE nucleic acid molecule having a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69; SEQ ID NO:71; SEQ ID NO:73; SEQ ID NO:75; SEQ ID NO:77, SEQ ID NO:79, SEQ ID NO:81, SEQ ID NO:83, SEQ ID NO:85; SEQ ID NO:87; SEQ ID NO:89; SEQ ID NO:91; SEQ ID NO:93, SEQ ID NO:95, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112 and/or SEQ ID NO:114, or other GSE sequences disclosed herein, as well as complements of any of these sequences or homologs thereof.

A recombinant expression molecule or construct of the present invention comprises one or more nucleic acid molecules of the present invention operably linked to an expression vector containing one or more regulatory sequences. The phrase "operably linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operably linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a regulatory sequence includes a sequence which is capable of controlling the initiation, elongation, and termination of transcription. Particularly important regulatory sequences are those which control transcription initiation, such as promoter, enhancer, operator and repressor sequences. Suitable regulatory sequences include any transcription control sequence that can function in a cell susceptible to infection by HIV. A variety of such transcription control sequences are known to those skilled in the art. Additional suitable regulatory sequences include tissue-specific promoters and enhancers as well as lymphokine-inducible promoters (e.g., promoters inducible by interferons or interleukins). Regulatory sequences of the present invention can also include naturally-occurring transcription control sequences naturally associated with a DNA sequence encoding a nucleic acid molecule of the present invention. In cases where a recombinant molecule of the present invention is expressed as a protein, specific initiation signals can be required for efficient translation of inserted nucleic acid molecules. Exogenous translational control signals, including the ATG initiation codon, need to be provided. Furthermore, the initiation codon must be in phase with the reading frame of the inserted nucleic acid molecule to ensure translation of the entire insert. These exogenous translational control signals and initiation codons can be of a variety of origins, both natural and synthetic.

Preferred expression vectors of the present invention are derived from viruses such as retroviruses, adenovirus, adeno-associated virus, herpes viruses, or papilloma viruses. Methods which are well known to those skilled in the art can be used to construct a recombinant molecule of the present invention (Sambrook el al., 1989, Molecular Cloning: A laboratory Manual, Cold Spring Harbor Laboratory, N.Y. and Ausubel et al., 1989, Current Protocols in Molecular Biology, Greene Publishing Associates and Wiley Interscience, N.Y.). In cases where an adenovirus is used as an expression vector, a nucleic acid molecule of the present invention can be ligated to an adenovirus transcription-translation control complex, e.g., the late promoter and tripartite leader sequence. This chimeric gene can then be inserted in the adenovirus genome by in vitro or in vivo recombination. Insertion in a non-essential region of the viral genome, e.g., region E1 or E3, will result in a recombinant virus that is viable and capable of expressing GSEs in infected hosts (Logan & Shenk, 1984, *Proc. Natl. Acad. Sci. USA* 81:3655–3659).

It will be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operably linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention can be improved by fragmenting, modifying, or derivatizing the resultant protein.

Various modifications to the nucleic acid molecules can be introduced as a means of increasing intracellular stability and half-life. Possible modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the polydeoxyribonucleotide backbone.

One embodiment of the present invention is an isolated protein that is necessary for HIV infection. Such a protein is referred to herein as a "cell-derived protein." As used herein, the term "protein" is intended to include both polypeptides and peptides. Preferably, the invention provides peptides or less than full-length fragments of such cell-derived proteins of the invention, wherein expression of said proteins in an HIV-susceptible cell inhibits HIV infection, replication or production of HIV progeny virus. Also encompassed by this definition are full-length proteins having at least one change in a constituent amino acid residue whereby the protein no longer supports HIV infection in said cell, and most preferably wherein the altered protein inhibits HIV infection, replication or production of HIV progeny virus. According to the present invention, an isolated, or biologically pure, protein is a protein that has been removed from its natural milieu. As such, "isolated" and "biologically pure" do not necessarily reflect the extent to which the protein has been purified. An isolated cell-derived protein of the present invention can be obtained from its natural source, can be produced using recombinant DNA technology or can be produced by chemical synthesis. Preferably, an isolated cell-derived protein of the present invention comprises at least a portion of a protein selected from the group consisting of NADH dehydrogenase, 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-sNRNP associated cyclophilin, recepin, Arg/Abl interacting protein (ArgBP2A), keratin related protein, p18 protein, p40 protein, glucosidase II, alpha enolase, inacrophage inflammatory protein 1 alpha, tumor protein translationally-controlled 1 (TCTP1), BBC1, Nef interacting protein, $Na^+$-D-glucose cotransport regulator gene protein, hsp90 chaperone protein, FK506-binding protein A1, Rox, beta signal sequence receptor, tumorous imaginal disc protein or cell surface heparin binding protein, SHIP, GNB2L1, ArgRS, ABC Transporter, CDC42, Csa-19, FYN, CTSB, cathepsin L, GLRX or any homolog of such a protein. An isolated protein of the present invention, including a homolog, can be identified in a straight-forward manner by the protein=s ability to inhibit HIV infection. Examples of homologs include proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog has at least some ability to inhibit HIV infection, wherein expression of the wildtype protein is necessary for HIV infection. Homologs also include at least one epitope capable of eliciting an immune response against a cell-derived protein. Techniques to measure HIV infection or the inhibition thereof, are disclosed herein.

Cell-derived protein homologs of the present invention can be the result of natural allelic variation or natural mutation. Cell-derived protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

The minimal size of a cell-derived protein homolog of the present invention is a size sufficient to function as an inhibitor of HIV infection. The minimal size of such homolog is typically at least about 6 to about 10 residues in length. There is no limit, other than a practical limit, on the maximal size of such a homolog in that the protein homolog can include a peptide, a less than full length fragment of a full-length protein, a full-length protein, multiple proteins, or portions thereof, wherein said full-length proteins most preferably comprise an altered amino acid sequence whereby the altered protein inhibits HIV infection, replication or production of infectious virus.

The present invention also includes mimetopes of cell-derived proteins of the present invention. As used herein, a mimetope of a cell-derived protein of the present invention refers to any compound that is able to mimic the activity of such a cell-derived protein (e.g., ability to inhibit HIV infection), often because the mimetope has a structure that mimics the cell-derived protein. It is to be noted, however, that the mimetope need not have a chemical structure similar to a cell-derived protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of cell-derived proteins of the present invention. Mimetopes can also be obtained by generating random samples of molecules, such as polynucleotides, peptides or other organic molecules, and screening such samples by affinity chromatography techniques using the corresponding binding partner. A preferred mimetope is a peptidomimetic compound that is structurally and/or functionally similar to a cell-derived protein of the present invention.

One embodiment of a cell-derived protein of the present invention is a fusion protein that includes a cell-derived protein-containing domain attached to one or more fusion segments. Suitable fusion segments are known to those of skill in the art depending upon the use of the segment, such as for protein stability or protein delivery into a cell. Fusion proteins are preferably produced by culturing a recombinant cell transformed with a fusion nucleic acid molecule that encodes a cell-derived protein including the fusion segment.

Isolated cell-derived proteins of the present invention have the further characteristic of being encoded by a cell-derived nucleic acid molecule of the present invention. A preferred cell-derived protein of the present invention is encoded by a nucleic acid molecule having a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID.NO:63, SEQ ID NO:65, SEQ ID NO:67, SEQ ID NO:69; SEQ ID NO:71; SEQ ID NO:73; SEQ ID NO:75 SEQ ID NO:77, SEQ ID NO:79, SEQ ID NO:81, SEQ ID NO:83, SEQ ID NO:85; SEQ ID NO:87; SEQ ID NO:89; SEQ ID NO:91; SEQ ID NO:93, SEQ ID NO:95, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112 and/or SEQ ID NO:114, or other sequences disclosed herein, as well as complements of any of these sequences or homologs thereof.

An isolated GSE nucleic acid molecule of the present invention can suppress HIV activity by either encoding a protein or RNA product. The present invention encompasses any such protein product, including a fusion protein, a leader peptide and a localization signal.

One embodiment of the present invention is an inhibitory composition that, when administered to an animal in an effective manner, is capable of protecting that animal from HIV infection, prophylactically or therapeutically. An inhibitory composition of the present invention can include a protective compound that down-regulates the expression of a gene that encodes NADH dehydrogenase, 2-oxoglutarate dehydrogenase, M2-type pyruvate kinase/ cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, Na$^+$-D-glucose cotransport regulator gene protein, hsp90 chaperone protein, FK506-binding protein A1, Rox, beta signal sequence receptor, tumorous imaginal disc protein, cell surface heparin binding protein, SHIP, GNB2L1, ArgRS, ABC Transporter, CDC42, Csa-19, FYN, CTSB, cathepsin L or GLRX. Such a protective compound comprises an isolated cell-derived nucleic acid molecule of the present invention operably linked to a regulatory sequence that controls its expression. The protective compound can be an RNA- or DNA-based molecule as described herein. Particularly preferred are GSE nucleic acid molecules of the present invention. A functionally-active fragment of a GSE, and a GSE containing conservative nucleotide substitutions as functional equivalents of a GSE, are within the scope of the present invention. Preferably, a GSE nucleic acid molecule, or a functional equivalent thereof, is operably linked to a regulatory sequence that controls its expression.

An inhibitory composition of the present invention can include a protective compound that inhibits the activity of a product of a gene that encodes NADH dehydrogenase, 2-oxoglutarate dehydrogenase, M2-type pyruvate kinase/ cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, Na+-D-glucose cotransport regulator gene protein, hsp90 chaperone protein, FK506-binding protein A1, Rox, beta signal sequence receptor, tumorous imaginal disc protein, cell surface heparin binding protein, SHIP, GNB2L1, ArgRS, ABC Transporter, CDC42, Csa-19, FYN, CTSB, cathepsin L or GLRX. Such a protective compound can include an isolated cell-derived protein of the present invention, in particular a peptide of a cell-derived protein, a mimetope of a cell-derived protein, and small molecule inhibitors of the activity of target gene products. Examples of protective compounds, e.g., proteins, mimetopes, nuclcic acid molecules, and inhibitors, are disclosed herein. It is within the scope of the present invention that an inhibitory composition can contain one or more protective compounds.

Suitable inhibitors of the activity of target gene products include compounds that interact directly with the active sites of such products, usually by binding to or otherwise interacting with or otherwise modifying the products=s active site. Product inhibitors can also interact with other regions of the product to inhibit its activity, for example, by allosteric interaction. The inhibitor of a product is identified by its ability to bind to, or otherwise interact with the product, thereby inhibiting the activity of the product and/or HIV infection.

In the case of NADH dehydrogenase, a large number of small molecule inhibitors are available in the art. Such inhibitors can be used in the methods of the present invention. An in vitro assay can be established to screen for additional NADH dehydrogenase complex I inhibitors by measuring membrane potential of live cells with DiC6, a dye which accumulates in the mitochondrial and cytoplasmic membrane depending on mitochondrial functional activities and ATP concentrations (*Methods in Enzymology*, 1995, 260:448). Compounds are selected for their ability to decrease membrane potential by methods well known in the art. Examples of NADH dehydrogenase inhibitors include, but are not limited to, Amytal, Annonin VI, Aurachin A, Aurachin B, Aureothin, Benzimidazole, Bullactin, Capsaicin, Ethoxyformic anhydride, Ethoxyquin, Fenpyroximate, Mofarotene (Ro 40-8757; arotinoids), Molvizarin, Myxalamide PI, Otivarin (annonaceous acetogenins), Pethidine, Phenalamid $A_2$, Phenoxan, Piericidin A, p-chloromercuribenzoate, Ranolazine (RS-43285), Rolliniasatin-1, Rolliniasatin-2, Rotenone, Squamocin, and Thiangazole (Singer et al., 1992, *Mol. Mechan. in Bioenergetics*, Chap. 6, p.153; Degli et al., 1994, *Biochem. J.* 301:161; Friedrich et al. 1994, *Eur. J. Biochem.* 219:691; Uchida et al., 1994, *Int. J. Cancer* 58:891; Wyatt et al., 1995, *Biochem. Pharmacol.* 50:1599; Shimomura et al., 1989, *Arch. Biochem Biophy.* 270:573).

Examples of inhibitors of 2-oxoglutarate dehydrogenase have been described by Majamaaet al., 1985, *Biochem. J.* 229:127–133. Examples of inhibitors of protein tyrosine phosphatase include, but are not limited to, ortho-vanadate, pervanadate, sodium vanadate, and phenylarsine oxide. Inhibitors of protein tyrosine phosphatase have been described by Yousefi et al., 1994, *Proc. Natl. Acad. Sci. USA* 91:10868–10872 and Lund-Johansen et al., 1996, *Cytometry* 25:182–190. Examples of inhibitors of EF-1 a include, but are not limited to, include quercetin (3,3',4'5,7-pentahydrozyflavone) and didemnin B.

Once a cellular gene has been identified as a potentially important target for supporting the HIV life cycle, assay systems can be established using such gene for screening and selection of additional compounds as anti-HIV therapeutics based on their ability to down-regulate the expression of the gene or inhibit the activities of its gene product. For example, a cell line which naturally expresses the gene of interest or has been transfected with it can be incubated with various compounds. A reduction of the expression of the gene of interest or an inhibition of the activities of its encoded product can be used as an indication that the compound is effective in inhibiting expression and/or the function of said gene. The compounds are retested in other assays such as in OM10.1 cells or in productive HIV infection to confirm their activities against HIV infection. These compounds can be screened from known organic compounds, products of peptide libraries and products of chemical combinatorial libraries.

One embodiment of the present invention is a method to identify a compound capable of inhibiting HIV infection. Such a method includes the steps of (a) exposing a cell to a putative inhibitory compound, in which the cell contains a cell-derived nucleic acid molecule of the present invention or its encoded protein, (b) measuring the expression of the nucleic acid molecule or the activity of its encoded protein in the cell, and (c) determining if the putative inhibitory compound down-regulates expression of the nucleic acid molecule or interferes with the activity of the protein it encodes. Putative inhibitory compounds to screen include small organic molecules, antibodies (including mimetopes thereof) and substrate analogs. Methods of determining expression of a nucleic acid molecule are known to those of skill in the art. For example, levels of mRNA derived from a nucleic acid molecule can be determined by Northern Blot,, nucleotide chip array techniques or reverse transcriptase techniques. Methods to determine the activity if a cell-derived protein are known to those skilled in the art. Determination of the inhibition of the activity of the cell-derived protein can be performed using methods known to one of skill in the art. For example, the activity of a cell-derived protein can be assessed by determining modifications to a substrate of a cell-derived protein of the present invention. Such modifications can include, for example, phosphorylation, de-phosphorylation, amino acid cleavage, inositol cleavage, enzyme activation and so on.

According to the present inventions, the identity of cell-derived nucleic acid molecule of the present invention to inhibit HIV infection can be used to identify one or more biological pathways involved in HIV infection. One embodiment of the present invention is a method to identify a biological pathway involved in HIV infection comprising the steps of (a) producing an expression library of nucleic acid molecule fragments from a nucleic acid molecule encoding a member of a biological pathway that includes a cell-derived protein of the present invention, (b) transferring the expression library into host cells, (c) selecting, the cells that contain a nucleic acid molecule that inhibits HIV infection by measuring levels of a detectable marker in the cells. It is within the skill of one in the art to determine the known members of a pathway based on the discovery of the cell-derived nucleic acid molecules of the present invention. A preferred cell-derived protein includes NADH dehydrogenase, 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, Na+-D-glucose cotransport regulator gene protein, hsp90 chaperone protein, FK506-binding protein A1, Rox, beta signal sequence receptor, tumorous imaginal disc protein, cell surface heparin binding protein, SHIP, GNB2L1, ArgRS, ABC Transporter, CDC42, Csa-19, FYN, CTSB, cathepsin L or GLRX.

Another embodiment of the present invention is a method to investigate the potential toxicity of a protective compound that inhibits the expression of a cell-derived nucleic acid molecule of the present invention by determining the redundancy of a protein encoded by a cell-derived nucleic acid molecule of the present invention in a cell. Methods to determine redundancy are known to those of skill in the art. For example, knock-out mice lacking expression of a cell-derived nucleic acid molecule of the present invention can be used to determine if the biological function(s) typically regulated by the protein encoded by the knocked-out gene is normal. If normal, the product of the cell-derived nucleic acid molecule can be considered redundant.

According to the present invention, cell-derived nucleic acid molecules, in particular GSE nucleic acid molecules, can be used to design polypeptides or peptides capable of inhibiting HIV infection. A method to test inhibitory polypeptides or peptides for use as a therapeutic compound can include the steps of (a) delivering a putative inhibitory peptide to a cell susceptible to HIV infection; and (b) determining the ability of such peptide to inhibit HIV infection. Methods to deliver and determine HIV infection are disclosed herein.

One preferred embodiment of the present invention is the use of protective compounds of the present invention to protect an animal from HIV infection. Preferred protective compounds of the present invention have been disclosed herein. Additional protection can be obtained by administering additional protective compounds, including other reagents known to inhibit HIV infection.

A protective compound comprising a cell-derived nucleic acid molecule can be transferred into any HIV-susceptible host cells such as $CD4^+T$ cells or hematopoietic progenitor cells such as $CD34^+$ cells obtained from bone marrow or mobilized peripheral blood, by any DNA transfer techniques well known in the art such as electroporation, transfection or transduction, followed by transplantation of the cells into a recipient. When the cell-derived nucleic acid molecule-containing progenitor cells differentiate in vivo, the progeny cells express the nucleic acid molecule product and become resistant to HIV. Preferably, such cell-derived nucleic acid molecule is a GSE nucleic acid molecule of the present invention.

Alternatively, a cell-derived nucleic acid molecule can be directly administered in vivo using a gene therapy expression vector. In particular, the molecules can be delivered or transferred into $CD4^+T$ cells in both HIV-infected or uninfected individuals to protect against development of HIV infection. The recombinant molecules can also be transferred into stromal cells, including macrophages.

Alternatively, a cell-derived nucleic acid molecule can be delivered into a target cell by a non-viral delivery system. For example, a GSE nucleic acid molecule can be reconstituted into liposomes for delivery to susceptible cells. Liposomes are spherical lipid bilayers with aqueous interiors. All molecules that are present in an aqueous solution at the time of liposome formation (in this case, oligonucleotides) are incorporated into this aqueous interior. The liposomal contents are both protected from the external microenvironment and, because liposomes fuse with cell membranes, are efficiently delivered into the cell cytoplasm, obviating the need to neutralize the oligonucleotides negative charge.

Methods for introducing cell-derived nucleic acid molecules into cells or tissues include the insertion of naked nucleic acid molecule, i.e. by injection into tissue, the introduction of a GSE in a cell ex vivo, i.e., for use in autologous cell therapy, the use of a vector such as a virus, retrovirus, phage or plasmid, etc. or techniques such as electroporation which can be used in vivo or ex vivo.

Protective compounds of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. For systemic administration, route of injection include, but are not limited to, intramuscular, intravenous, intraperitoneal, and subcutaneous. The cell-derived nucleic acid molecules of the invention are formulated in aqueous solutions, preferably in physiologically compatible buffers such as Hanks's solution, Ringer's solution, or physiological saline buffer. In addition, the cell-derived nucleic acid molecules can be formulated in solid or lyophilized form, then redissolved or suspended immediately prior to use.

Protective compounds that inhibit the expression of genes encoding NADH dehydrogenase, 2-oxoglutarate dehydrogenase, M2-type pyruvate kinase/cytosolic thyroid hormone binding protein, calnexin, ADP-ribosylation factor 3, eukaryotic initiation factor 3, protein tyrosine phosphatase, herpesvirus-associated ubiquitin-specific protease, eukaryotic initiation factor 4B, CD44, phosphatidyl-inositol 3 kinase, elongation factor 1 alpha, bone morphogenic protein-1, double-strand break DNA repair gene protein, rat guanine nucleotide releasing protein, anti-proliferative factor (BTG-1), lymphocyte-specific protein 1, protein phosphatase 2A, squalene synthetase, eukaryotic release factor 1, GTP binding protein, importin beta subunit, cell adhesion molecule L1, U-snRNP associated cyclophilin, recepin, Arg/Abl interacting protein (ArgBP2A), keratin related protein, p18 protein, p40 protein, glucosidase II, alpha enolase, macrophage inflammatory protein 1 alpha, tumor protein translationally-controlled 1 (TCTP1), BBC1, Nef interacting protein, Na+-D-glucose cotransport regulator gene protein, hsp90 chaperone protein, FK506-binding protein A1, Rox, beta signal sequence receptor, tumorous imaginal disc protein, cell surface heparin binding protein, SHIP, GNB2L1, ArgRS, ABC Transporter, CDC42, Csa-19, FYN, CTSB, cathepsin L and GLRX, as well as inhibitors of their encoded products, can be administered to a human patient in need of such treatment, by themselves, or in pharmaceutical compositions where an inhibitor is mixed with suitable carriers or excipient(s). A therapeutically effective dose refers to that amount of the compound sufficient to result in an inhibition of HIV infection as compared to the pre-treatment condition. Techniques for formulation and administration of the compounds of the instant application can be found in "Remington's Pharmaceutical Sciences," Mack Publishing Co., Easton, Pa.

Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections. Alternatively, one can administer the compound in a local rather than systemic manner, for example, via injection of the compound directly into a specific tissue, often in a depot or sustained release formulation.

Furthermore, one can administer the compound in a targeted drug delivery system, for example, in a liposome and/or conjugated with a cell-specific antibody. The liposomes and cell-specific antibody will be targeted to and taken up selectively by HIV-infected cells.

The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention can be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity. Additionally, the compounds can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the compounds for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, ogelatin, and polymers such as polyethylene glycols.

The compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the EC50 (effective dose for 50% increase) as determined in cell culture, i.e., the concentration of the test compound which achieves a half-maximal inhibition of HIV replication as assayed by the infected cells to retain CD4 expression, to reduce viral p24 or gp120, and to prevent syncytia formation. Such information can be used to more accurately determine useful doses in humans.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p.1).

Dosage amount and interval can be adjusted individually to provide plasma levels of the active moiety which are sufficient to maintain the inhibitory effects. Usual patient dosages for systemic administration range from 100–2000 mg/day. Stated in terms of patient body surface areas, usual dosages range from 50–910 mg/m$^2$/day. Usual average plasma levels should be maintained within 0.1–1000 $\mu$M. In cases of local administration or selective uptake, the effective local concentration of the compound can not be related to plasma concentration.

The amount of composition administered will, of course, be dependent on the subject being treated, on the subject's body surface area, the severity of the affliction, the manner of administration and the judgment of the prescribing physician.

The following examples are provided for the purposes of illustration and are not intended to limit the scope of the present invention. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

EXAMPLES

Example 1

This example describes isolation and identification of human cell-derived GSEs exhibiting HIV-suppressive activities.

A. Construction of RFE Libraries

Two RFE libraries were constructed from cDNAs of two human cell lines according to the method described by Gudkov et al. (1994, Proc. Natl. Acad. Sci. USA 91:3744). The cDNA prepared from HL-60 cells and HeLa cells was partially digested with DNase I in the presence of Mn$^{++}$ (Sambrook et al., 1989, Molecular Cloning: a Laboratory Manual, Cold Spring Harbor Laboratory, N.Y.). Under these conditions, DNase I is known to produce mostly double-stranded breaks.

The resulting fragments were repaired with the Klenow fragment of DNA polymerase I and T4 polymerase and ligated to synthetic double-stranded adaptors. The 5' adaptors (SEQ ID NOS: 21 and 22) were:

5'-CTCGGAATTCAAGCTTATGGATGGATGG-3'

3'-CCTTAAGTTCGAATACCTACCTAC-5'

The 3' adaptors (SEQ ID NOS: 23 and 24) were:

5'TGAGTGAGTGAATCGATGGATCCGTCT-3'

3'-ACTCACTCACTTAGCTACCTAGGCAGATCCT-5'

In the case of the library made from HL-60 cells, mRNA from uninduced cells was first subtracted from mRNA from cells induced with TNF-α. The subtracted HL-60 library represents a modification of the procedure described in Coche et al., 1994, Nucleic Acids Res. 22:1322–1323. The tracer mRNA was purified from HL-60 cells containing the LNCX plasmid at different time points after induction with TNF-α. The LNCX gene was used as an internal standard to monitor the enrichment of the sequences present in the tracer after subtraction. The mRNAs isolated from induced and uninduced cells were annealed separately to oligo dT magnetic beads (available from Dyna) and the first cDNA strand was synthesized using reverse transcriptase and oligo dT as the primer. The RNA strand was hydrolyzed and the second strand was synthesized on the induced population using a primer containing three ATG codons and 10 random nucleotides on the 3' end. Single stranded cDNA fragments were annealed to an excess of driver cDNA attached to the magnetic beads. This procedure was repeated several times until substantial enrichment in the spiked LNCX sequence was seen. The final population of single-stranded DNA (ssDNA) molecules was amplified using primers with three TGA codons in all three reading frames with 10 random nucleotides on the 3' end. The resulting population of cDNA fragments were cloned into LNCX. This step was taken to enrich for mRNA encoded by cellular genes that might be important in supporting certain stages of the HIV life cycle in order to compensate for the low efficiency of retroviral transfer into OM10.1 cells. This library was represented by $10^6$ recombinant clones.

The random fragments of cDNA from HeLa cells were subjected to a normalization procedure to provide for uniform abundance of different DNA sequences (Gudkov and Roninson, 1997, *Methods in Molecular Biology* 69:221, Humana Press, Inc., Totowa, N.J.). This procedure was used to increase the probability of isolating GSEs from rare cDNAs, since total polyA$^+$ RNA was a mixture of unequally-represented sequences. In brief, the method first denatured 20 Φg of cDNA by boiling for 5 min. in 25 ΦL of TE buffer, followed by immediate cooling on ice. Then, 25 ΦL of 2×hybridization solution was added, and the mixture was divided into four aliquots in Eppendorf tubes, 12.5 ΦL each. One to two drops of mineral oil were added to each sample to avoid evaporation, and the tubes were placed into a 68EC water bath for annealing. One tube was frozen every 12 hours. After the last time-point, each of the annealing mixtures was diluted with water to a final volume of 500 ΦL and subjected to hydroxylapatite (HAP) chromatography. HAP suspension equilibrated with 0.01 M phosphate-buffered saline (PBS) was placed into Eppendorf tubes so that the volume of HAP pellet was approximately 100 ΦL. The tubes with HAP and all the solutions used below were preheated and kept at 65EC. The excess of PBS was removed, and diluted annealing solution was added. After mixing by shaking in a 65EC water bath, the tubes were left in the water bath until HAP pellet was formed (a 15-s centrifugation was used to collect the pellet without exceeding 1000 g in the microcentrifuge to avoid damage of HAP crystals). The supernatant was carefully replaced with 1 mL of preheated 0.01 M PBS, and the process was repeated. To elute the ssDNA, the HAP pellet was suspended in 500 ΦL of PBS at the single-strand elution concentration determined, e.g., 0.16M, the supernatant was collected, and the process was repeated. The supernatants were combined and traces of HAP were removed by centrifugation. The ssDNA was concentrated by centrifugation, and washed three times using 1 mL of water on Centricon-100. The isolated ssDNA sequences were amplified by PCR with the sense primer from the adapter, using a minimal number of cycles to obtain 10 Φg of the product. The size of the PCR product that remained within the desired range (200–500 bp) was ascertained. The normalization quality was tested by Southern or slot-blot hybridization with $^{32}$P-labeled probes for high, moderate- and low-expressing genes using 0.3–1.0 Φg of normalized cDNA/lane. α-actin and α-tubulin cDNAs were used as probes for high-expressing genes, c-myc and topo II cDNAs for moderately-expressing genes, and c-fos cDNA for low-expressing genes. The cDNAs isolated after different annealing times were compared with the original unnormalized cDNA. The probes were ensured to have a similar size and specific activity. The best-normalized ssDNA fraction was used, which produced the most uniform signal intensity with different probes, for large-scale PCR amplification to synthesize at least 20 μg of the product for cloning. More ssDNA template was used to obtain the desired amount by scaling up the number of PCR or the reaction volume.

After normalization, the mixture of fragments ligated to adaptors was digested with BamHI and EcoRI, column purified and ligated to the retroviral vector pLNCX (Miller and Rosman, 1989, *BioTechniques* 7:980–990) or pLNG-FRM cut with EcoRI and BamHI. The pLNGFRM vector is the same as the pLNCX vector except that the neo$^r$ gene has been replaced with a truncated low-affinity NGFR gene. The cells transduced with pLNGFRM express the truncated receptor on their surface which can be easily selected by an anti-NGFR antibody and FACS. The ligation mixture was transformed into *E. coli*. The total plasmid was purified from ~100,000 recombinant clones. The size distribution of the cloned fragments was tested by PCR amplification using primers derived from the vector sequences adjacent to the adapters.

B. Cell Lines and Reagents

The OM101.1 cells are available from the American Type Culture Collection, Manassas, Va. as CRL 10850 (Butera, U.S. Pat. No. 5,256,534). The CEM-ss cells are available from the NIH AIDS Research and Reference Reagent Program as Cat. No. 776. HIV-$1_{SF2}$ is available from NIH AIDS Research and Reference Reagent Program as Cat. No. 275. HL-60 cells are available from American Tissue Culture Collection as CCL 240. HIV-$1_{IIIB}$ is available from AIDS Program as Cat. No. 398.

The anti-CD4 (Q4120PE) and anti-p24 (KC-57 FITC) antibodies were purchased from Sigma and Coulter, respectively. TNF-á was obtained from Boehringer Mannheim. G418 was purchased from Gibco/BRL as Geneticin. The anti-NGFR antibody was obtained from the ATCC (HB-8737) as hybridoma 20.4 (U.S. Pat. Nos. 4,786,593 and 4,855,241). Two anti-CD4 antibodies (L77 and L120) were obtained from Becton Dickenson.

C. Transduction and Selection of GSEs

The libraries prepared from HL-60 cells according to the method of Section A of this Example, were transfected into the packaging cell line, PA317 (ATCC CRL #9078), and converted into retrovirus for infection of OM10.1 cells. Libraries in pLNCX vector were co-cultured and selected with G418. Libraries in pLNGFRM vector were transduced by spinoculation (centrifugation of target cells at 1200×g for 90 min. in the presence of filtered retroviral supernatant; Dunn et al., 1999, *Gene Therapy* 6: 133–137) and selected by FACS sorting of the NGFR$^+$ population. After selection, the OM10.1 cells harboring the entire RFE library were induced with 10 U/mL of TNF-α at 37EC, and 24 hours later, were stained with an antibody and sorted for CD4 expression. Genomic DNA from the CD4$^+$ cells was purified and used for PCR amplification of inserts with the vector-derived primers. The amplified mixture was digested with EcoRI and BamHI and cloned back into the retroviral vector. The selection was repeated for additional rounds.

Additionally, a normalized RFE library made from HeLa cells was transferred into CEM-ss cells and the neo resistant population was infected with TCID$_{50}$ of 3000/$10^6$ cells of HIV-$1_{IIIB}$. This RFE library was represented by 50×10$^6$ independent recombinant clones. Four and seven days after infection, a purified anti-CD4 monoclonal antibody, L77 (available from Becton Dickinson), was added at 5 Φg/mL to prevent syncytia formation. Syncytia formation is thought to be prevented by blocking the interaction between gp120 expressed on the surface of an infected cell and CD4 on the surface of an uninfected cell. Antibody L77 does not prevent HIV infection of a cell. At 10–12 days after infection, CD4+, p24− cell population representing uninfected cells were sorted. Genomic DNA from the CD4+, p24− cells was purified and used for PCR amplification of inserts with the vector-derived primers. The amplified mixture was digested with EcoRI and BamHI and cloned back into the retroviral vector. The selection was repeated for additional rounds.

D. Immunofluorescence and Flow Cytometry

For the immunofluorescent staining of CD4+ cells for selection, $10^7$ cells were washed twice with Assay Buffer (500 mL PBS, 1 mL of 0.5 mM of EDTA at pH 8, 0.5 mL of 10% sodium azide and 10 mL of fetal bovine serum), and resuspended in 500 ΦL PBS to which 50 ΦL of anti-CD4 antibody (Q4120 PE, available from Sigma, St. Louis, Mo.) was added. After incubation at 4EC for 30 min., 5 mL of Assay Buffer was added and the cells centrifuged at 1200 rpm for 4 min. The cells were washed twice with Assay Buffer before sorting by FACS. The aforementioned procedure was performed under sterile conditions.

In order to determine p24 expression in HIV-infected cells, the cells were first washed twice with Assay Buffer. About $10^6$ cells were suspended in 100 μL Assay Buffer, mixed with 2 mL of Ortho PermeaFix Solution (available from Ortho Diagnostics), and incubated for 40 min. at room temperature. After centrifugation at 1200 rpm for 4 min. at 4EC, the cells were resuspended in 2 mL Wash Buffer (500 mL PBS, 25 mL fetal bovine serum, 1.5% bovine serum albumin and 0.0055% EDTA) for 10 min. at room temperature. After centrifugation, the cells were resuspended in 50 ΦL Wash Buffer and mixed with 1:500 dilution of an $IgG_{2a}$ antibody for 20 min. at 4EC, followed by incubation with 5–10 ΦL of anti-p24 antibody (KC57-FITC, available from Coulter) for 30 min. at 4EC. The cells were then washed twice with Wash Buffer and analyzed by flow cytometry.

For the selection of NGFR+ cells, $10^7$ cells were washed twice with Assay buffer and resuspended in 200 ΦL Assay buffer plus 5% normal mouse serum, and 2 mL of anti-NGFR-PE antibody was added. After incubation at 4EC for 30 min., 5 mL of Assay buffer was added and the cells were centrifuged at 1200 rpm for 4 min. The cells were washed twice with Assay buffer before sorting by FACS.

E. Recovery of GSEs and Sequence Analysis

Genomic DNA was isolated from the selected population of OM10.1 or CEM-ss cells harboring putative GSEs by resuspending the cell pellet in 0.1% Triton X-100, 20 Φg/mL proteinase K in 1×PCR buffer, incubating at 55EC for 1 hour, and boiling for 10 minutes. Genomic DNA was used for PCR amplification using vector-derived primers, cloned into the retroviral vector, and transformed into *E. coli* using techniques well known in the art. Individual plasmids were purified from *E. coli* clones using QIAGEN plasmid kits. Inserts were sequenced by the dideoxy procedure (available from AutoRead Sequencing Kit, Pharmacia Biotech) and run on a Pharmacia LKB A.L.F. DNA sequencer. Sequences were analyzed using the DNASTAR program.

F. Identification of GSEs

Figure 1:
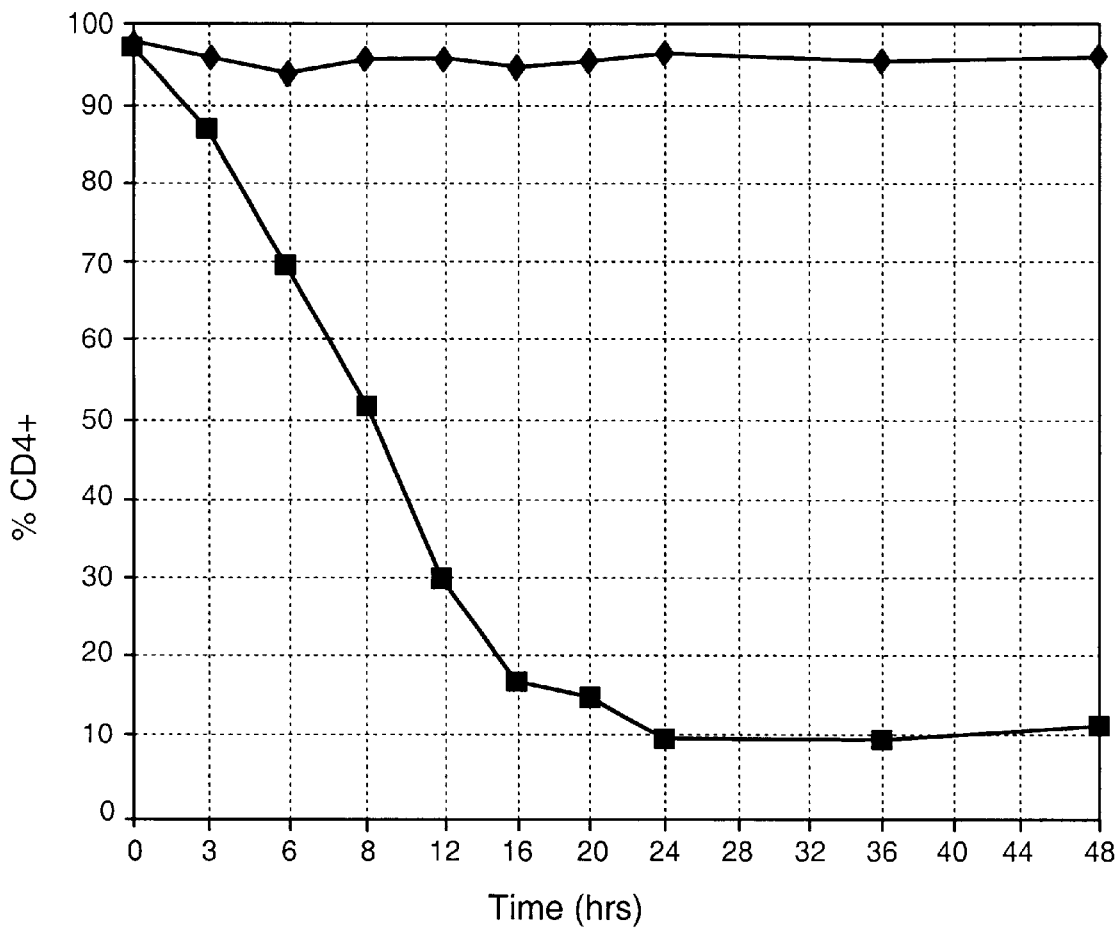
FIG. 1 illustrates the percentage of CD4$^+$ OM10.1 cells that diminish after TNF-α induction; TNF-induced cells, -■-; uninduced cells, -♦-.

Two selection strategies were used to isolate human cell-derived GSEs with HIV-suppressive activities from RFE libraries. One strategy selected for GSEs which suppressed productive infection of cells by HIV. The second strategy selected for GSEs which suppressed induction of the latent provirus in OM10.1 cells. When OM10.1 cells were treated with TNF-α and stained with an antibody specific for the cell surface molecule CD4, a rapid loss of CD4 expression was observed (FIG. 1). In contrast, the vast majority of the uninduced OM10.1 cells retained CD4 expression. It is believed that activation of the latent virus in OM10.1 cells by TNF-α leads to the production of viral protein gp120, which binds to cytoplasmic CD4, thereby preventing its translocation to the cell surface. A diminution of CD4+ OM10.1 cells also correlates with an increased production of viral protein p24 in the cells following TNF-α induction.

GSEs derived from cDNAs representing expressed human cellular genes were identified and isolated from a RFE library made from HL-60 cells using HIV provirus activation in OM10.1 cells as a read-out. Following transfection of the entire library into a packaging cell line, retrovirus carrying the library was used to infect OM10.1 cells by co-cultivation or spinoculation, and NGFR selection was performed to ensure the retention of the viral vector. When the infected cells were treated with TNF-α a small number of residual CD4+ cells were detected by an anti-CD4 antibody and sorted by FACS. The GSEs contained in these cells were recovered by PCR amplification and their nucleotide sequences determined.

Figure 2:
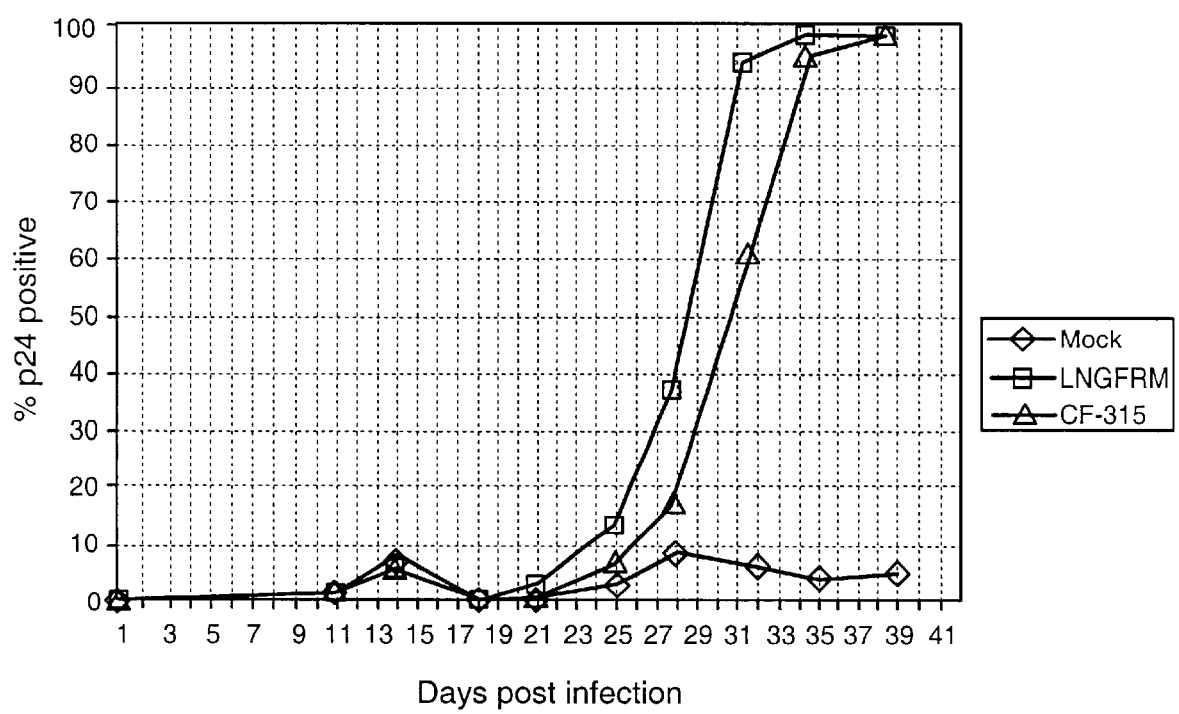
FIG. 2 illustrates the percentage of intracellular p24$^+$ CEM-ss cells containing the CF-315 sequence (SEQ ID NO:1) after infection with HIV-1$_{SF2}$ at a TCID$_{50}$ of 1000. CEM-ss cells (10$^6$) containing the C-315 construct or control vector DNA (denoted as LNGFRM) were harvested on the indicated days post infection, stained with FITC-conjugated anti-p24 monoclonal antibody and analyzed by flow cytometry. Mock infected cells, -◇-; LNGFRM vector-infected cells, -□-; and C-315 infected cells, -△-.

A total of twenty GSEs were isolated by the two aforementioned selection strategies using OM10.1 and CEM-ss cells. Six of these GSEs were shown to have substantial sequence identity with cDNAs of genes encoding different subunits of the NADH dehydrogenase enzyme complex. For example, CF-315 (SEQ ID NO:1) is a GSE which suppresses HIV replication as an antisense molecule, which in its sense orientation has sequence identity with a gene encoding a subunit, ND6, of a mitochondrial enzyme, NADH dehydrogenase (Chomyn et al., 1988, *Science* 234:614). CF-315 was further shown to protect uninfected human T cells from a productive HIV-1 infection (FIG. 2). In this experiment, the retroviral vector, pLNGFRM, containing the CF-315 nucleic acid molecule was transferred into CEM-ss cells followed by NGFR selection. Vector containing plasmid DNA (denoted LNGFRM) was used as negative control. The NGFR+ cells were 99% CD4+, and they were then infected with $TCID_{50}$ of 1000 of HIV-$1_{SF2}$. The infected cells were removed at 11, 14, 18, 21, 25, 28, 32, 35 and 39 days after infection, and stained with a fluorescinated-anti-p24 antibody as an indicator of HIV infection. FIG. 2 shows that CF-315 inhibited infection of human T cells by HIV-$1_{SF2}$, as compared with negative control of vector plasmid DNA.

CF-319 (SEQ ID NO:2) is a GSE which suppresses HIV replication in the sense orientation and has substantial sequence identity with another portion of the gene encoding the ND6 subunit of NADH dehydrogenase. CF-101 (SEQ ID NO:3) also exhibits its HIV-suppressive activities in the sense orientation and has substantial sequence identity with a gene encoding the ND2 subunit of NADH dehydrogenase (Chomyn et al., 1985, *Nature* 314:592). CF-117 (SEQ ID NO:4) suppresses HIV activities as an antisense molecule, and in its sense orientation, it has substantial sequence identity with a gene encoding the ND6 subunit of NADH dehydrogenase. CF-025 (SEQ ID NO:5) suppresses HIV infection as an antisense molecule, and in its sense orientation, it has substantial sequence identity with a gene encoding the ND2 subunit of NADH dehydrogenase. CF-128 (SEQ ID NO:6) suppresses HIV infection in the sense orientation and it has substantial sequence identity with a gene encoding the ND4 subunit of NADH dehydrogenase.

Since both selection strategies produced GSEs having substantial sequence identity with different subunits of NADH dehydrogenase, this enzyme complex plays an important role during HIV infection, and thus, methods to down-regulate the expression of this complex or any of its subunits can be used to inhibit HIV replication in infected cells.

The selection of GSEs from HeLa cell library using productive infection of CEM-ss cells isolated twelve additional nucleic acid molecules which have substantial sequence identity with other cellular genes. CF-004 (SEQ ID NO:7) suppresses HIV infection as a sense molecule and has substantial sequence identity with a gene encoding human 2-oxoglutarate dehydrogenase (Koike, 1995, *Gene* 158:261–266; Koike et al., 1992, *Proc. Natl. Acad. Sci. USA* 89:1963–1967). CF-113 (SEQ ID NO:8) suppresses HIV infection as a sense molecule and has substantial sequence identity with a gene encoding human M2-type pyruvate kinase/cytosolic thyroid hormone binding protein (Kato et al., 1989, *Proc. Natl. Acad. Sci. USA* 86:7861–7865). CF-204 (SEQ ID NO:9) suppresses HIV infection as an antisense molecule, and in its sense orientation, it has substantial sequence identity with a gene encoding human calnexin (David et al., 1993, *J. Biol. Chem.* 268:9585–9592). CF-001 (SEQ ID NO:10) suppresses HIV infection as an antisense molecule, and in its sense orientation, it has substantial sequence identity with a gene encoding human ADP-ribosylation factor 3 (Tsai et al., 1991, *J. Biol. Chem.* 266:23053–23059). CF-273 (SEQ ID NO: 11) suppresses HIV infection as a sense molecule and has substantial sequence identity with a gene encoding human eukaryotic translation initiation factor 3 (Merrick and Hershey, 1996, *Translational Control*, Cold Spring Harbor, N.Y., pp. 31–69). CF-311 (SEQ ID NO: 12) suppresses HIV infection as an antisense molecule, and in its sense orientation, it has substantial sequence identity with a gene encoding a human protein tyrosine phosphatase (Kim et al., 1996, *Oncogene* 13:2275–2279). CF-313 (SEQ ID NO: 13) suppresses HIV infection as a sense molecule and has substantial sequence identity with a gene encoding a human protein tyrosine phosphatase (Keyse and Emslie, 1992, *Nature* 359:644–647). CF-210 (SEQ ID NO: 14) suppresses HIV infection as a sense molecule and has substantial sequence identity with a gene encoding herpesvirus-associated ubiquitin-specific protease (Everett et al., 1997, *EMBO J.* 16:566–577). CF-266 (SEQ ID NO: 15) suppresses HIV infection as an antisense molecule, and in its sense orientation, it has substantial sequence identity with a gene encoding human eIF4B (Milburn et al., 1990, *EMBO J.*, 9:2783–2790). CF-302 (SEQ ID NO: 16) suppresses HIV infection as an antisense molecule, and in its sense orientation, it has substantial sequence identity with a gene encoding human CD44 (Stamenkovic et al., 1991, *EMBO J.* 10:243–248). CF-317 (SEQ ID NO: 17) suppresses HIV infection as an antisense molecule, and in its sense orientation, it has substantial sequence identity with a gene encoding human phosphatidylinositol 3-kinase (Volinia et al., 1995, *EMBO J.* 14:3339–3348). CF-286 (SEQ ID NO: 18) suppresses HIV infection as a sense molecule and has substantial sequence identity with a gene encoding human elongation factor-1α (Uetsuki et al., 1989, *J. Biol. Chem.* 264:5791–5798).

In addition, two isolated GSEs did not share sequence homology with any known genes by sequence comparison. CF-061 (SEQ ID NO: 19) was selected in OM10.1 cells. CF-280 (SEQ ID NO: 20) was selected in CEM-ss cells. These two nucleic acid molecules represent portions of unknown human cellular genes which play a role in supporting HIV infection.

Figure 3:
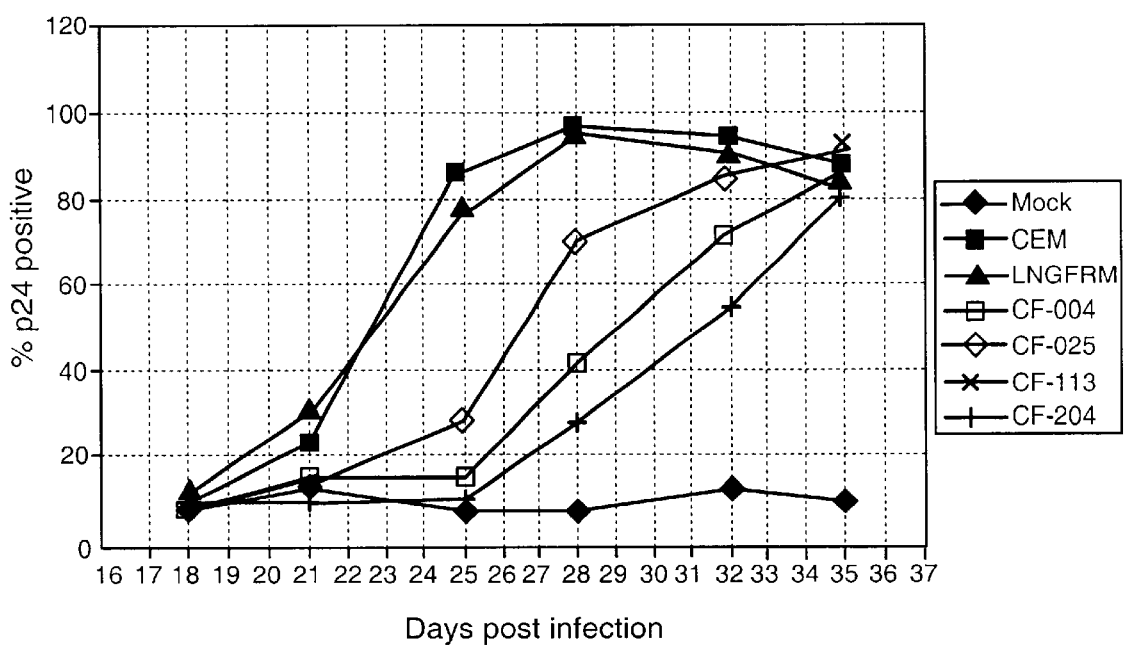
FIG. 3 illustrates the percentage of intracellular p24$^+$ CEM-ss cells containing various GSEs: CF-004 (SEQ ID NO:7), CF-025 (SEQ ID NO:5), CF-113 (SEQ ID NO:8) and CF-204 (SEQ ID NO:9) after infection with HIV-1$_{SF2}$ at a TCID$_{50}$ of 1000. Controls include mock-infected, vector (LNGFRM)-infected and HIV-infected CEM-ss cells.
Figure 4:
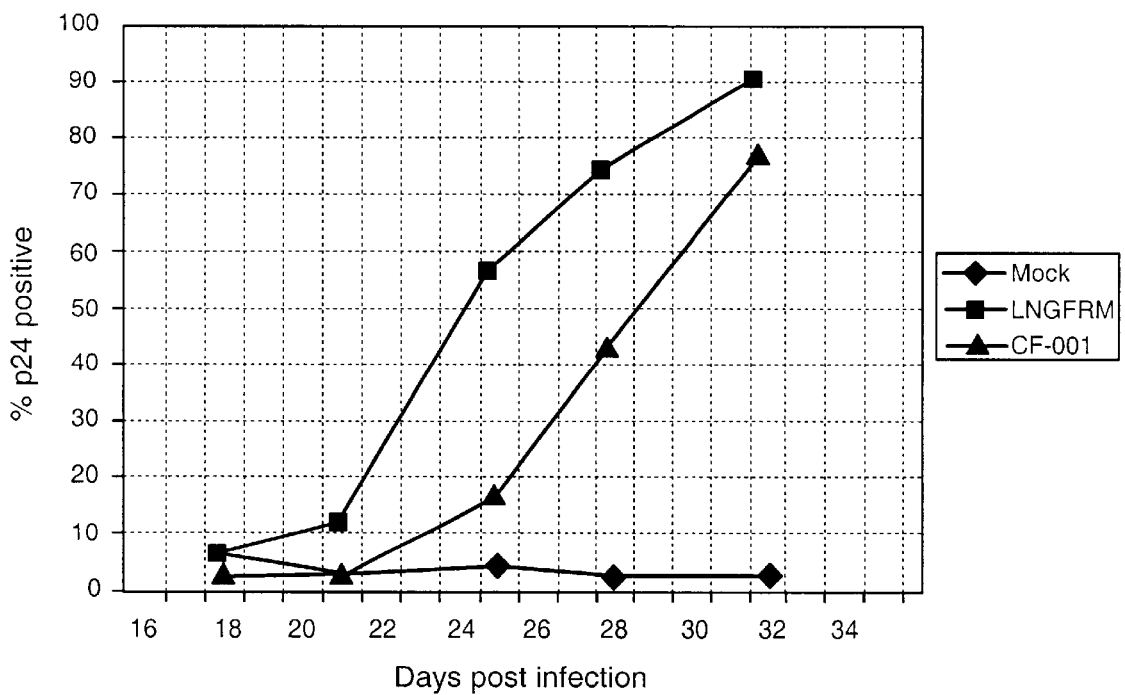
FIG. 4 illustrates the percentage of intracellular p24$^+$ CEM-ss cells containing CF-001 (SEQ ID NO:10) after infection with HIV-1$_{SF2}$ at a TCID$_{50}$ of 1000. Controls include mock-infected and vector (LNGFRM)-infected cells.

FIG. 3 shows the ability of four exemplary GSEs mentioned above in preventing productive infection of CEM-ss cells by HIV. While the GSEs were isolated as fragments of distinct cellular genes, they all inhibited HIV infection as shown by a reduction of p24 levels in the infected cells when compared with controls. Additionally, FIG. 4 shows the HIV-suppressive activities of CF-001 which functions as an antisense molecule.

The selection of GSEs from a HeLa cell library using productive infection of CEM-ss cells isolated 21 additional nucleic acid molecules which have substantial sequence identity with other cellular genes. CF-537 (SEQ ID NO:25) is a GSE that interferes with the HIV life cycles in the sense orientation and has substantial sequence identity with a gene encoding human bone morphogenic protein-1 (BMP1–6; Wozney et al., 1988, *Science* 242:1528–1534). The complement of SEQ ID NO:25 is represented by SEQ ID NO:26. CF-320 (SEQ ID NO:27) is a GSE that interferes with HIV infection in the sense orientation and has substantial sequence identity with a gene encoding double-strand break DNA repair gene protein (McKay et al., 1996, *Genomics* 36:305–315). The complement of SEQ ID NO:27 is represented by SEQ ID NO:28. CF-321 (SEQ ID NO:29) is a GSE that interferes with HIV replication in the sense orientation and has substantial sequence identity with a gene encoding rat guanine nucleotide releasing protein (Burton et al., 1993, *Nature* 361: 464–467). The complement of SEQ ID NO:29 is represented by SEQ ID NO:30. CF-322 (SEQ ID NO:31) is a GSE that interferes with HIV replication in the sense orientation and has substantial sequence identity with a gene encoding anti-proliferative factor protein (BTG-1; Rouault et al., 1992, *EMBO J*, 11:1663–1670). The complement of SEQ ID NO:31 is represented by SEQ ID NO:32. CF-332 (SEQ ID NO:33) is a GSE that interferes with HIV replication as an antisense molecule and has substantial sequence identity with a gene encoding lymphocyte-specific protein 1 (Jongstra-Bilen et al., 1990, *J. Immunol.* 144: 1104–1110). The complement of SEQ ID NO:33 is represented by SEQ ID NO:34. CF-335 (SEQ ID NO:35) is a GSE that interferes with HIV replication as an antisense molecule and has substantial sequence identity with a gene encoding protein phosphatase 2A protein (Mayer et al., 1991, *Biochemistry* 30:3589–3597). The complement of SEQ ID NO:35 is represented by SEQ ID NO:36. CF-42 (SEQ ID NO:37) is a GSE that interferes with HIV replication in the sense orientation and has substantial sequence identity with a gene encoding squalene synthetase protein (Summers et al., ibid.). The complement of SEQ ID NO:37 is represented by SEQ ID NO:38. CF-50 (SEQ ID NO:39) also exhibits its HIV-suppressive activities in the sense orientation and has substantial sequence identity with a gene encoding squalene synthetase protein (Summers et al., ibid.). The complement of SEQ ID NO:39 is represented by SEQ ID NO:40. CF-527 (SEQ ID NO:41) is a GSE, a peptide from which interferes with HIV replication, and has substantial sequence identity with a gene encoding Eukaryotic release factor 1 protein (ERF-1; Andjelkovic et al., 1996, *EMBO J.* 15:7156–7167). The complement of SEQ ID NO:41 is represented by SEQ ID NO:42. CF-528 (SEQ ID NO:43) is a GSE that interferes with HIV infection in the sense orientation and has substantial sequence identity with a gene encoding GTP binding protein (Zigman et al., 1993, *Endocrinology* 133:2508–2514). The complement of SEQ ID NO:43 is represented by SEQ ID NO:44. CF-529 (SEQ ID NO:45) is a GSE that interferes with HIV replication as an antisense molecule and has substantial sequence identity with a gene encoding Importin beta subunit protein (Gorlich et al., 1995, *Curr Biol.* 5:383–392). The complement of SEQ ID NO:45 is represented by SEQ ID NO:46. CF-531 (SEQ ID NO:47) is a GSE that interferes with HIV replication as an antisense molecule and has substantial sequence identity with a gene encoding cell adhesion molecule LI protein (LCAM1; Hlavin et al., 1991, *Genomics* 11:416–23). The complement of SEQ ID NO:47 is represented by SEQ ID NO:48. CF-545 (SEQ ID NO:49) is a GSE that interferes with HIV replication as an antisense molecule and has substantial sequence identity with a gene encoding U-snRNP associated cyclophilin protein (Horowitz et al., ibid.). The complement of SEQ ID NO:49 is represented by SEQ ID NO:50. CF-547 (SEQ ID NO:51) is a GSE that interferes with HIV replication as an antisense molecule and has substantial sequence identity with a gene encoding recepin endoprotease protein (GenBank Accession No. U03644). The complement of SEQ ID NO:51 is represented by SEQ ID NO:52. CF-619 (SEQ ID NO:53) is a GSE that interferes with HIV replication in the sense orientation and has substantial sequence identity with a gene encoding Arg/Abl interacting protein (ArgBP2A; GenBank Accession No. AF049884). The complement of SEQ ID NO:53 is represented by SEQ ID NO:54. CF-620 (SEQ ID NO:55) is a GSE that interferes with HIV replication as an antisense molecule and has substantial sequence identity with a gene encoding keratin related protein (IFN-α regulated; Flohr et al., ibid.). The complement of SEQ ID NO:55 is represented by SEQ ID NO:56. CF-624 (SEQ ID NO:57) is a GSE that interferes with HIV replication in a sense orientation and has substantial sequence identity with a gene encoding p18 protein (Zhu et al., ibid.). The complement of SEQ ID NO:57 is represented by SEQ ID NO:58. CF-630 (SEQ ID NO:59) is a GSE that interferes with HIV replication as an antisense molecule and has substantial sequence identity with a gene encoding p40 protein (Mayer et al., 1988, *Biochim Biophys Acta* 1395:301–308). The complement of SEQ ID NO:59 is represented by SEQ ID NO:60. CF-579 (SEQ ID NO:61) is a GSE that interferes with HIV replication in a sense orientation and has substantial sequence identity with a gene encoding glucosidase alpha II protein (GenBank Accession No. AJ000332). The complement of SEQ ID NO:61 is represented by SEQ ID NO:62. CF-287 (SEQ ID NO:77) is a GSE that interferes with HIV replication in a sense orientation and has substantial sequence identity with a gene encoding $Na^+$-D-Glucose cotransport regulator protein (Lambotte et al, 1996, *DNA Cell Biol.* 15:769–77). The complement of SEQ ID NO:77 is represented by SEQ ID NO:78. CF-622 (SEQ ID NO:87) is a GSE that interferes with HIV replication as an antisense molecule and has substantial sequence identity with a gene encoding Rox protein (Meroni et al., 1997, *EMBO J.* 16:2892–2906). The complement of SEQ ID NO:87 is represented by SEQ ID NO:88. H1C-11H9 (SEQ ID NO:99) is a GSE that interferes with HIV replication as an antisense molecule and has substantial sequence identity with a gene encoding human SHIP protein (Ware et al., 1996, ibid.). The complement of SEQ ID NO:99 is represented by SEQ ID NO:100. H1C-16A3 (SEQ ID NO:101) is a GSE that interferes with HIV replication as an antisense molecule and has substantial sequence identity with a gene encoding human GNB2L1 protein (Guillemot et al., 1989, ibid.). The complement of SEQ ID NO:101 is represented by SEQ ID NO:102. H1C-2F9 (SEQ ID NO:103) is a GSE that interferes with HIV replication as an antisense molecule and has substantial sequence identity with a gene encoding ArgRS protein (Girjes et al., 1995, ibid.). The complement of SEQ ID NO:103 is represented by SEQ ID NO:104. H1C-13D2 (SEQ ID NO:105) is a GSE that interferes with HIV replication as an antisense molecule and has substantial sequence identity with a gene encoding human ABC Transporter protein (Stanchi, F., 1998, ibid.). The complement of SEQ ID NO:105 is represented by SEQ ID NO: 106. H1C-4A8 (SEQ ID NO:107) is a GSE that interferes with HIV replication as an antisense molecule and has substantial sequence identity with a gene encoding human CDC42 protein (Shinjo et al., 1990, ibid.). The complement of SEQ ID NO:107 is represented by SEQ ID NO:108. H1C-6G11 (SEQ ID NO:109) is a GSE that interferes with HIV replication as an antisense molecule and has substantial sequence identity with a gene encoding human Csa-19 protein (Fisicaro et al., 1995, ibid.). The complement of SEQ ID NO:109 is represented by SEQ ID NO:110. H1C-16E3 (SEQ ID NO:111) is a GSE that interferes with HIV replication as an antisense molecule and has substantial sequence identity with a gene encoding FYN protein (da Silva et al., 1997, ibid.). The complement of SEQ ID NO:111 is represented by SEQ ID NO:112. H1C-23G2 (SEQ ID NO:113) is a GSE that interferes with HIV replication as an antisense molecule and has substantial sequence identity with a gene encoding human CTSB protein (Tam et al., 1994, ibid.). The complement of SEQ ID NO:113 is represented by SEQ ID NO:114. H1C-37E11 (SEQ ID NO:115) is a GSE that interferes with HIV replication as an antisense molecule and has substantial sequence identity with a gene encoding human cathepsin L protein (Gal and Gottesman, 1988, ibid.). The complement of SEQ ID NO:115 is represented by SEQ ID NO:116. H1C-6G5 (SEQ ID NO:117) is a GSE that interferes with HIV replication as an antisense molecule and has substantial sequence identity with a gene encoding human glutaredoxin protein (Park and Levine, 1997, ibid.). The complement of SEQ ID NO:117 is represented by SEQ ID NO:118.

Figure 7:
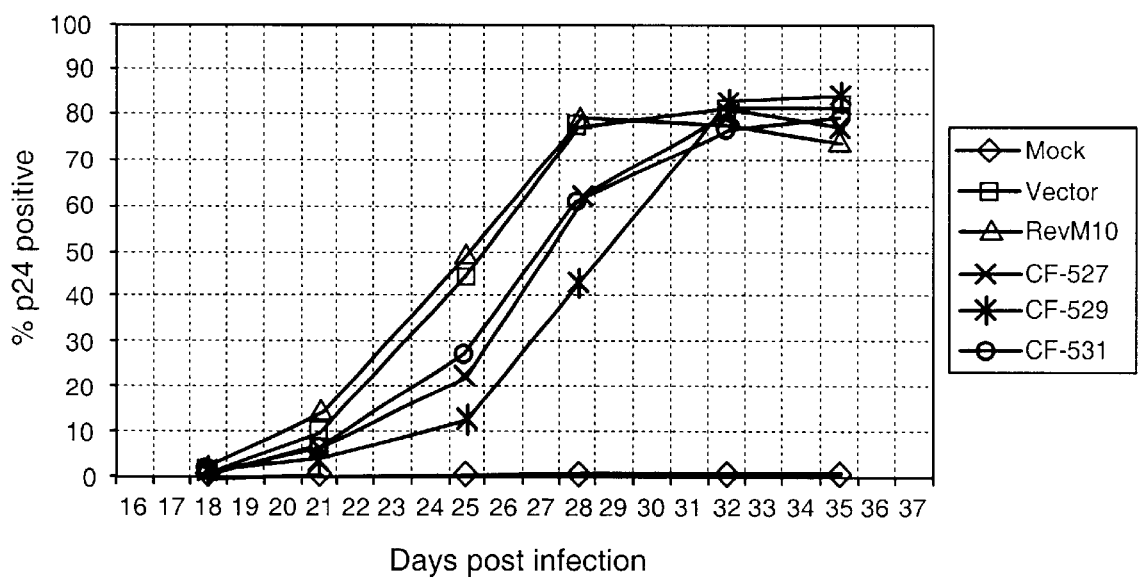
FIG. 7 illustrates the percentage of intracellular p24$^+$ CEM-ss cells containing various GSEs: CF-527 (SEQ ID NO:41), CF-529 (SEQ ID NO:45) and CF-531 (SEQ ID NO:47) after infection with HIV-1$_{SF2}$ at a TCID$_{50}$ of 1000. Controls include mock-infected, vector (LNGFRM)-infected and CEM-ss cells transfected with RevM10.
Figure 8:
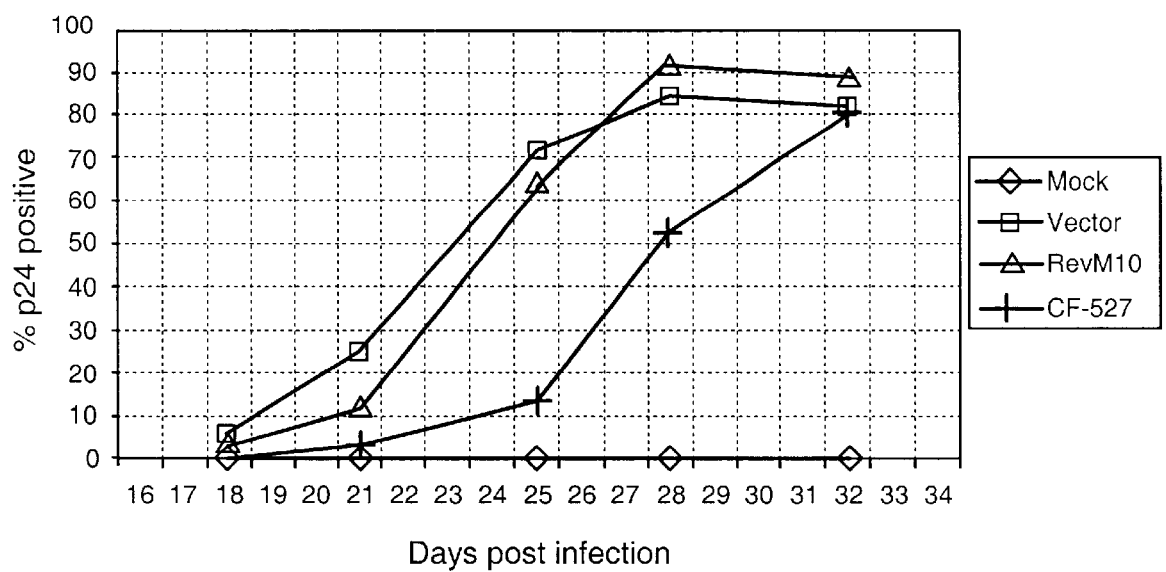
FIG. 8 illustrates the percentage of intracellular p24$^+$ CEM-ss cells containing the GSE CF-579 (SEQ ID NO:61)

FIGS. 7, 8 and 9 show the ability of seven exemplary GSEs mentioned immediately above in preventing productive infection of CEM-ss cells by HIV. While the GSEs were isolated as fragments of distinct cellular genes, they all inhibited HNV infection as shown by a reduction of p24 levels in the infected cells when compared with controls.

Example 2

This Example demonstrates the suppression of HIV infection by NADH dehydrogenase inhibitors NADH dehydrogenase inhibitors, amytal (available from Sigma, St. Louis, Mo.) and mofarotene (Uchida et al., 1994, *Int. J. Cancer* 58:891–897) were diluted in sterile culture medium and used according to the indicated concentrations.

OM10.1 cells were cultured in RPMI 1640 glucose-free media prior to and during incubation with NADH dehydrogenase inhibitors and TNF-á induction. The inhibitors were added to the cells followed by TNF-á induction 1–2 hours later. The expression of CD4 by the cells was assessed by anti-CD4 antibody staining and flow cytometry after 24 hour incubation at 37° C.

Human peripheral blood leukocytes (PBLs) were isolated using Ficoll-Hypaque density gradient separation. Cells were washed twice and resuspended in RPMI+10% FBS+ 2% human AB serum+penicillin/streptomycin/glutamine+ 100 Units/mL of IL-2 at a concentration of $0.5 \times 10^6$ cells/mL. PBLs were then activated with phytohemagglutinin at 0.5 μg/mL and placed in a humidified incubator at 37° C./5% $CO_2$. After two days of activation, $10^6$ cells were infected with HIV-$1_{SF33}$ at $TCID_{50}$ of 1000, in the presence of various concentrations of mofarotene: 0 μM, 1 μM, 0.5 μM, 0.1 μM, and 0.05 μM. A separate set of uninfected samples under identical concentrations of mofarotene were also maintained as controls. The samples were analyzed by flow cytometry at day 4 and day 6 post infection. The cells were gated for CD3 expression (for T cells). Then the expression of CD4 and viral p24 and CD4 was examined by bivariate dot plot.

Figure 5:
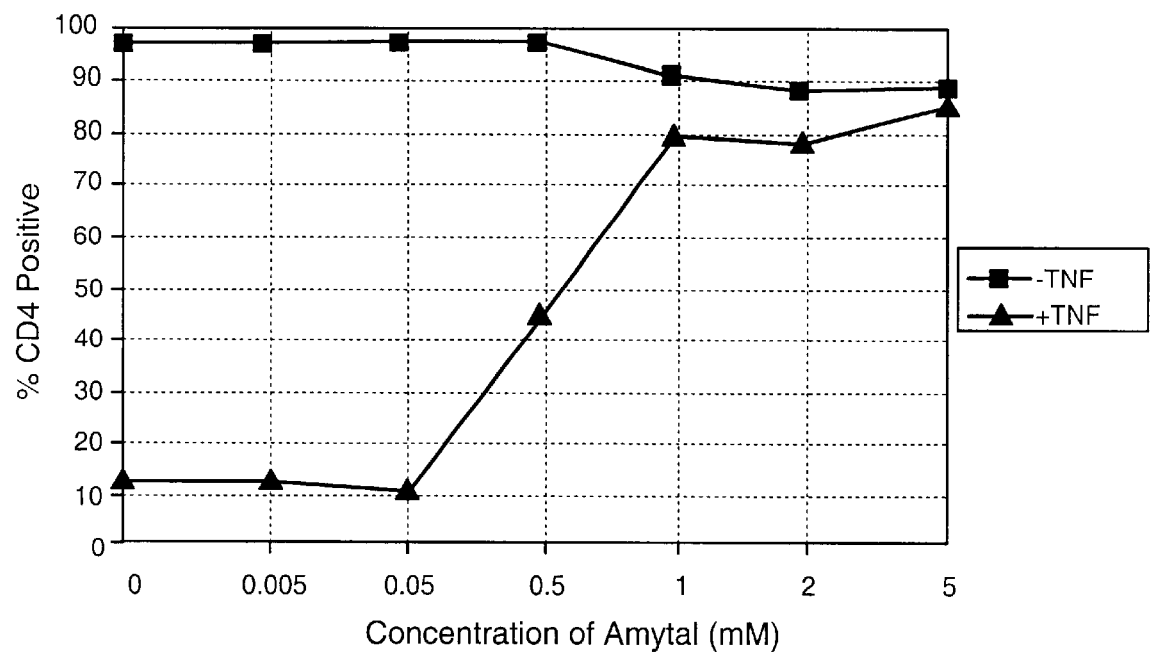
FIG. 5 illustrates the percentage of CD4$^+$ OM10.1 cells after treatment with amytal following TNF-α induction. TNF induction, -▲-; no TNF induction, -■-.
Figure 6:
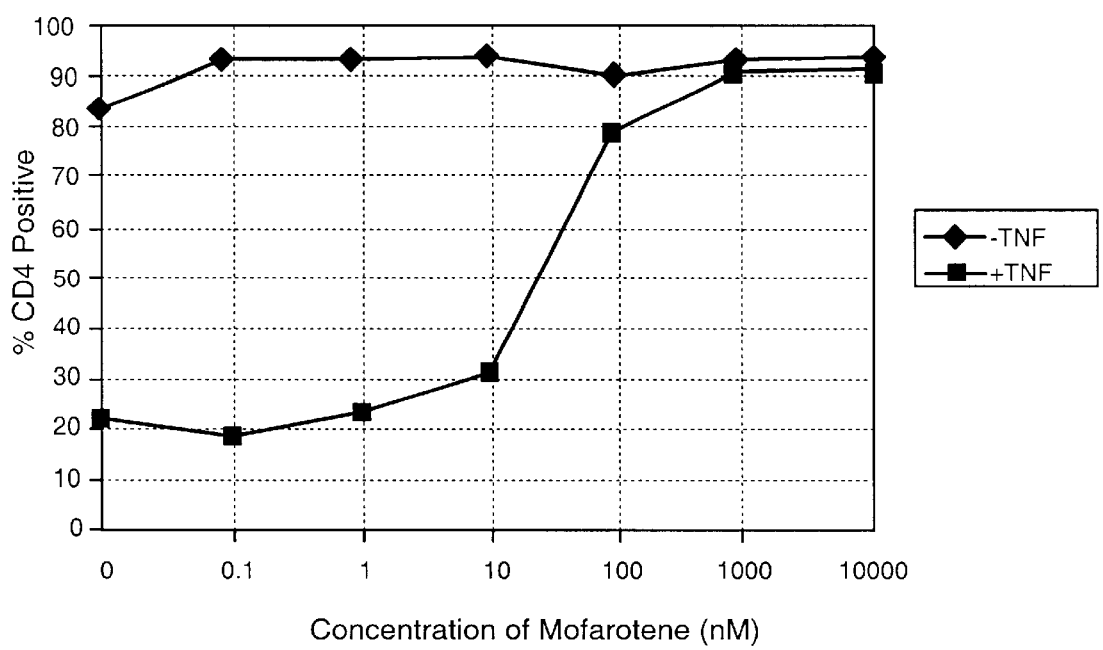
FIG. 6 illustrates the percentage of CD4$^+$ OM10.1 cells after treatment with mofarotene following TNF-α induction. TNF induction, -■-; no TNF induction, -♦-.

Since several GSEs have been selected and shown to have substantial sequence identity with cellular genes which encode different subunits of NADH dehydrogenase, two compounds with known NADH dehydrogenase-inhibitory activities were tested for their ability to suppress HIV infection. FIG. 5 shows that amytal inhibited the induction of latent HIV provirus in OM10.1 cells in a dose-dependent manner, as shown by its ability to retain CD4 expression by TNF-α-induced OM10.1 cells. In the same assay, mofarotene, which down-regulates mitochondrial gene expression, also inhibited HIV-1 induction at even lower concentrations (FIG. 6). At 100 nM of mofarotene, 80% of the cells retained CD4 expression, and greater than 80% of the cells remained viable. In addition, when p24 expression was measured as an indication by HIV infection, both amytal and mofarotene also suppressed intracellular p24 levels in the treated cells as compared with untreated controls.

In order to test the ability of a NADH dehydrogenase inhibitor to prevent productive infection of T cells by HIV, human PBLs were isolated and infected with HIVSF33 in the presence of various concentrations of mofarotene. The $CD3^+$ T cells were analyzed with respect to their expression of CD4 and viral p24 and the results are shown in Table 1.

TABLE 1

| HIV | Mofarotene (μM) | % $CD4^+$ in population | % $p24^-$ in $CD4^-$ T population |
|---|---|---|---|
| − | 1.0 | 36% | 0% |
| − | 0.5 | 34% | 0% |
| − | 0.1 | 34% | 0% |
| − | 0.05 | 33% | 0% |
| − | 0.0 | 32% | 0% |
| + | 1.0 | 25% | 10% |
| + | 0.5 | 24% | 12.5% |
| + | 0.1 | 28% | 11.4% |
| + | 0.05 | 18% | 20.5% |
| + | 0.0 | 15% | 33% |

On day 4 post-infection, there was little detectable difference between PBLs infected with HIV whether or not mofarotene was added. Mafarotene alone did not significantly alter the percentage of $CD4^+$ T cells, nor did it alter the expression level of CD3 on the cell surface.

On day 6, a significant difference was detected with respect to the percentage of $CD4^+$ T cells and percentage of $p24^+CD4^+$T cells. In the HIV-infected sample without mofarotene, 33% of CD4+ T cells were $p24^+$ and only 15% of T cells were $CD4^+$. In the HIV-uninfected control sample, ~32% of T cells were $CD4^+$, suggesting a dramatic depletion of $CD4^+$ T cells by HIV infection. In the HIV-infected sample with 1 ìM of mofarotene, only 10% of $CD4^+$ T cells were $p24^+$. In addition, ~25% of T cells were $CD4^+$, indicating that mofarotene inhibited the depletion of $CD4^+$ T cells by HIV infection. The level of protection by mofarotene, as measured by the percentage of p24+ $CD4^+$ T cells and percentage of $CD4^+$ cells in the $CD3^+$ T cell population, diminished with decreased concentrations of mofarotene. While mofarotene alone increased the percentage of $CD4^+$ T cells in uninfected samples, the effect was minimal (up to 4% higher). At day 6, mofarotene did not alter the expression level of CD3 on the cell surface. Hence, a NADH dehydrogenase inhibitor prevented productive infection by HIV of primary cultures of human T cells.

Example 3

This example describes the production of a PBMC library and isolation of GSEs therefrom.

A. PBMC Library

A cell-derived random fragment library (RFL) was constructed using cDNA from peripheral blood mononuclear cells (PBMC). Four buffy coats were obtained from four healthy blood donors and PBMCs were purified by Ficoll gradient centrifugation followed by stimulation with PHA (1 μg/mL). Cells were removed at 5, 10, and 24 hours after the addition of PHA and total RNA was isolated by Trizol extraction. All time points from all donors were then pooled. Polyadenylated mRNA was purified from the total RNA by passages through an oligo-dT column. cDNA was synthesized from the polyadenylated RNA with random primers using the Gibco Superscript Choice system for cDNA Synthesis (Gibco BRL, Rockville, Md.). The cDNA was normalized using the PCR-Select cDNA Subtraction kit (Clontech, Palo Alto, Calif.) based on the suppression subtractive hybridization methods of Diatchenko et al. (1996, *Proc. Natl. Acad. Sci. USA* 93, 6025–6030, 1996). The primers used for the normalization were:

5'-TAGGGCTCGAGCCGCCACC
    ATG-3'                     (Xho5=S#2; SEQ ID NO:97)

5'-ATCCCTGCAGGTCACTCAC
    TCA-3'                     (Sse3=AS#1; SEQ ID NO:98)

The normalized random fragments were digested with XhoI and Sse83871, purified on quick spin columns (available from Qiagen, Valencia, Calif.) and ligated into the SseI/XhoI site of a bicistronic retroviral vector, EMCVNgfrMPBIN. This vector was based on LXSNgfr as described in Dunn el al. (1999, *Gene Therapy* 6:130–137). Modifications included substitution of the Moloney murine leukemia virus LTR with the hybrid LTR described by Baum et al., 1995, (*J. Virol.* 69:7541–7547) and replacement of the SV40 promoter with encephalomyocarditis virus (EMCV) internal ribosomal entry site isolated from the plasmid, pCITE (available from Amersham, Arlington Heights, Ill.). The ligation mix was then transformed into competent cells. The total plasmid was purified from approximately 50 million clones.

B. Isolation of GSEs

The PBMC library was screened using the methods described above in Section 1F. A total of 14 GSEs were isolated using CEM-ss cells. CF-674 (SEQ ID NO:69) is GSE that interferes with HIV replication in a sense orientation and has substantial sequence identity with a gene encoding human translationally controlled tumor protein 1 (GenBank Accession No. HUMCH13C4A). The complement of SEQ ID NO:69 is represented by SEQ ID NO:70. CF-675 (SEQ ID NO:71) is another GSE that has substantial sequence identity with a gene encoding human translationally controlled tumor protein 1 (GenBank Accession No. HUMCH13C4A). The complement of SEQ ID NO:71 is represented by SEQ ID NO:72. CF-679 (SEQ ID NO:83) is another GSE that has substantial sequence identity with a gene encoding human translationally controlled tumor protein 1 (GenBank Accession No. HUMCH13C4A). The complement of SEQ ID NO:83 is represented by SEQ ID NO:84. CF-693 (SEQ ID NO:75) is GSE that interferes with HIV replication in a sense orientation and has substantial sequence identity with a gene encoding NEF interacting protein (GenBank Accession No. HSU83843). The complement of SEQ ID NO:75 is represented by SEQ ID NO:76. CF-660 (SEQ ID NO:79) is a GSE that interferes with HIV replication as an antisense molecule and has substantial sequence identity with a gene encoding human hsp90 chaperone protein (Rebbe el al., 1989, *J. Biol Chem.* 264:15006–15011). The complement of SEQ ID NO:79 is represented by SEQ ID NO:80. CF-653 (SEQ ID NO:67) is a GSE that interferes with HIV replication as an antisense molecule and has substantial sequence identity with a gene encoding MIP-1 alpha protein (Obata et al., 1988, *J Virol.* 62:4381–4386). The complement of SEQ ID NO:67 is represented by SEQ ID NO:68. CF-676 (SEQ ID NO:63) is a GSE that interferes with HIV replication as an antisense molecule and has substantial sequence identity with a gene encoding alpha enolase protein (Yu et al., 1997, *Genome Res.* 7:353–358). The complement of SEQ ID NO:63 is represented by SEQ ID NO:64. CF-675 (SEQ ID NO:65) is another GSE that has substantial sequence identity with a gene encoding alpha enolase protein. The complement of SEQ ID NO:65 is represented by SEQ ID NO:66. CF-673 (SEQ ID NO:73) is a GSE that interferes with HIV replication as an antisense molecule and has substantial sequence identity with a gene encoding BBC-1 satellite DNA protein (GenBank Accession No. AJ223209). The complement of SEQ ID NO:73 is represented by SEQ ID NO:74. CF-672 (SEQ ID NO:81) is another GSE that interferes with HIV replication as an antisense molecule and has substantial sequence identity with a gene encoding BBC-1 satellite DNA protein. The complement of SEQ ID NO:81 is represented by SEQ ID NO:82. CF-681 (SEQ ID NO:85) is a GSE that interferes with HIV replication as an antisense molecule and has substantial sequence identity with a gene encoding FK506-binding protein A1 (Maki et al, 1990, *Proc. Natl. Acad. Sci. USA* 87:5440–5443). The complement of SEQ ID NO:85 is represented by SEQ ID NO:86. CF-683 (SEQ ID NO:89) is a GSE that interferes with HIV replication as an antisense molecule and has substantial sequence identity with a gene encoding beta-signal sequence receptor protein (Chinen et al., ibid.). The complement of SEQ ID NO:89 is represented by SEQ ID NO:90. CF-684 (SEQ ID NO:91) is a GSE that interferes with HIV replication in a sense orientation and has substantial sequence identity with a gene encoding human tumorous imaginal disc protein (Schilling et. al., ibid.). The complement of SEQ ID NO:91 is represented by SEQ ID NO:92. CF-685 (SEQ ID NO:93) is representative of a cluster of GSEs that interfere with HIV replication as an antisense molecule and has substantial sequence identity with a gene encoding cell surface heparin binding protein (Liu et al., ibid.). The complement of SEQ ID NO:93 is represented by SEQ ID NO:94. Another member of the cluster is CF-686 (SEQ ID NO:95), also having substantial sequence identity with a gene encoding cell surface heparin binding protein (Liu et al., ibid.). The complement of SEQ ID NO:95 is represented by SEQ ID NO:96.

Example 4

This example describes the identification of GSEs that inhibit translocation of the HIV protein Rev.

The methods generally described in Stauber et al. (1998, *Virology* 251:38–48), are used to identify GSEs that inhibit the translocation of Rev HIV protein in a cell. Plasmids CF-24 and CF-367 (vector without insert), and CF-203, CF-261, CF-527, CF-529, CF-537, CF-545, CF-619, CF-653, CF-659, CF-660, CF-662 and CF-674 are transfected into cells that express a Rev protein fused to a green fluorescent protein (Rev-GFP). Confocal microscopy is used to determine whether transport of Rev-GFP fusion protein between the nucleus and the cytoplasm of a cell transfected with a plasmid containing a GSE nucleic acid sequence is inhibited by expression of the GSE. The observations using cells transfected with GSE are compared with cells transfected with vector alone.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for selecting a HIV inhibitor to retard HIV infection, comprising:

(a) exposing a cell in vitro to a putative inhibitory compound, wherein said cell contains a biologically active form of SH2-containing inositol 5-phosphatase;

(b) measuring the activity of SH2-containing inositol 5-phosphatase in said cell;

(c) determining if said putative inhibitory compound interferes with the activity of SH2-containing inositol 5-phosphatase; and (d) selecting said putative inhibitory compound as a HIV inhibitor to retard HIV infection if it interferes with the activity of SH2-containing inositol 5-phosphatase.

2. The method of claim 1, wherein said cell is selected from the group consisting of a HIV-infected cell and a HIV-susceptible cell.

3. The method of claim 1, wherein said cell is cultured in conditions suitable for production of an active form of SH2-containing inositol 5-phosphatase.

4. The method of claim 1, wherein step (c) further comprises determining if a substrate for SH2-containing inositol 5-phosphatase is modified.

* * * * *